(12) United States Patent
Brady et al.

(10) Patent No.: US 7,014,647 B2
(45) Date of Patent: Mar. 21, 2006

(54) SUPPORT FRAME FOR AN EMBOLIC PROTECTION DEVICE

(75) Inventors: Eamon Brady, Elphin (IE); David Vale, Dublin (IE); Ronald Kellly, Athlone (IE); John Neilan, County Galway (IE); Steven Horan, Athlone (IE); Gerard Rabitte, Tuam (IE); Gerry McCaffrey, County Fermanagh (IE)

(73) Assignee: Salviac Limited, Dublin (IE)

( * ) Notice: Subject to any disclaimer, the term of this patent is extended or adjusted under 35 U.S.C. 154(b) by 0 days.

(21) Appl. No.: 10/326,920

(22) Filed: Dec. 23, 2002

(65) Prior Publication Data

US 2003/0144689 A1  Jul. 31, 2003

Related U.S. Application Data

(63) Continuation-in-part of application No. 09/986,132, filed on Nov. 7, 2001, now abandoned, which is a continuation of application No. PCT/IE00/00054, filed on May 8, 2000.

(60) Provisional application No. 60/377,248, filed on May 3, 2002, provisional application No. 60/373,641, filed on Apr. 19, 2002, provisional application No. 60/373,640, filed on Apr. 19, 2002, provisional application No. 60/341,836, filed on Dec. 21, 2001, provisional application No. 60/341,805, filed on Dec. 21, 2001.

(30) Foreign Application Priority Data

May 7, 1999 (IE) ................. PCT/IE99/00035

(51) Int. Cl.
*A61M 29/00* (2006.01)

(52) U.S. Cl. .................................... 606/200

(58) Field of Classification Search ............. 606/200, 606/127, 113, 114
See application file for complete search history.

(56) References Cited

U.S. PATENT DOCUMENTS

| | | | |
|---|---|---|---|
| 2,854,983 A | 10/1958 | Baskin |
| 3,334,629 A | 8/1967 | Cohn |
| 3,435,824 A | 4/1969 | Gamponia |
| 3,540,431 A | 11/1970 | Mebin-Uddin |
| 3,692,029 A | 9/1972 | Adair |
| 3,730,185 A | 5/1973 | Cook et al. |
| 3,952,747 A | 4/1976 | Kimmell, Jr. |
| 4,295,464 A | 10/1981 | Shihata |
| 4,404,971 A | 9/1983 | LeVeen et al. |
| 4,423,725 A | 1/1984 | Baran et al. |
| 4,425,908 A | 1/1984 | Simon |
| 4,445,892 A | 5/1984 | Hussein et al. |

(Continued)

FOREIGN PATENT DOCUMENTS

DE  3706077  6/1988

(Continued)

OTHER PUBLICATIONS

US 6,348,062, 02/2002, Hopkins et al. (withdrawn)

*Primary Examiner*—Kevin T. Truong
(74) *Attorney, Agent, or Firm*—Sughrue Mion, PLLC

(57) ABSTRACT

An embolic protection device has a support frame incorporating tethering features for connecting the support frame distally and/or proximally and/or intermediately to a carrier. Tethers may also be used additionally or alternatively for connecting various elements of a support frame. The tethers may be used to connect a support hoop 503 to a tubular member 504. The tethers provide added safety and stability to the frame without any increase in the length of the device when wrapped down for delivery.

35 Claims, 70 Drawing Sheets

U.S. PATENT DOCUMENTS

| | | |
|---|---|---|
| 4,493,711 A | 1/1985 | Chin et al. |
| 4,512,762 A | 4/1985 | Spears |
| 4,585,000 A | 4/1986 | Hershenson |
| 4,586,919 A | 5/1986 | Taheri |
| 4,610,662 A | 9/1986 | Weikl et al. |
| 4,611,594 A | 9/1986 | Grayhack et al. |
| 4,619,246 A | 10/1986 | Molgaard-Nielsen et al. |
| 4,643,184 A | 2/1987 | Mobin-Uddin |
| 4,650,466 A | 3/1987 | Luther |
| 4,712,551 A | 12/1987 | Rayhunabad |
| 4,723,549 A | 2/1988 | Wholey et al. |
| 4,781,177 A | 11/1988 | Lebigot |
| 4,790,812 A | 12/1988 | Hawkins, Jr. et al. |
| 4,794,928 A | 1/1989 | Kletschka |
| 4,807,626 A | 2/1989 | McGirr |
| 4,817,600 A | 4/1989 | Herms et al. |
| 4,832,055 A | 5/1989 | Palestrant |
| 4,867,156 A | 9/1989 | Stack et al. |
| 4,873,978 A | 10/1989 | Ginsburg |
| 4,926,858 A | 5/1990 | Gifford, III et al. |
| 4,927,426 A | 5/1990 | Dretler |
| 4,957,501 A | 9/1990 | Lahille et al. |
| 4,969,891 A | 11/1990 | Gevertz |
| 4,990,156 A | 2/1991 | Lefebvre |
| 5,011,488 A | 4/1991 | Ginsburg |
| 5,026,377 A | 6/1991 | Burton et al. |
| 5,053,008 A | 10/1991 | Bajaj |
| 5,092,839 A | 3/1992 | Kipperman |
| 5,100,423 A | 3/1992 | Fearnot |
| 5,108,419 A | 4/1992 | Reger et al. |
| 5,122,125 A | 6/1992 | Deuss |
| 5,133,733 A | 7/1992 | Rasmussen et al. |
| 5,171,233 A | 12/1992 | Amplatz et al. |
| 5,178,158 A | 1/1993 | de Toledo |
| 5,192,284 A | 3/1993 | Pleatman |
| 5,324,304 A | 6/1994 | Rasmussen |
| 5,329,942 A | 7/1994 | Gunther et al. |
| 5,336,234 A | 8/1994 | Vigil et al. |
| 5,354,310 A | 10/1994 | Garnic et al. |
| 5,370,657 A | 12/1994 | Irie |
| 5,375,612 A | 12/1994 | Cottenceau et al. |
| 5,383,887 A | 1/1995 | Nadal |
| 5,387,219 A | 2/1995 | Rappe |
| 5,405,329 A | 4/1995 | Durand |
| 5,421,832 A | 6/1995 | Lefebvre |
| 5,454,788 A | 10/1995 | Walker et al. |
| 5,540,707 A | 7/1996 | Ressemann et al. |
| 5,549,626 A | 8/1996 | Miller et al. |
| 5,593,394 A | 1/1997 | Kanesaka et al. |
| 5,658,296 A | 8/1997 | Bates et al. |
| 5,662,671 A | 9/1997 | Barbut et al. |
| 5,669,933 A | 9/1997 | Simon et al. |
| 5,683,451 A | 11/1997 | Lenker et al. |
| 5,695,519 A | 12/1997 | Summers et al. |
| 5,709,704 A | 1/1998 | Nott et al. |
| 5,720,764 A | 2/1998 | Naderlinger |
| 5,766,203 A | 6/1998 | Imran et al. |
| 5,769,816 A | 6/1998 | Barbut et al. |
| 5,769,871 A | 6/1998 | Mers Kelly et al. |
| 5,779,716 A | 7/1998 | Cano et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,823,992 A | 10/1998 | Salmon et al. |
| 5,827,324 A | 10/1998 | Cassell et al. |
| 5,834,449 A | 11/1998 | Thompson et al. |
| 5,836,969 A | 11/1998 | Kim et al. |
| 5,843,167 A | 12/1998 | Dwyer et al. |
| 5,846,260 A | 12/1998 | Maahs |
| 5,848,964 A | 12/1998 | Samuels |
| 5,876,367 A | 3/1999 | Kaganov et al. |
| 5,882,329 A | 3/1999 | Patterson et al. |
| 5,895,398 A | 4/1999 | Wensel et al. |
| 5,895,410 A | 4/1999 | Forber et al. |
| 5,897,567 A | 4/1999 | Ressemann et al. |
| 5,902,334 A | 5/1999 | Dwyer et al. |
| 5,910,154 A | 6/1999 | Tsugita et al. |
| 5,911,725 A | 6/1999 | Boury |
| 5,911,734 A | 6/1999 | Tsugita et al. |
| 5,928,261 A | 7/1999 | Ruiz |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,968,071 A | 10/1999 | Chevillon |
| 5,976,172 A | 11/1999 | Homsma et al. |
| 5,984,947 A | 11/1999 | Smith |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,093 A | 1/2000 | Nott et al. |
| 6,027,520 A | 2/2000 | Tsugita et al. |
| 6,042,598 A | 3/2000 | Tsugita et al. |
| 6,051,014 A | 4/2000 | Jang |
| 6,053,932 A | 4/2000 | Daniel et al. |
| 6,048,645 A | 5/2000 | Tu |
| 6,059,814 A * | 5/2000 | Ladd ........................ 606/200 |
| 6,066,149 A | 5/2000 | Samson et al. |
| 6,074,357 A | 6/2000 | Kaganov et al. |
| 6,063,173 A | 7/2000 | Balceta et al. |
| 6,083,239 A | 7/2000 | Addis |
| 6,086,577 A | 7/2000 | Ken et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,123,715 A | 9/2000 | Amplatz |
| 6,129,739 A | 10/2000 | Khosravi |
| 6,132,458 A | 10/2000 | Staehle et al. |
| 6,142,987 A | 11/2000 | Tsugita |
| 6,146,404 A | 11/2000 | Kim et al. |
| 6,152,946 A | 11/2000 | Broome et al. |
| 6,165,200 A | 12/2000 | Tsugita et al. |
| 6,168,579 B1 | 1/2001 | Tsugita |
| 6,168,604 B1 | 1/2001 | Cano |
| 6,171,327 B1 | 1/2001 | Daniel et al. |
| 6,171,328 B1 | 1/2001 | Addis |
| 6,176,849 B1 | 1/2001 | Yang et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 * | 6/2001 | Addis ........................ 606/200 |
| 6,245,088 B1 | 6/2001 | Lowery |
| 6,245,089 B1 | 6/2001 | Daniel et al. |
| 6,251,122 B1 | 6/2001 | Tsukernik |
| 6,254,563 B1 | 7/2001 | Macoviak et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |

| | | | | | | |
|---|---|---|---|---|---|---|
| 6,270,513 B1 | 8/2001 | Tsugita et al. | | 6,551,342 B1 | 4/2003 | Shen et al. |
| 6,273,901 B1 | 8/2001 | Whitcher et al. | | 6,558,405 B1 | 5/2003 | McInnes |
| 6,277,138 B1 | 8/2001 | Levinson et al. | | 6,562,058 B1 | 5/2003 | Seguin |
| 6,277,139 B1 | 8/2001 | Levinson et al. | | 6,565,591 B1 | 5/2003 | Brady et al. |
| 6,290,710 B1 | 9/2001 | Cryer et al. | | 6,569,184 B1 | 5/2003 | Huter |
| 6,295,989 B1 | 10/2001 | Connors, III | | 6,575,995 B1 | 6/2003 | Huter et al. |
| 6,306,163 B1 | 10/2001 | Fitz | | 6,575,996 B1 * | 6/2003 | Denison et al. .............. 606/200 |
| 6,319,242 B1 | 11/2001 | Patterson et al. | | 6,575,997 B1 | 6/2003 | Palmer et al. |
| 6,325,815 B1 | 12/2001 | Kusleika et al. | | 6,582,447 B1 | 6/2003 | Patel et al. |
| 6,336,934 B1 | 1/2002 | Gilson et al. | | 6,582,448 B1 | 6/2003 | Boyle et al. |
| 6,340,364 B1 | 1/2002 | Kanesaka | | 6,585,756 B1 | 7/2003 | Strecker |
| 6,346,116 B1 | 2/2002 | Brooks et al. | | 6,589,263 B1 | 7/2003 | Hopkins et al. |
| 6,348,056 B1 | 2/2002 | Bates et al. | | 6,589,265 B1 | 7/2003 | Palmer et al. |
| 6,355,051 B1 | 3/2002 | Sisskind et al. | | 6,592,546 B1 | 7/2003 | Barbut et al. |
| 6,361,545 B1 | 3/2002 | Macoviak et al. | | 6,592,606 B1 | 7/2003 | Huter et al. |
| 6,361,546 B1 | 3/2002 | Khosravi | | 6,592,616 B1 | 7/2003 | Stack et al. |
| 6,364,895 B1 | 4/2002 | Greenhalgh | | 6,596,011 B1 | 7/2003 | Johnson et al. |
| 6,371,935 B1 | 4/2002 | Macoviak et al. | | 6,599,307 B1 | 7/2003 | Huter et al. |
| 6,371,969 B1 | 4/2002 | Tsugita et al. | | 6,602,269 B1 | 8/2003 | Wallace et al. |
| 6,371,970 B1 | 4/2002 | Khosravi et al. | | 6,602,271 B1 | 8/2003 | Adams et al. |
| 6,371,971 B1 | 4/2002 | Tsugita et al. | | 6,602,272 B1 | 8/2003 | Boylan et al. |
| 6,375,670 B1 | 4/2002 | Greenhalgh | | 6,605,102 B1 | 8/2003 | Mazzocchi et al. |
| 6,383,206 B1 | 5/2002 | Gillick et al. | | 6,605,111 B1 | 8/2003 | Bose et al. |
| 6,391,044 B1 | 5/2002 | Yadav et al. | | 6,610,077 B1 | 8/2003 | Hancock et al. |
| 6,394,978 B1 | 5/2002 | Boyle et al. | | 6,616,679 B1 | 9/2003 | Khosravi et al. |
| 6,395,014 B1 | 5/2002 | Macoviak et al. | | 6,616,680 B1 | 9/2003 | Thielen |
| 6,395,017 B1 | 5/2002 | Dwyer et al. | | 6,616,681 B1 | 9/2003 | Hanson et al. |
| 6,398,756 B1 | 6/2002 | Peterson et al. | | 6,616,682 B1 | 9/2003 | Joergensen et al. |
| 6,402,771 B1 | 6/2002 | Palmer et al. | | 6,620,148 B1 | 9/2003 | Tsugita et al. |
| 6,406,471 B1 | 6/2002 | Jang et al. | | 6,620,182 B1 | 9/2003 | Khosravi |
| 6,423,032 B1 | 7/2002 | Parodi | | 6,623,450 B1 | 9/2003 | Dutta |
| 6,425,909 B1 | 7/2002 | Dieck et al. | | 6,632,236 B1 | 10/2003 | Hogendijk |
| 6,428,559 B1 | 8/2002 | Johnson | | 6,632,241 B1 | 10/2003 | Hancock et al. |
| 6,432,122 B1 | 8/2002 | Gilson et al. | | 6,635,070 B1 | 10/2003 | Leeflang et al. |
| 6,436,121 B1 | 8/2002 | Blom | | 6,638,294 B1 | 10/2003 | Palmer |
| 6,443,926 B1 | 9/2002 | Kletschka | | 6,645,220 B1 | 11/2003 | Huter et al. |
| 6,443,971 B1 | 9/2002 | Boylan et al. | | 6,645,223 B1 | 11/2003 | Boyle et al. |
| 6,443,979 B1 | 9/2002 | Stalker et al. | | 6,645,224 B1 | 11/2003 | Gilson et al. |
| 6,447,530 B1 | 9/2002 | Ostrovsky et al. | | 6,652,480 B1 | 11/2003 | Imran et al. |
| 6,458,139 B1 | 10/2002 | Palmer et al. | | 6,652,505 B1 | 11/2003 | Tsugita et al. |
| 6,461,370 B1 | 10/2002 | Gray et al. | | 6,652,554 B1 | 11/2003 | Wholey et al. |
| 6,468,291 B1 | 10/2002 | Bates et al. | | 6,652,557 B1 | 11/2003 | MacDonald |
| 6,482,222 B1 | 11/2002 | Bruckheimer et al. | | 6,656,202 B1 | 12/2003 | Papp et al. |
| 6,485,497 B1 | 11/2002 | Wensel et al. | | 6,660,021 B1 | 12/2003 | Palmer et al. |
| 6,485,500 B1 | 11/2002 | Kokish et al. | | 6,663,650 B1 | 12/2003 | Sepetka et al. |
| 6,485,501 B1 | 11/2002 | Green | | 6,663,652 B1 | 12/2003 | Daniel et al. |
| 6,485,502 B1 | 11/2002 | Don Michael et al. | | 2001/0000799 A1 | 5/2001 | Wessman et al. |
| 6,494,895 B1 | 12/2002 | Addis | | 2001/0001315 A1 | 5/2001 | Bates et al. |
| 6,506,203 B1 | 1/2003 | Boyle et al. | | 2001/0007947 A1 | 7/2001 | Kanesaka |
| 6,506,205 B1 | 1/2003 | Goldberg et al. | | 2001/0012951 A1 | 8/2001 | Bates et al. |
| 6,511,492 B1 | 1/2003 | Rosenbluth | | 2001/0020175 A1 | 9/2001 | Yassour et al. |
| 6,511,496 B1 | 1/2003 | Huter et al. | | 2001/0025187 A1 | 9/2001 | Okada |
| 6,511,497 B1 | 1/2003 | Braun et al. | | 2001/0031982 A1 | 10/2001 | Peterson et al. |
| 6,511,503 B1 | 1/2003 | Burkett et al. | | 2001/0037431 A1 | 11/2001 | De Vries et al. |
| 6,514,273 B1 | 2/2003 | Voss et al. | | 2001/0041908 A1 | 11/2001 | Levinson et al. |
| 6,517,550 B1 | 2/2003 | Konya et al. | | 2001/0044632 A1 | 11/2001 | Daniel et al. |
| 6,517,559 B1 | 2/2003 | O'Connell | | 2002/0002384 A1 | 1/2002 | Gilson et al. |
| 6,520,978 B1 | 2/2003 | Blackledge et al. | | 2002/0022858 A1 | 2/2002 | Demond et al. |
| 6,527,746 B1 | 3/2003 | Oslund et al. | | 2002/0022860 A1 | 2/2002 | Borillo et al. |
| 6,530,939 B1 | 3/2003 | Hopkins et al. | | 2002/0026211 A1 | 2/2002 | Khosravi et al. |
| 6,530,940 B1 | 3/2003 | Fisher | | 2002/0026213 A1 | 2/2002 | Gilson et al. |
| 6,533,800 B1 | 3/2003 | Barbut | | 2002/0032460 A1 | 3/2002 | Kusleika et al. |
| 6,537,294 B1 | 3/2003 | Boyle et al. | | 2002/0045916 A1 | 4/2002 | Gray et al. |
| 6,537,295 B1 | 3/2003 | Petersen | | 2002/0045918 A1 | 4/2002 | Suon et al. |
| 6,537,296 B1 | 3/2003 | Levinson et al. | | 2002/0049467 A1 | 4/2002 | Gilson et al. |
| 6,537,297 B1 | 3/2003 | Tsugita et al. | | 2002/0049468 A1 | 4/2002 | Strecker et al. |
| 6,540,722 B1 | 4/2003 | Boyle et al. | | 2002/0052626 A1 | 5/2002 | Gilson et al. |
| 6,540,767 B1 | 4/2003 | Walak et al. | | 2002/0052638 A1 | 5/2002 | Zadno-Azizi |
| 6,540,768 B1 | 4/2003 | Diaz et al. | | 2002/0055747 A1 | 5/2002 | Cano et al. |
| 6,544,279 B1 | 4/2003 | Hopkins et al. | | 2002/0055767 A1 | 5/2002 | Forde et al. |
| 6,544,280 B1 | 4/2003 | Daniel et al. | | 2002/0058911 A1 | 5/2002 | Gilson et al. |
| 6,547,760 B1 | 4/2003 | Samson et al. | | 2002/0058963 A1 | 5/2002 | Vale et al. |
| 6,551,341 B1 | 4/2003 | Boylan et al. | | 2002/0062133 A1 | 5/2002 | Gilson et al. |

| | | | | | |
|---|---|---|---|---|---|
| 2002/0062135 A1 | 5/2002 | Mazzocchi et al. | 2003/0060782 A1 | 3/2003 | Bose et al. |
| 2002/0065507 A1 | 5/2002 | Zadno-Azizi | 2003/0060843 A1 | 3/2003 | Boucher |
| 2002/0068954 A1 | 6/2002 | Foster | 2003/0060844 A1 | 3/2003 | Borillo et al. |
| 2002/0068955 A1 | 6/2002 | Khosravi | 2003/0065354 A1 | 4/2003 | Boyle et al. |
| 2002/0072730 A1 | 6/2002 | McGill et al. | 2003/0069596 A1 | 4/2003 | Esuri |
| 2002/0072765 A1 | 6/2002 | Mazzocchi et al. | 2003/0069597 A1 | 4/2003 | Petersen |
| 2002/0082525 A1 | 6/2002 | Oslund et al. | 2003/0078519 A1 | 4/2003 | Salahieh et al. |
| 2002/0082639 A1 | 6/2002 | Broome et al. | 2003/0078614 A1 | 4/2003 | Salahieh et al. |
| 2002/0091408 A1 | 7/2002 | Sutton et al. | 2003/0083692 A1 | 5/2003 | Vrba et al. |
| 2002/0091409 A1 | 7/2002 | Sutton et al. | 2003/0083693 A1 | 5/2003 | Daniel et al. |
| 2002/0095141 A1 | 7/2002 | Belef et al. | 2003/0100917 A1 | 5/2003 | Boyle et al. |
| 2002/0095170 A1 | 7/2002 | Krolik et al. | 2003/0100918 A1 | 5/2003 | Duane |
| 2002/0095171 A1 | 7/2002 | Belef | 2003/0105484 A1 | 6/2003 | Boyle et al. |
| 2002/0095172 A1 | 7/2002 | Mazzocchi et al. | 2003/0109824 A1 | 6/2003 | Anderson et al. |
| 2002/0095173 A1 | 7/2002 | Mazzocchi et al. | 2003/0114879 A1 | 6/2003 | Euteneuer et al. |
| 2002/0095174 A1 | 7/2002 | Tsugita et al. | 2003/0114880 A1 | 6/2003 | Hansen et al. |
| 2002/0099407 A1 | 7/2002 | Becker et al. | 2003/0120303 A1 | 6/2003 | Boyle et al. |
| 2002/0103501 A1 | 8/2002 | Diaz et al. | 2003/0125764 A1 | 7/2003 | Brady et al. |
| 2002/0107541 A1 | 8/2002 | Vale et al. | 2003/0130680 A1 | 7/2003 | Russell |
| 2002/0111648 A1 | 8/2002 | Kusleika et al. | 2003/0130681 A1 | 7/2003 | Ungs |
| 2002/0111649 A1 | 8/2002 | Russo et al. | 2003/0130682 A1 | 7/2003 | Broome et al. |
| 2002/0115942 A1 | 8/2002 | Stanford et al. | 2003/0130684 A1 | 7/2003 | Brady et al. |
| 2002/0120286 A1 | 8/2002 | Dobrava et al. | 2003/0130685 A1 | 7/2003 | Daniel et al. |
| 2002/0120287 A1 | 8/2002 | Huter | 2003/0130686 A1 | 7/2003 | Daniel et al. |
| 2002/0121472 A1 | 9/2002 | Garner et al. | 2003/0130687 A1 | 7/2003 | Daniel et al. |
| 2002/0123720 A1 | 9/2002 | Kusleika et al. | 2003/0130688 A1 | 7/2003 | Daniel et al. |
| 2002/0123755 A1 | 9/2002 | Lowe et al. | 2003/0135162 A1 | 7/2003 | Deyette, Jr. et al. |
| 2002/0128679 A1 | 9/2002 | Turovskiy et al. | 2003/0135232 A1 | 7/2003 | Douk et al. |
| 2002/0128680 A1 | 9/2002 | Pavlovic | 2003/0139764 A1 | 7/2003 | Levinson et al. |
| 2002/0128681 A1 | 9/2002 | Broome et al. | 2003/0144670 A1 | 7/2003 | Pavcnik et al. |
| 2002/0133092 A1 | 9/2002 | Oslund et al. | 2003/0144685 A1 | 7/2003 | Boyle et al. |
| 2002/0138094 A1 | 9/2002 | Borillo et al. | 2003/0144686 A1 | 7/2003 | Martinez et al. |
| 2002/0138095 A1 | 9/2002 | Mazzocchi et al. | 2003/0144687 A1 | 7/2003 | Brady et al. |
| 2002/0143360 A1 | 10/2002 | Douk et al. | 2003/0144688 A1 | 7/2003 | Brady et al. |
| 2002/0143361 A1 | 10/2002 | Douk et al. | 2003/0144689 A1 | 7/2003 | Brady et al. |
| 2002/0151927 A1 | 10/2002 | Douk et al. | 2003/0150821 A1 | 8/2003 | Bates et al. |
| 2002/0156456 A1 | 10/2002 | Fisher | 2003/0153942 A1 | 8/2003 | Wang et al. |
| 2002/0156457 A1 | 10/2002 | Fisher | 2003/0153943 A1 | 8/2003 | Michael et al. |
| 2002/0161390 A1 | 10/2002 | Mouw | 2003/0158574 A1 | 8/2003 | Esch et al. |
| 2002/0161392 A1 | 10/2002 | Dubrul | 2003/0163064 A1 | 8/2003 | Vrba et al. |
| 2002/0161393 A1 | 10/2002 | Demond et al. | 2003/0171770 A1 | 9/2003 | Kusleika et al. |
| 2002/0161395 A1 | 10/2002 | Douk et al. | 2003/0171771 A1 | 9/2003 | Anderson et al. |
| 2002/0165576 A1 | 11/2002 | Boyle et al. | 2003/0171803 A1 | 9/2003 | Shimon |
| 2002/0169414 A1 | 11/2002 | Kletschka | 2003/0176884 A1 | 9/2003 | Berrada et al. |
| 2002/0169458 A1 | 11/2002 | Connors, III | 2003/0176885 A1 | 9/2003 | Broome et al. |
| 2002/0169472 A1 | 11/2002 | Douk et al. | 2003/0176886 A1 | 9/2003 | Wholey et al. |
| 2002/0169474 A1 | 11/2002 | Kusleika et al. | 2003/0181942 A1 | 9/2003 | Sutton et al. |
| 2002/0173815 A1 | 11/2002 | Hogendijk et al. | 2003/0181943 A1 | 9/2003 | Daniel et al. |
| 2002/0173817 A1 | 11/2002 | Kletschka et al. | 2003/0187474 A1 | 10/2003 | Keegan et al. |
| 2002/0183873 A1 | 12/2002 | Shadduck | 2003/0187475 A1 | 10/2003 | Tsuqita et al. |
| 2002/0188313 A1 | 12/2002 | Johnson et al. | 2003/0187493 A1 | 10/2003 | Epstein et al. |
| 2002/0188314 A1 | 12/2002 | Anderson et al. | 2003/0187495 A1 | 10/2003 | Cully et al. |
| 2002/0193825 A1 | 12/2002 | McGuckin et al. | 2003/0195555 A1 | 10/2003 | Khairkhahan et al. |
| 2002/0193826 A1 | 12/2002 | McGuckin et al. | 2003/0199819 A1 | 10/2003 | Beck |
| 2002/0193827 A1 | 12/2002 | McGuckin et al. | 2003/0204168 A1 | 10/2003 | Bosma et al. |
| 2002/0193828 A1 | 12/2002 | Griffin et al. | 2003/0208224 A1 | 11/2003 | Broome |
| 2003/0004536 A1 | 1/2003 | Boylan et al. | 2003/0208225 A1 | 11/2003 | Goll et al. |
| 2003/0004537 A1 | 1/2003 | Boyle et al. | 2003/0208226 A1 | 11/2003 | Bruckheimer et al. |
| 2003/0004539 A1 | 1/2003 | Linder et al. | 2003/0208227 A1 | 11/2003 | Thomas |
| 2003/0004540 A1 | 1/2003 | Linder et al. | 2003/0208228 A1 | 11/2003 | Gilson et al. |
| 2003/0004541 A1 | 1/2003 | Linder et al. | 2003/0212361 A1 | 11/2003 | Boyle et al. |
| 2003/0009188 A1 | 1/2003 | Linder et al. | 2003/0212429 A1 | 11/2003 | Keegan et al. |
| 2003/0009189 A1 | 1/2003 | Gilson et al. | 2003/0212431 A1 | 11/2003 | Brady et al. |
| 2003/0015206 A1 | 1/2003 | Roth et al. | 2003/0212434 A1 | 11/2003 | Thielen |
| 2003/0018354 A1 | 1/2003 | Roth et al. | 2003/0216774 A1 | 11/2003 | Larson |
| 2003/0023265 A1 | 1/2003 | Forber | 2003/0220665 A1 | 11/2003 | Eskuri et al. |
| 2003/0028238 A1 | 2/2003 | Burkett et al. | 2003/0225418 A1 | 12/2003 | Eskuri et al. |
| 2003/0032941 A1 | 2/2003 | Boyle et al. | 2003/0229295 A1 | 12/2003 | Houde et al. |
| 2003/0032977 A1 | 2/2003 | Brady et al. | 2003/0229374 A1 | 12/2003 | Brady et al. |
| 2003/0040772 A1 | 2/2003 | Hyodoh et al. | 2003/0233117 A1 | 12/2003 | Adams et al. |
| 2003/0042186 A1 | 3/2003 | Boyle et al. | | | |
| 2003/0045898 A1 | 3/2003 | Harrison et al. | | | |
| 2003/0057156 A1 | 3/2003 | Peterson et al. | | | |

FOREIGN PATENT DOCUMENTS

| | | |
|---|---|---|
| EP | 0256683 | 2/1988 |
| EP | 0533511 | 3/1993 |
| EP | 0596172 | 5/1994 |
| EP | 0655228 | 5/1995 |
| EP | 0743046 | 11/1996 |
| EP | 0759287 | 2/1997 |
| EP | 0791340 | 8/1997 |
| EP | 0827756 | 3/1998 |
| EP | 1123688 | 8/2001 |
| EP | 1127556 | 8/2001 |
| EP | 1149566 | 10/2001 |
| EP | 1172073 | 1/2002 |
| EP | 1181900 | 2/2002 |
| EP | 1 277 448 A1 | 1/2003 |
| FR | 2 580 504 | 10/1986 |
| FR | 2 616 666 | 12/1988 |
| FR | 2 694 687 | 2/1994 |
| FR | 2 768 326 | 3/1999 |
| FR | 2 831 422 | 5/2003 |
| GB | 2020557 | 11/1979 |
| GB | 2200848 | 8/1988 |
| WO | WO 88/09683 | 12/1988 |
| WO | WO 89/07422 | 8/1989 |
| WO | WO 94/24946 | 11/1994 |
| WO | WO 95/34254 | 12/1995 |
| WO | WO 95/34339 | 12/1995 |
| WO | WO 96/01591 | 1/1996 |
| WO | WO 96/39998 | 12/1996 |
| WO | WO 97/03810 | 2/1997 |
| WO | WO 97/17021 | 5/1997 |
| WO | WO 97/17100 | 5/1997 |
| WO | WO 97/17914 | 5/1997 |
| WO | WO 97/27808 | 8/1997 |
| WO | WO 97/42879 | 11/1997 |
| WO | WO 98/24377 | 6/1998 |
| WO | WO 98/30265 | 7/1998 |
| WO | WO 98/33443 | 8/1998 |
| WO | WO 98/38920 | 9/1998 |
| WO | WO 98/39053 | 9/1998 |
| WO | WO 98/46297 | 10/1998 |
| WO | WO 98/49952 | 11/1998 |
| WO | WO 98/50103 | 11/1998 |
| WO | WO 98/51237 | 11/1998 |
| WO | WO 99/16382 | 4/1999 |
| WO | WO 99/20335 | 4/1999 |
| WO | WO 99/22673 | 5/1999 |
| WO | WO 99/23976 | 5/1999 |
| WO | WO 99/25252 | 5/1999 |
| WO | WO 99/44510 | 9/1999 |
| WO | WO 99/44542 | 9/1999 |
| WO | WO 99/51167 | 10/1999 |
| WO | WO 99/55236 | 11/1999 |
| WO | WO 00/07521 | 2/2000 |
| WO | WO 00/07656 | 2/2000 |
| WO | WO 00/16705 | 3/2000 |
| WO | WO 00/21604 | 4/2000 |
| WO | WO 00/44428 | 8/2000 |
| WO | WO 00/49970 | 8/2000 |
| WO | WO 00/56390 | 9/2000 |
| WO | WO 00/66031 | 11/2000 |
| WO | WO 00/67664 | 11/2000 |
| WO | WO 00/67665 | 11/2000 |
| WO | WO 00/67666 | 11/2000 |
| WO | WO 00/67667 | 11/2000 |
| WO | WO 00/67668 | 11/2000 |
| WO | WO 00/67669 | 11/2000 |
| WO | WO 00/67670 | 11/2000 |
| WO | WO 00/67671 | 11/2000 |
| WO | WO 00/67829 | 11/2000 |
| WO | WO 00/76390 | 12/2000 |
| WO | WO 01/05329 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10343 | 2/2001 |
| WO | WO 01/12082 | 2/2001 |
| WO | WO 01/15629 | 3/2001 |
| WO | WO 01/15630 | 3/2001 |
| WO | WO 01/21077 | 3/2001 |
| WO | WO 0121100 | 3/2001 |
| WO | WO 01/35857 | 5/2001 |
| WO | WO 01/35858 | 5/2001 |
| WO | WO 01/43662 | 6/2001 |
| WO | WO 01/45590 | 6/2001 |
| WO | WO 01/45591 | 6/2001 |
| WO | WO 01/45592 | 6/2001 |
| WO | WO 01/49208 | 7/2001 |
| WO | WO 01/49209 | 7/2001 |
| WO | WO 01/49215 | 7/2001 |
| WO | WO 01/50982 | 7/2001 |
| WO | WO 01/52768 | 7/2001 |
| WO | WO 01/72205 | 10/2001 |
| WO | WO 01/80776 | 11/2001 |
| WO | WO 01/80777 | 11/2001 |
| WO | WO 01/82830 | 11/2001 |
| WO | WO 01/82831 | 11/2001 |
| WO | WO 01/87183 | 11/2001 |
| WO | WO 01/89413 | 11/2001 |
| WO | WO 01/97714 | 12/2001 |
| WO | WO 02/043595 | 6/2002 |
| WO | WO 02/083225 | 10/2002 |
| WO | WO 03/022325 | 3/2003 |
| WO | WO 03/047648 | 6/2003 |
| WO | WO 03/084434 | 10/2003 |
| WO | WO 03/084435 | 10/2003 |
| WO | WO 03/084436 | 10/2003 |
| WO | WO 03/088805 | 10/2003 |
| WO | WO 03/088869 | 10/2003 |

* cited by examiner

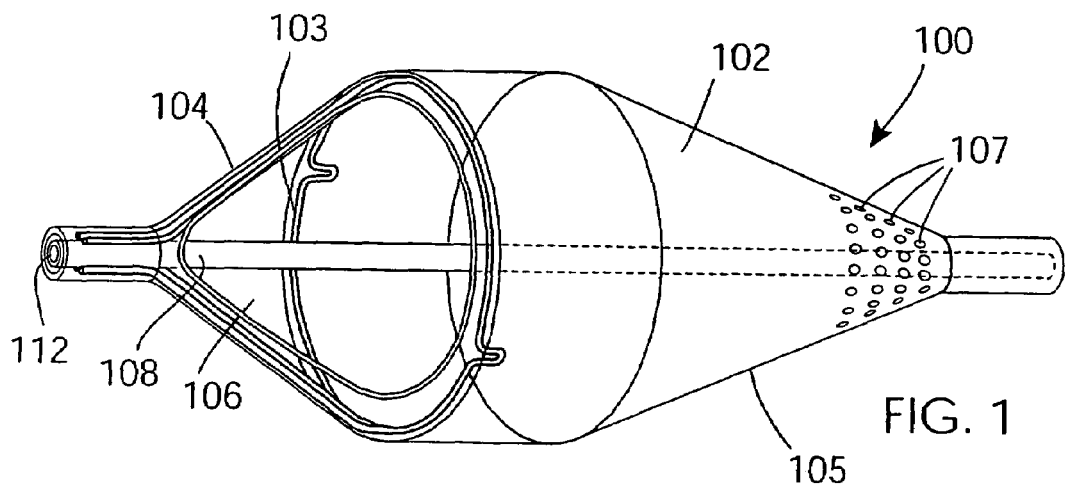
FIG. 1
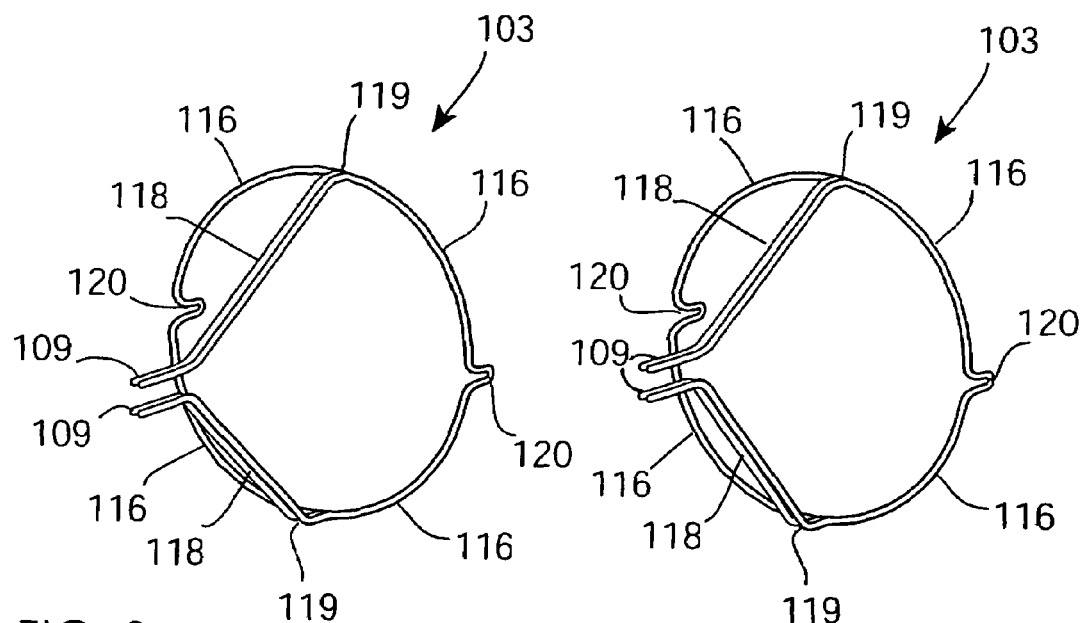
FIG. 2
FIG. 3
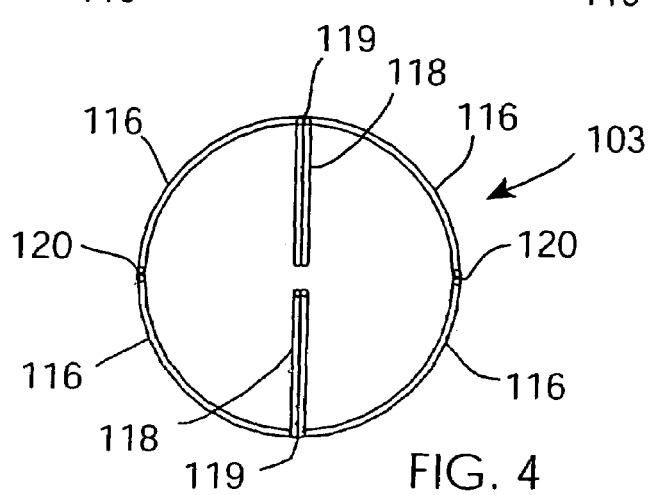
FIG. 4

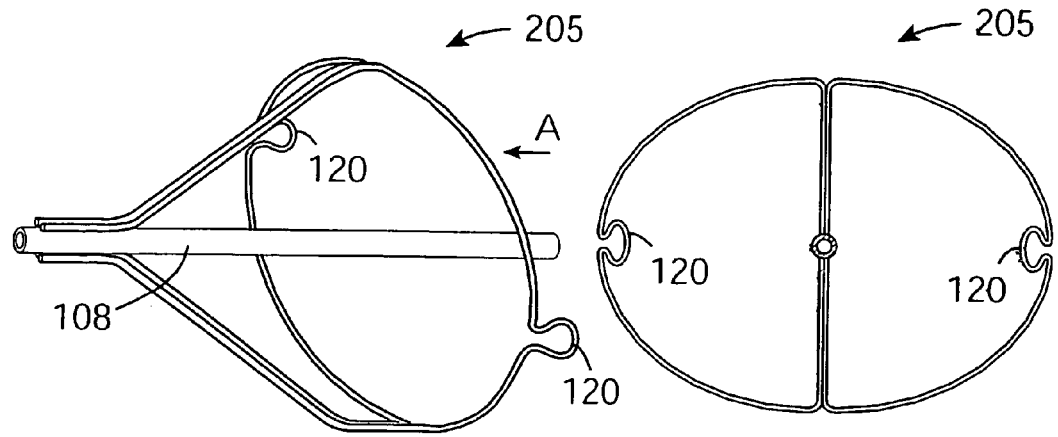
FIG. 46
FIG. 47
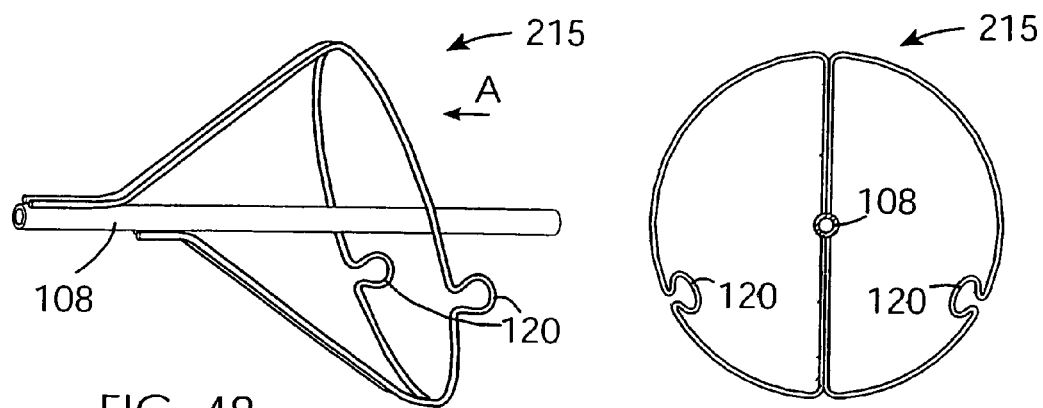
FIG. 48
FIG. 49
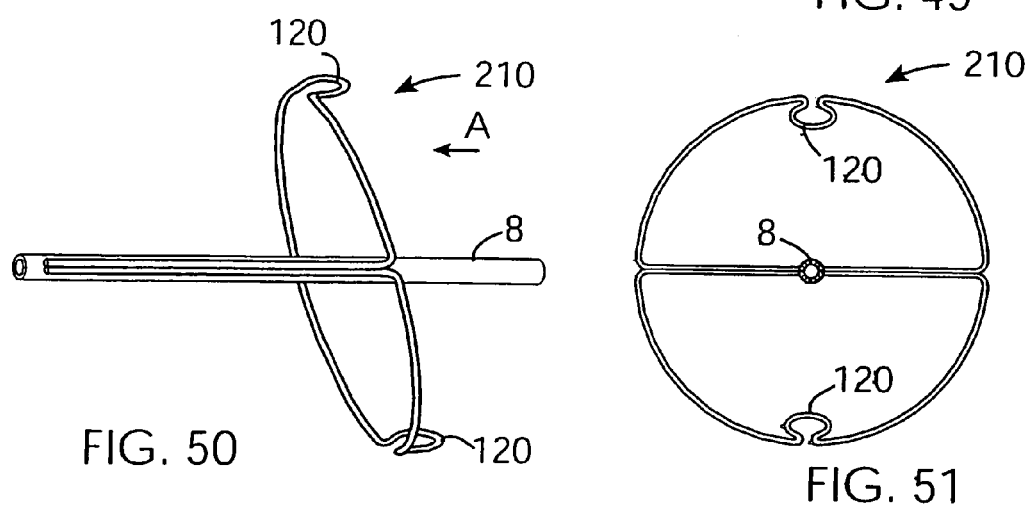
FIG. 50
FIG. 51

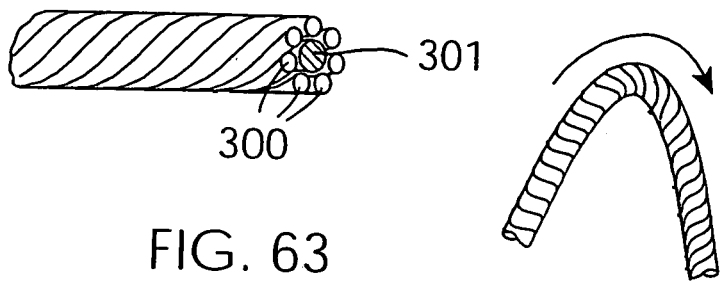
FIG. 63
FIG. 64
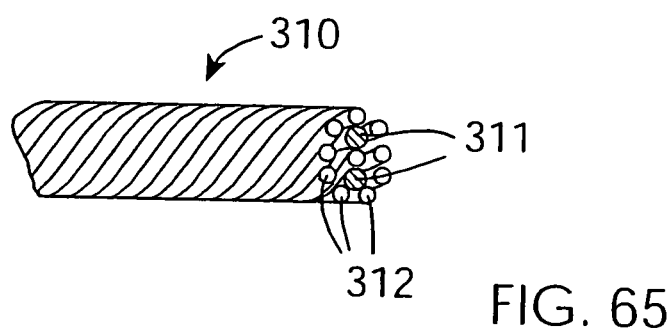
FIG. 65
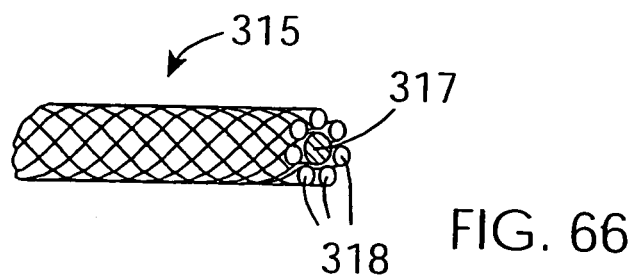
FIG. 66
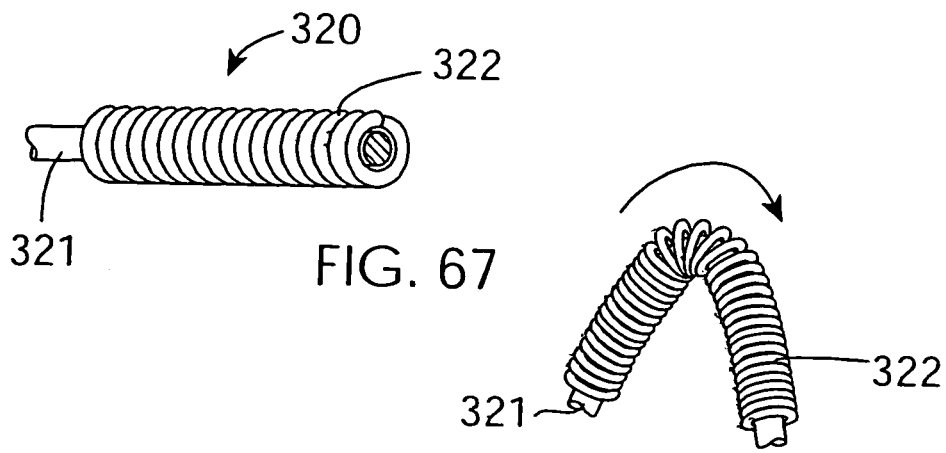
FIG. 67
FIG. 68

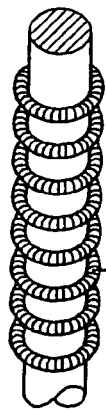 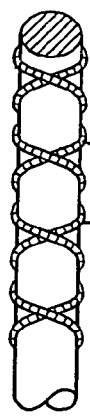 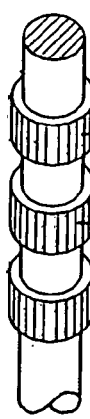 
FIG. 78  FIG. 79  FIG. 80  FIG. 81
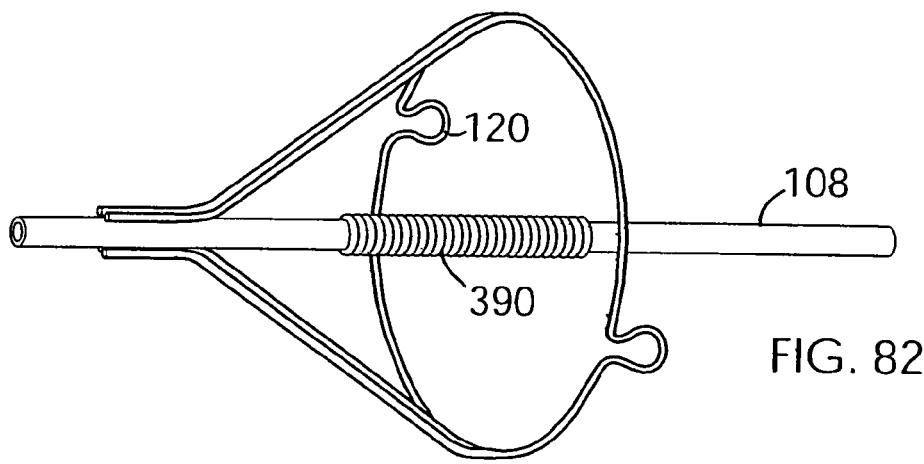
FIG. 82
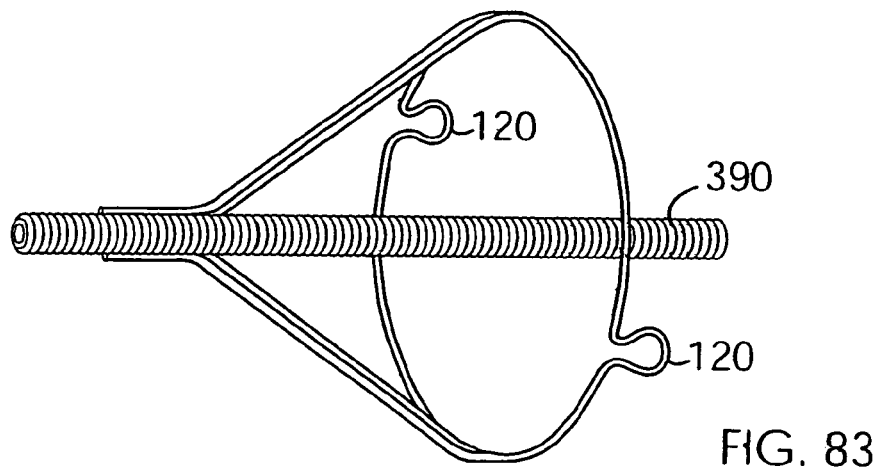
FIG. 83

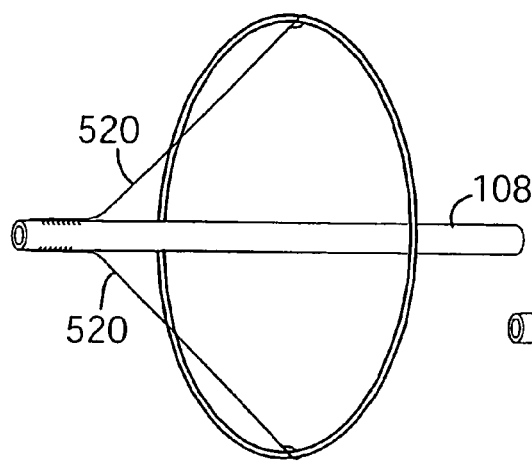
FIG. 91
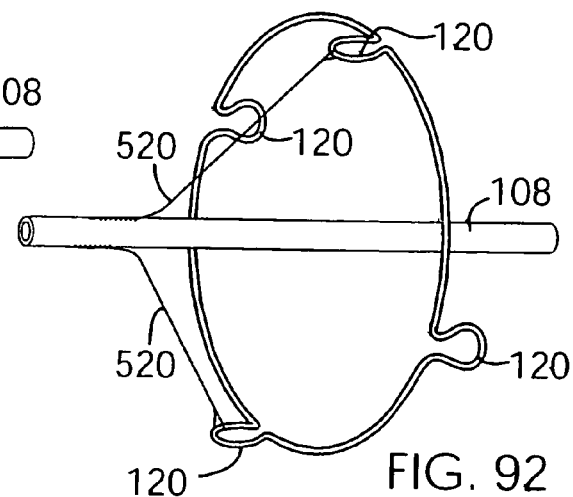
FIG. 92
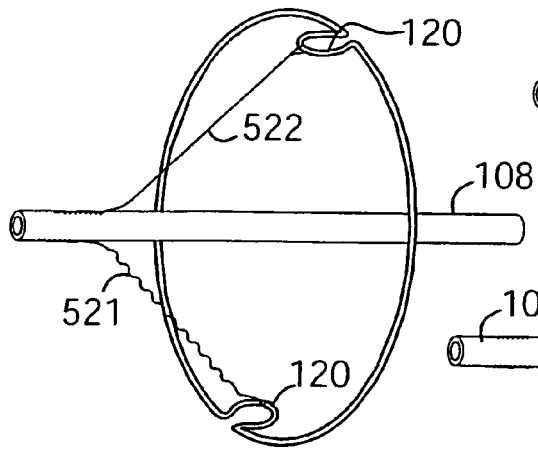
FIG. 93
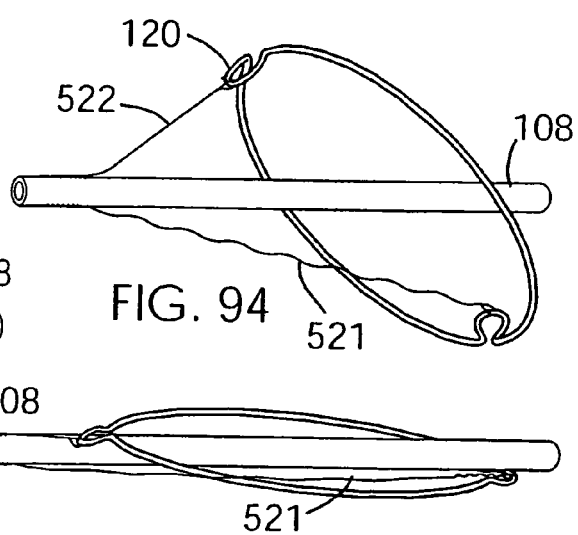
FIG. 94
FIG. 95
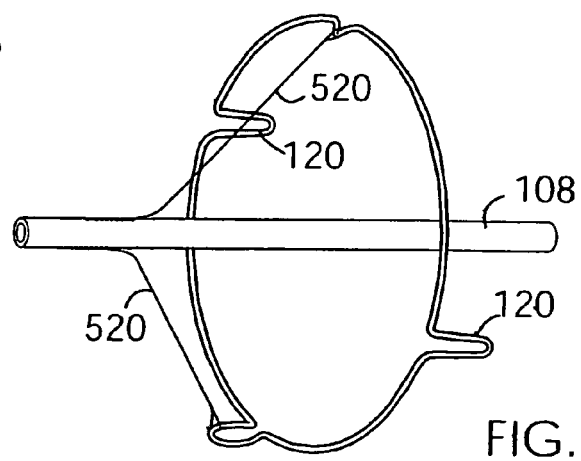
FIG. 96

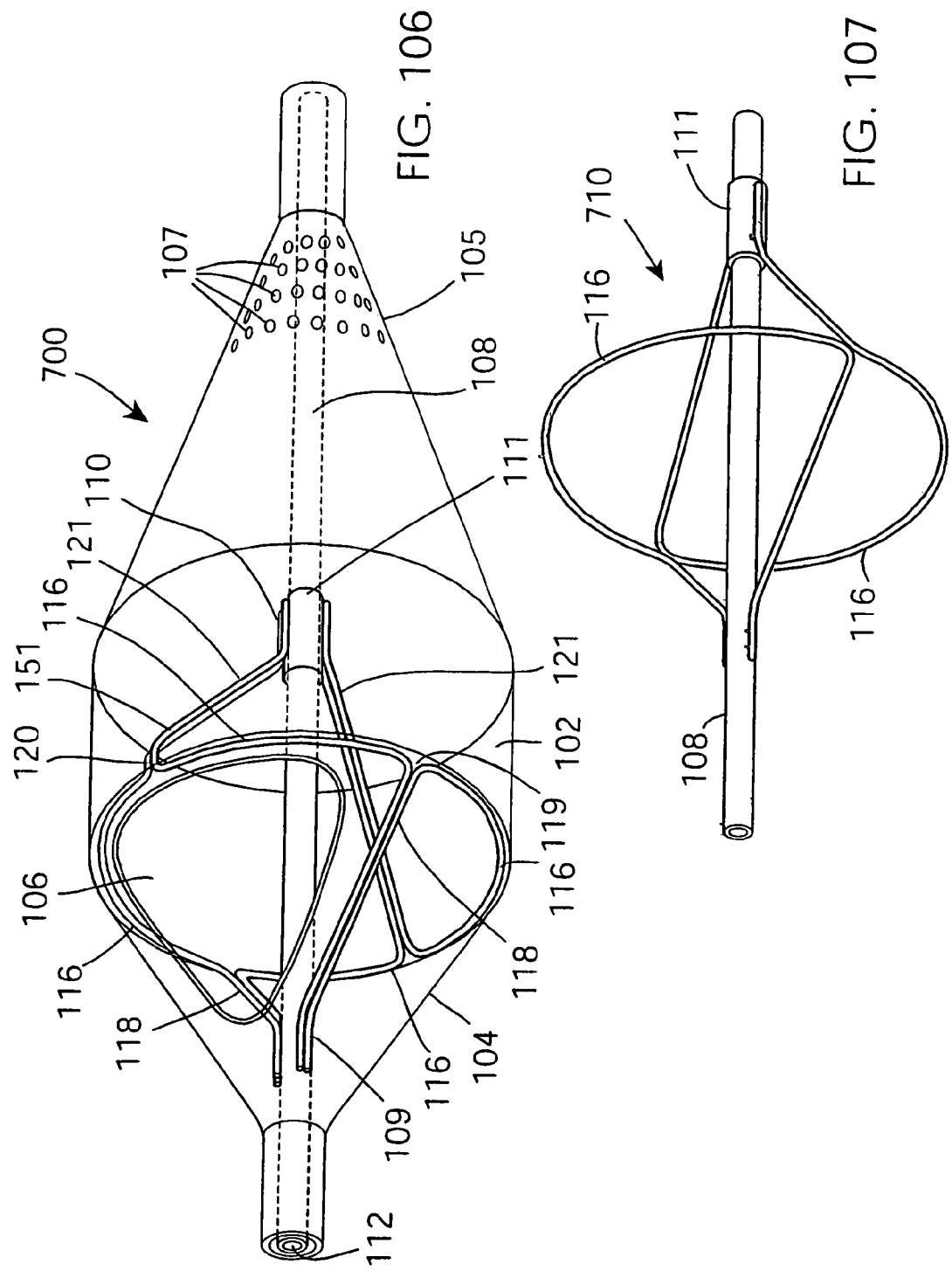

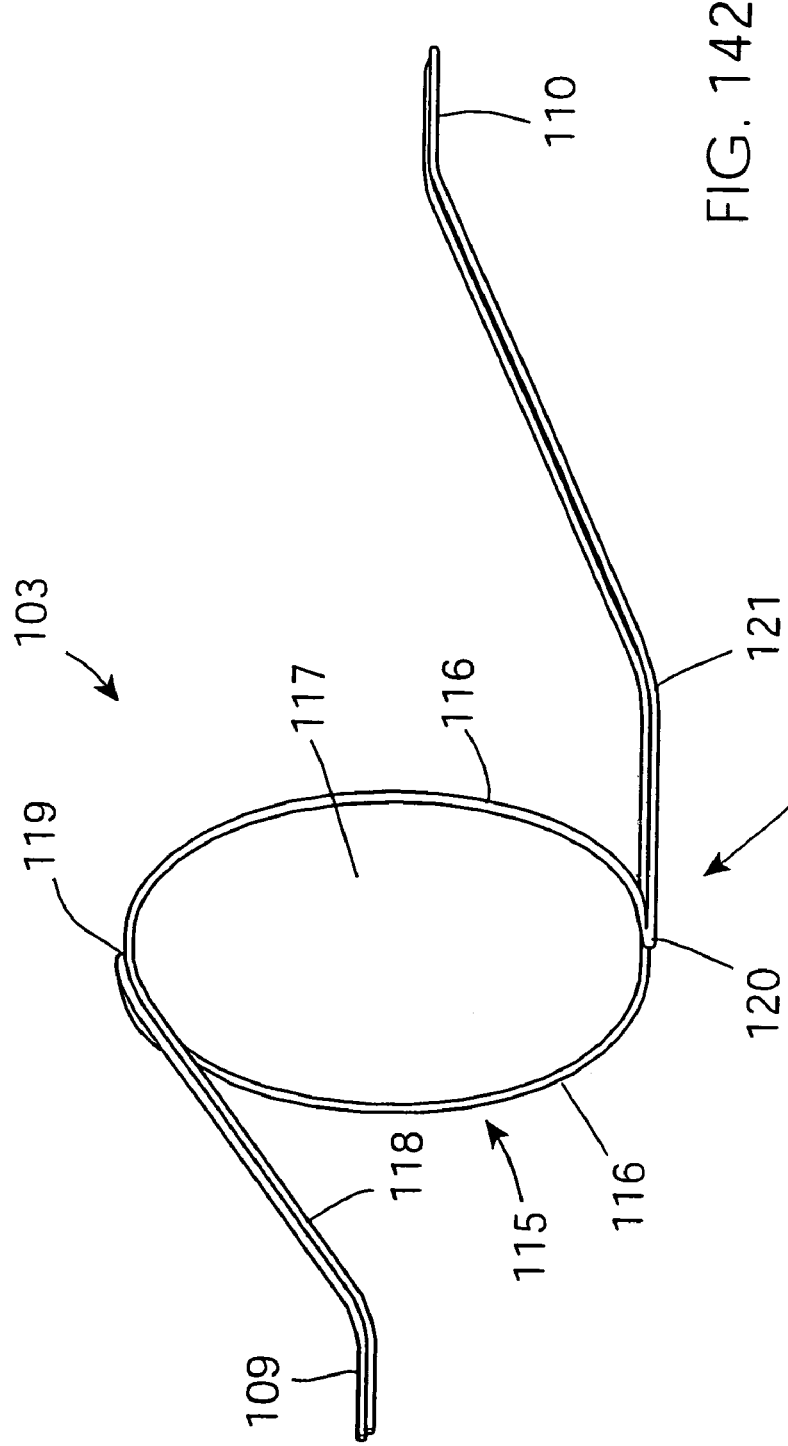
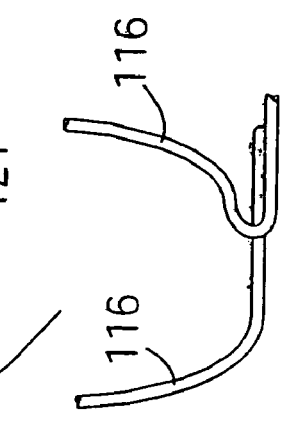
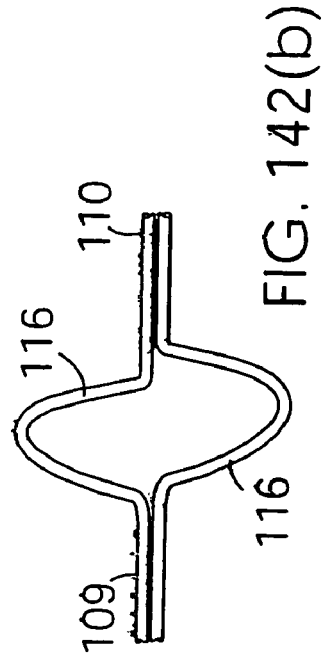
FIG. 142
FIG. 142(a)
FIG. 142(b)

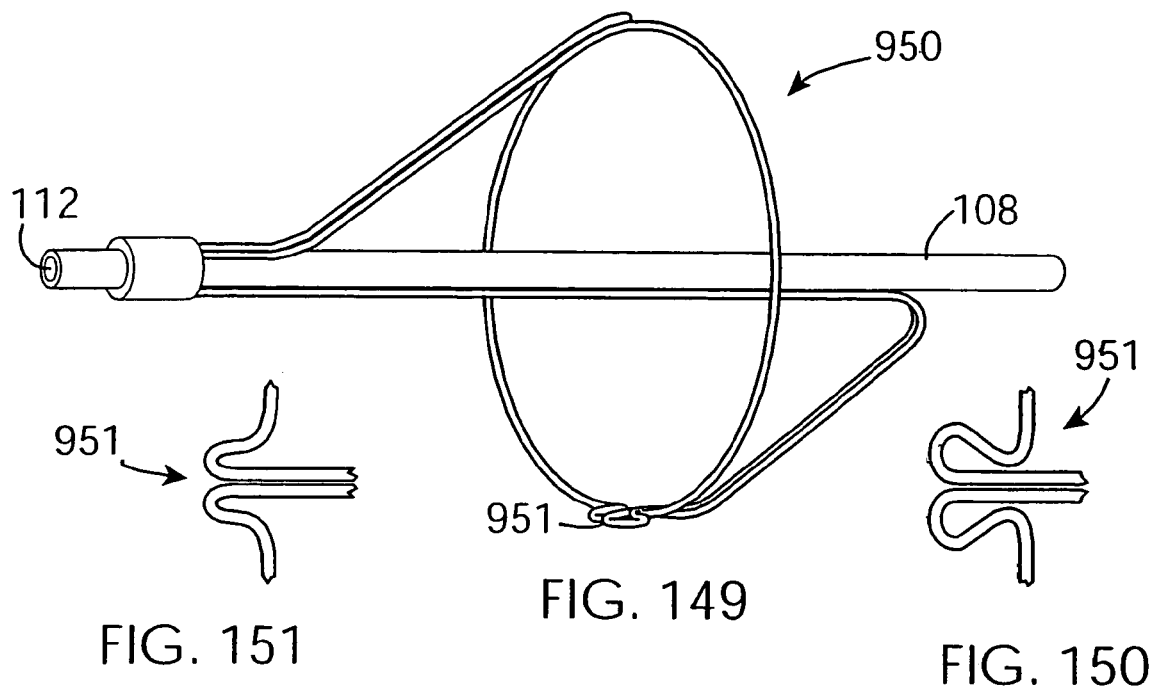
FIG. 149
FIG. 151
FIG. 150
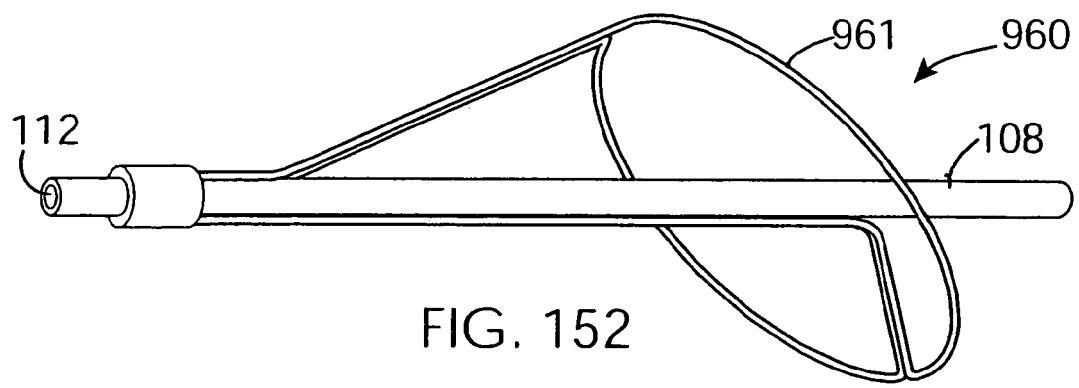
FIG. 152
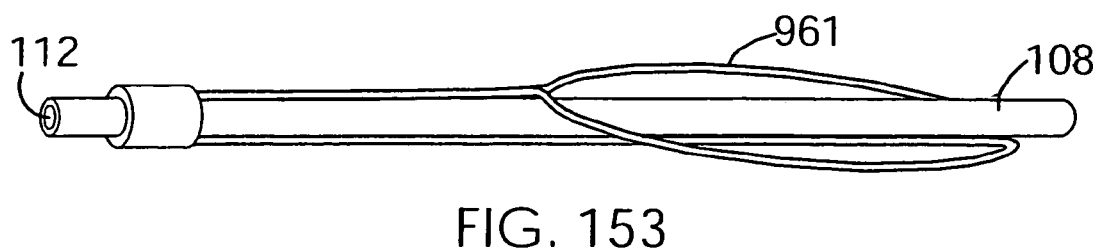
FIG. 153

SUPPORT FRAME FOR AN EMBOLIC PROTECTION DEVICE

CROSS REFERENCE TO RELATED APPLICATIONS

This application is a Continuation-In-Part of U.S. application Ser. No. 09/986,132, filed Nov. 7, 2001 now abandoned, which is a continuation of PCT/IE00/00054, filed May 8, 2000, and claims the benefit of U.S. Provisional Application Nos. 60/341,836, filed Dec. 21, 2001; 60/341,805, filed Dec. 21, 2001; 60/373,641, filed Apr. 19, 2002; 60/373,640, filed Apr. 19, 2002; and 60/377,248, filed May 3, 2002, the content of all of which, with the exception of international application no. PCT/IE00/00054, is incorporated herein by reference.

INTRODUCTION

This invention relates to an embolic protection device. In particular, it relates to an embolic protection device of the type comprising a collapsible filter body to capture embolic material, and a support to maintain the filter body in an expanded position when the embolic protection device is deployed in a vasculature.

Embolic protection devices of this general type are known.

However, there exist a number of problems with some of the known devices. In particular, upon collapse of the filter support, prior to delivery of the embolic protection device into and/or retrieval from a vasculature, large, localised stresses may be induced in the support. Solutions to this problem heretofore may result in features which inhibit the optimum performance of the device. In some systems flow paths for the blood can develop between the filter body and the interior wall of the vasculature. In general conventional devices are not highly trackable because of their length in the wrapped delivery configuration.

There is therefore a need for an embolic protection device which overcomes at least some of the disadvantages that exist with some of the known devices.

STATEMENTS OF INVENTION

According to the invention there is provided an embolic protection device comprising:

a collapsible filter element for delivery through a vascular system of a patient;

the filter element comprising a collapsible filter body and a filter support for the filter body;

the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;

the filter support being movable between a collapsed position for movement through the vascular system, and an extended outwardly projecting position to support the filter body in an expanded position;

the filter support comprising a number of segments at least some of which are interconnected by a strain distributing linking element.

In one embodiment at least some of the segments are of wire.

The linking element may be of wire. The linking element may be of the same wire as that of the support segments.

In one embodiment the linking element extends normally of adjacent segments. The linking element may extend longitudinally of the axis of the filter and/or the linking element extends radially inwardly of the adjacent segments.

In a preferred embodiment the linking element comprises a loop. The loop may be of generally omega shape.

In one embodiment at least portion of the linking element is radiopaque. Alternatively or additionally at least portion of at least some of the support segments are radiopaque.

In one embodiment the linking element is of multifilament construction. Alternatively or additionally at least one of the support segments is of multifilament construction.

In one embodiment the support frame is defined by at least two wire segments terminating distally, the distal terminations of adjacent segments being fixed relative to one another and extending generally parallel.

The support frame may be defined by at least two wire segments terminating proximally, the proximal terminations of adjacent segments being fixed relative to one another and extending generally parallel.

In one embodiment the support frame comprises a support arm for one end of the filter body which extends towards on opposite end of the filter body in the deployed configuration.

In one embodiment the device comprises a carrier extending longitudinally of the frame. The carrier may be a tubular member, sleeve or sleeves or may comprise a guidewire.

A flexible tether may extend between the carrier and the support frame.

In one embodiment the support frame comprises a support loop or hoop.

In another aspect the invention provides an embolic protection device comprising:

a collapsible filter element for delivery through a vascular system of a patient;

the filter element comprising a collapsible filter body and a filter support for the filter body;

the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;

the filter support being movable between a collapsed position for movement through the vascular system, and an extended outwardly projecting position to support the filter body in an expanded position;

the filter support comprising a support frame having at least two longitudinally spaced-apart segments which are interconnected by at least one flexible linking element.

The support frame segments may be of wire.

In a further aspect the invention provides an embolic protection device comprising:

a collapsible filter element for delivery through a vascular system of a patient;

the filter element comprising a collapsible filter body and a filter support for the filter body;

the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;

the filter support being movable between a collapsed position for movement through the vascular system, and an extended outwardly projecting position to support the filter body in an expanded position;

the filter support comprising a support frame defined by at least two wire segments having terminations, the terminations of adjacent segments being fixed relative to one another and extending generally parallel.

The wire segments may terminate distally, the distal terminations of adjacent segments being fixed relative to one another and extending generally parallel. Alternatively or additionally the wire segments terminate proximally, the proximal terminations of adjacent segments being fixed relative to one another and extending generally parallel.

The terminations may extend axially in relation to the filter. The distal terminations may be free to move axially. Alternatively or additionally the proximal terminations are free to move axially.

In one embodiment the proximal terminations of adjacent wire segments are configured to meet in a loop formation. The distal terminations of adjacent wire segments may be configured to meet in a loop formation.

In one embodiment the wire segments are of substantially the same length.

The wire segments may be fixed relative to one another by soldering, or welding, or bonding the wire segments to one another. Alternatively or additionally the device comprises a clamp around the wire segments to fix the wire segments relative to one another. The clamp may comprise a tubular sleeve. The clamp may comprise a clamp wire wound around the wire segments. The clamp may be at least partially of radiopaque material.

In one embodiment the wire segments are provided by a single wire bent back on itself.

Terminations may be located on an outer circumference of the filter frame. Alternatively or additionally terminations are located on an axis of the filter.

One of the proximal or distal terminations may be located on an outer circumference of the filter frame and the other of the proximal or distal terminations located on an axis of the filter.

In one embodiment each wire element has a circumferentially extending portion, and together the circumferentially extending portions of the wire elements define a cell which forms a substantially complete loop.

The wire elements may together define a number of cells axially spaced-apart. The support frame may have a connector between a first cell and a second cell.

The wire element may have an axially extending portion so that the cell partially slopes axially.

The wire element may extend in an irregular path such as in a substantially wave-like pattern.

In one embodiment the wire element extends in an arcuate path.

In one embodiment the filter support comprises at least one support leg extending radially inwardly from the support frame, the leg being defined by at least one wire. The cross-sectional area of the support leg may decrease radially inwardly.

In one embodiment at least part of the support leg is integral with at least part of the support frame. The support leg may be provided as an extension of one wire element and/or the support leg is provided as an extension of two or more adjacent wire elements.

In one embodiment the support leg extends at least partially distally inwardly from the support frame.

The wire element may have a round cross-section.

Alternatively, the wire element has an elongate cross-section with a long dimension and a short dimension. The short dimension of the wire element cross-section may be aligned substantially along the radial direction of the filter support. The wire element may be rectangular in cross-section.

In one embodiment the filter body comprises a flap wrappable around a wire element of the filter support to fix the filter body to the filter support.

In another aspect the invention provides a method of collapsing an embolic protection device for delivery and/or retrieval of the device through a vascular system, the method comprising the steps of:

providing an embolic protection device comprising a collapsible filter body and a filter support for the filter body; and collapsing the filter support to a low-profile configuration with an associated torqueing of at least part of the filter support upon elongation of the filter support.

In another aspect the invention, an embolic protection device, comprises:

a collapsible filter element for delivery through a vascular system of a patient;

the filter element comprising a collapsible filter body and a filter support for the filter body;

the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;

the filter support being movable between a collapsed position for movement through the vascular system, and an extended outwardly projecting position to support the filter body in an expanded position; the filter support comprising a support frame, a carrier, and a flexible tether extending between the carrier and the support frame.

In one embodiment the carrier extends longitudinally of the frame. The carrier may be a tubular member or sleeve(s). Alternatively the carrier is a guidewire.

The filter support may comprise a number of segments, at least some of which are interconnected by a strain distributing element.

The filter support may comprise a loop.

In one embodiment at least some of the segments are of wire. The linking element may be of wire. The linking element may be of the same wire as that of the support segments. The linking element may extend normally of adjacent segments, for example longitudinally of the axis of the filter and/or radially inwardly of the adjacent segments.

In one embodiment the linking element comprises a loop which may be of generally omega shape.

At least portion of the linking element may be radiopaque. At least some of the support segments may be radiopaque.

In one embodiment the linking element is of multifilament construction.

In another embodiment at least one of the support segments is of multifilament construction.

In one embodiment the support frame is defined by at least two wire segments having terminations, the terminations of adjacent segments being fixed relative to one another and extending generally parallel. The support frame may be defined by at least two wire segments terminating distally, the distal terminations of adjacent segments being fixed relative to one another and extending generally parallel. The support frame may be defined by at least two wire segments terminating proximally, the proximal terminations of adjacent segments being fixed relative to one another and extending generally parallel.

In one embodiment the support frame comprises a support arm for one end of the filter body which extends towards on opposite end of the filter body in the deployed configuration.

In one embodiment the device comprises a carrier extending longitudinally of the frame. A flexible tether may extend between the carrier and the support frame.

In one embodiment the support frame comprises a support loop.

In another aspect the invention provides an embolic protection device comprising:
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed position for movement through the vascular system, and an extended outwardly projecting position to support the filter body in an expanded position;
  the filter support comprising a support frame,
  a support arm for one end of the filter body which extends towards an opposite end of the filter body in the deployed configuration.

The support arm may be a proximal support arm that extends distally in the deployed configuration. Alternatively or additionally the support arm is a distal support arm that extends proximally in the deployed configuration.

In a further aspect the invention provides an embolic protection device comprising:
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed position for movement through the vascular system, and an extended outwardly projecting position to support the filter body in an expanded position;
  the filter support comprising a generally tubular support frame defined by at least one wire.

The at least one wire of the tubular support frame becomes torqued during collapse of the filter support. This torque induced upon collapse is evenly distributed along the wire without resulting in stress concentrations on the filter support. Thus, the wires may be of a small cross-sectional area which advantageously collapse down to a very low profile.

In addition, small wires enable greater flexibility for the filter element, which allow for ease of advancement through the vascular system.

The frame may comprise a number of cells, at least one of the cells defining a segment of a tube. Each cell may define a segment of a tube.

In one embodiment at least portion of an element of one cell is connected to an element of another cell. The connection means may be provided by an extension wire between the cells. At least portion of an element of one cell may be directly fixed to an element of another cell.

The or each cell may be defined by two wire elements. The two wire elements may be of substantially the same length. The or each wire element may have a proximal termination and a distal termination, and the proximal terminations of adjacent wire elements are fixed relative to one another, and/or the distal terminations of adjacent wire elements are fixed relative to one another.

The terminations of adjacent wire elements may extend generally axially and parallel. The proximal terminations may be circumferentially aligned with the distal terminations. Alternatively the proximal terminations are circumferentially offset from the distal terminations.

In one embodiment each wire element has an axially extending portion and a circumferentially extending portion.

In one embodiment at least one wire element has an S-shaped portion for distributed filter body support.

The wire elements may be provided by a single wire bent back on itself. The single wire may have a strain relief means at the bend in the wire. The wire may be treated to minimise stress at the bend in the wire.

In one embodiment the filter support comprises at least one support leg extending radially inwardly from the tubular support frame, the leg being defined by at least one wire. At least part of the support leg is integral with at least part of the tubular support frame. The support leg may extend distally inwardly from the support frame.

According to a further aspect of the invention, there is provided an embolic protection device comprising:
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed position for movement through the vascular system, and an extended outwardly projecting position to support the filter body in an expanded position;
  the filter support comprising a support frame defined by at least two wire elements, each wire element having a proximal termination and a distal termination, the terminations of adjacent elements extending generally axially and parallel.

According to the invention, there is provided a medical device having a collapsed configuration for transport through a body passageway, and an expanded configuration for deployment in a body;
  the medical device comprising a support movable from the collapsed configuration to the expanded configuration to support the medical device in the expanded configuration;
  the support comprising a radiopaque core.

The second moment of area of the radiopaque material is proportional to the fourth power of its diameter. Therefore because the radiopaque material is provided as the core of the support, this greatly reduces the diameter and thus the second moment of area of the radiopaque material. Correspondingly the forces required to facilitate deployment of the medical device are also greatly reduced.

In this manner the invention minimises the dampening effect of the radiopaque material on the medical device.

By locating the radiopaque material as the core of the support, this also results in a low-profile medical device.

In one embodiment of the invention the core is located substantially along the neutral axis of bending of the support.

Preferably the support comprises at least one support element. The support element may be of a superelastic material. Ideally the radiopaque core is provided as a core embedded within at least one support element. In one case the radiopaque core is in powder form. In another case the radiopaque core is in liquid form.

In a preferred embodiment the radiopaque core comprises a radiopaque element amongst a plurality of support elements. The element may comprise a wire. Ideally the elements are wound together.

The radiopaque core may be of mercury, or gold, or platinum.

In another aspect, the invention provides a medical device having a collapsed configuration for transport through a body passageway, and an expanded configuration for deployment in a body;

the medical device comprising a support movable from the collapsed configuration to the expanded configuration to support the medical device in the expanded configuration;

the support comprising a reservoir enclosing a fluid, the fluid being expandable upon an increase in temperature to bias the support to the expanded configuration.

According to a further aspect of the invention, there is provided a medical device having a collapsed configuration for transport through a body passageway, and an expanded configuration for deployment in a body;

the medical device comprising a support movable from the collapsed configuration to the expanded configuration to support the medical device in the expanded configuration;

the support comprising a reservoir enclosing a fluid, the fluid being pressurised to bias the support to the expanded configuration upon release of a constraint.

In one case the reservoir comprises an enclosed tube. The tube may extend at least partially circumferentially around the device. Ideally the ends of the tube meet to form an enclosed loop.

The fluid may be of a radiopaque material. Preferably the fluid is liquid mercury.

In a preferred embodiment of the invention the device is an intravascular medical device for transport through a vasculature and deployment in a vasculature. Most preferably the device is an embolic protection filter. Ideally the filter comprises a filter body supported by the support, the filter body having an inlet end and an outlet end, the inlet end of the filter body having one or more inlet openings sized to allow blood and embolic material enter the filter body, and the outlet end of the filter body having a plurality of outlet openings sized to allow through passage of blood but to retain undesired embolic material within the filter body.

According to the invention, there is provided a medical device having a collapsed configuration for transport through a body passageway, and an expanded configuration for deployment in a body;

the medical device comprising a support movable from the collapsed configuration to the expanded configuration to support the medical device in the expanded configuration;

at least part of the support being of a multifilament wire construction.

In the multifilament wire construction of the invention, each filament bends independently of the other filaments. Correspondingly, the overall force required to bend the support is a summation of the forces required to bend each filament. Because the force required to bend a wire is proportional to the fourth power of the diameter of the wire, the overall force required to bend the multifilament support is much less than the force which would be required to bend a single wire with the same overall diameter as the multifilament support.

In this manner, the medical device of the invention achieves enhanced trackability during transport through even tortuous body passageways, while ensuring the medical device is moved by the support from the collapsed configuration to the expanded configuration upon deployment in the body.

The multifilament wire construction also provides the medical device with greater deformability in the expanded configuration. This enables the medical device to adapt to the particular characteristics of the body passageway in which it is deployed.

In one embodiment of the invention at least one filament is wound around at least one other filament. By winding the filament, the bending stress induced in the filament is reduced. Preferably at least some of the filaments are braided together.

In a particularly preferred embodiment at least one filament is of a radiopaque material. The radiopaque nature of the filament provides visualisation of the medical device during transport through and deployment in a body. The radiopaque filament is ideally located substantially along the neutral axis of bending of the support.

In another case at least one filament may comprise a radiopaque core embedded within the filament.

In a further embodiment of the invention the support comprises a jacket around the filaments. The jacket helps to maintain the structure of the multifilament wire construction intact and ensure the filaments move in a coordinated manner. Preferably the filaments are embedded within the jacket. Ideally the jacket is at least partially of a radiopaque material. The jacket may be at least partially of a polymeric material.

Desirably the support is of the multifilament wire construction at a point of high curvature in the expanded support.

The device is preferably an intravascular medical device for transport through a vasculature and deployment in a vasculature. Ideally the device is an embolic protection filter. Most preferably the filter has an inlet end and an outlet end, the inlet end having one or more inlet openings sized to allow blood and embolic material enter the filter, and the outlet end having a plurality of outlet openings sized to allow through passage of blood but to retain undesired embolic material within the filter.

In a preferred case the filter comprises a filter body supported by the support, and the inlet openings and the outlet openings are provided in the filter body to retain undesired embolic material within the filter body. The filaments may define a mesh. Ideally the inlet openings and the outlet openings are provided by openings through the mesh.

BRIEF DESCRIPTION OF THE DRAWINGS

The invention will be more clearly understood from the following description of some embodiments thereof, given by way of example only, with reference to the accompanying drawings, in which:

FIG. 1 is a perspective view of an embolic protection device according to the invention;

FIGS. 2 and 3 are perspective views of a filter support of the embolic protection device of FIG. 1;

FIG. 4 is an end view of the filter support of FIGS. 2 and 3;

FIG. 46 is a perspective view of a support frame of the invention;

FIG. 47 is an end view in the direction of the arrow A in FIG. 46;

FIGS. 48 to 51 are views similar to FIGS. 46 and 47 of further support frames;

FIG. 63 is a perspective view of portion of a frame element or a linkage element;

FIG. 64 is a perspective view of the element of FIG. 63, in use;

FIGS. 65 and 66 are perspective views of alternative frame elements or linkage elements;

FIG. 67 is a perspective view of portion of another frame element or linkage element of the invention;

FIG. 68 is a perspective view of the element of FIG. 67, in use;

FIGS. 78 to 81 are perspective views of portions of other frame elements or linkage elements;

FIG. 82 is a perspective view of a support frame of the invention;

FIG. 83 is a perspective view of another support frame of the invention;

FIGS. 87 to 99 are perspective views of various support frames of the invention, most of which include tether elements;

FIG. 106 is a perspective view of another embolic protection device;

FIG. 107 is a perspective view of another support frame;

FIG. 142 is a perspective view of a support frame of the device of FIG. 141;

FIG. 142(a) is a detail view of portion of the support frame of FIG. 142(b);

FIG. 142(b) is a plan view of an offset variant of the support frame of FIG. 142;

FIG. 149 is a perspective view of another support frame;

FIG. 150 is a view of a detail of the frame of FIG. 149;

FIG. 151 is a view of an alternative detail of the frame of FIG. 149;

FIG. 152 and FIG. 153 are views of the frame of FIG. 149 being wrapped down;

DETAILED DESCRIPTION

Figure 5:
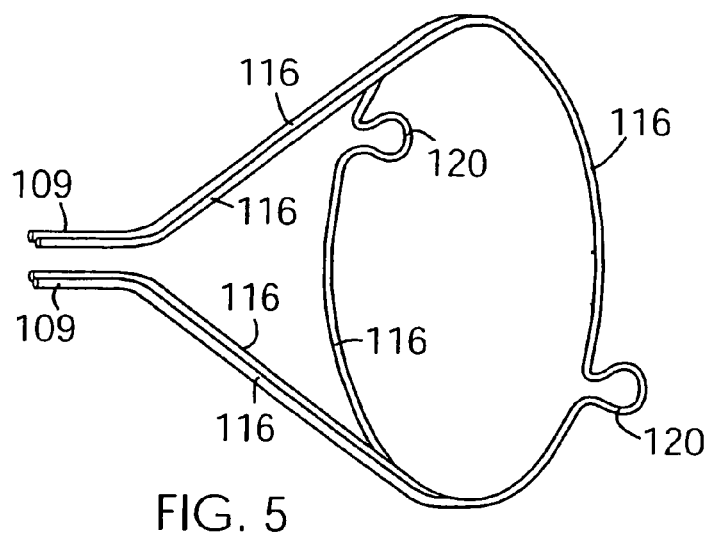
FIGS. 5 to 7 are perspective views illustrating collapse of the filter support of FIGS. 1 to 4.

Referring to the drawings, there are illustrated several embolic protection devices according to the invention. In general the embolic protection devices comprise a collapsible filter element for delivery through a vascular system of a patient. The filter element comprises a collapsible filter body 102 and a filter support 103 for the filter body 102, and a carrier which may comprise a tubular member 108 to which the filter support 103 may be mounted.

The filter body 102 has an inlet end 104 and an outlet end 105. The inlet end 104 has one or more large inlet openings 106 which are sized to allow blood and embolic material enter the filter body 102. The outlet end 104 has a plurality of small outlet openings 107 which are sized to allow through passage of blood but to retain undesired embolic material within the filter body 102. In this way, the filter element captures and safely retains any undesired embolic material in the blood stream within the filter body 102 while facilitating continued flow of blood through the vascular system. Emboli are thus prevented from flowing further downstream through the vascular system, which could otherwise have potentially catastrophic results.

The filter body 102 may be of an oriented polymeric material, as described in WO 01/97714A and US 2002/0042627A, the relevant contents of which are incorporated herein by reference.

The filter support 103 is movable between a low-profile, collapsed position for movement through the vascular system, and an extended outwardly projecting position. In this outwardly projecting position, the filter body 102 is supported in an expanded position by the filter support 103, so as to maximise the internal volume of the filter body 102 to capture and safely retain as much embolic material as possible. The inner tube 108 has a guidewire lumen 112 therethrough, through which a guidewire may pass for exchange of the filter element 1 over the guidewire. Alternatively, in all embodiments the carrier may comprise a guidewire.

One embolic protection device 100 according to the invention is illustrated in FIGS. 1 to 9. A proximal end of the filter support 103 may be fixed to the inner tube 108. Upon collapse of the filter element, the proximal end of the filter support 103 may remain fixed relative to the inner tube 8, and the filter support 103 collapses distally against the inner tube 108. In this collapsed position, the filter support 103 is axially elongated relative to the expanded position.

The filter support 103 in this case comprises two round wires 116 which extend from the proximal end 109. The wires 116 extend together axially and radially outwardly in a leg 118 from the proximal end 109, where the wires 116 are fixed to the inner tube 108. The junction of the leg 118 with the support hoop is referred to in this specification as the proximal termination point 119.

At a proximal termination point 119, the wires 116 separate, and extend circumferentially around to form support hoops.

This arrangement of the circumferential hoop formed by the wires 116 ensures that in the expanded position, the filter body 102 will be supported by the support frame 103 in circumferential apposition with the interior wall of the vasculature.

The length of each wire 116 around the hoop is equal. At the proximal termination point 19, the wires 116 are fixed to each other, and extend generally axially and parallel in a bi-filar arrangement.

As the filter support 103 collapses down against the inner tube 108, the wires 116 become torqued. This torqueing action is similar to the process of elongation of a coiled spring. Because the support frame 103 is defined by round wires 116, the torque developed in each wire 116 will be evenly distributed along the length of each wire 116. In addition, the bi-filar connection of the wires 116 to each other at the termination point 19, further assists in torque distribution along the wires 116. Thus, collapse of the filter support 103 does not induce high, localised stresses in the filter support 103. In this way, the filter support 103 may be constructed of wires 116 of a small cross-sectional area which will collapse down to a very low profile. Furthermore, the collapsed filter element with small wires 116 has greater flexibility for ease of advancement of the filter element 1 through the vascular system.

The wires 116 are preferably of a self-expanding material, such as Nitinol.

Figure 8A:
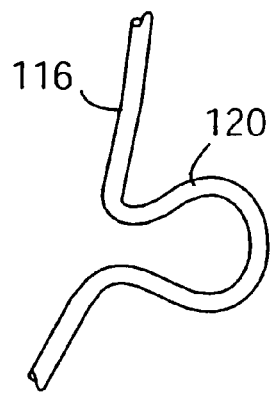
FIG. 8a is an enlarged view of part of the filter support of FIG. 5.
Figure 6:
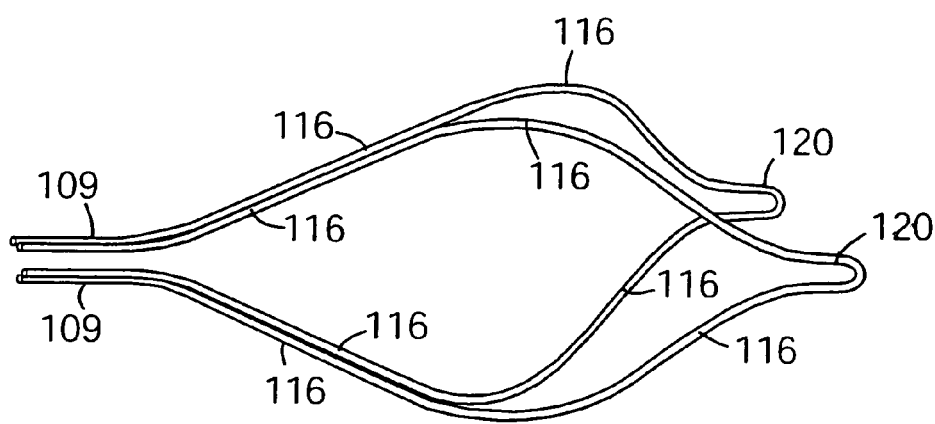
Figure 8B:
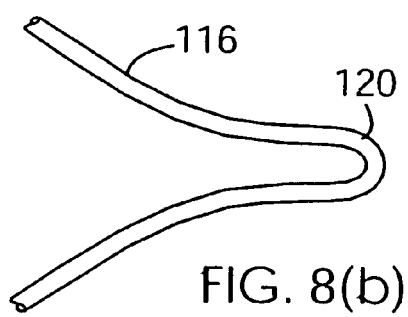
FIG. 8b is an enlarged view of part of the filter support of FIG. 6.
Figure 7:
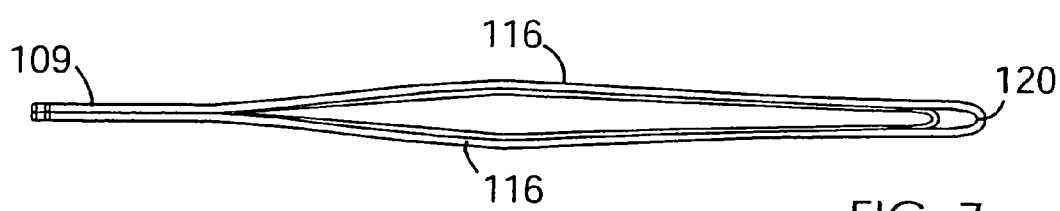
Figure 9:
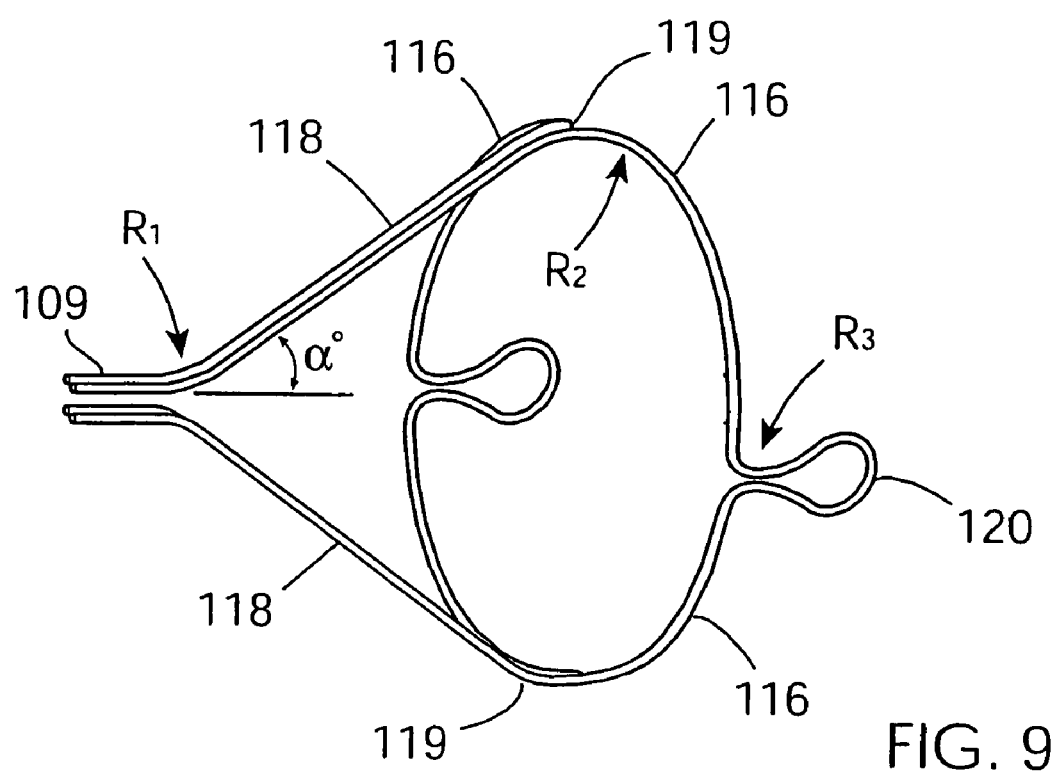
FIG. 9 is a perspective view of the filter support of FIGS. 1 to 7.

The wires 116 may have a strain distributing linkage element. In this case the linkage element comprises a loop 120 in each wire. The loop 120 in this case extends axially and distally of the wire hoop. The loop 120 is of generally omega shape as illustrated and is formed integrally in a wire 116. The loop 120 acts as a strain reliever or distributor when the wires 116 are wrapped down as illustrated in FIGS. 6, 7 and 8(*b*). The loop 120 has a relatively large radius resulting in highly efficient strain distribution. Radii R1, R2, R3 are provided at key points in the support frame to relieve strain as illustrated in FIG. 9. In addition, the loop 120 allows the support frame to accommodate varying vessel contours and sizes. In effect the loop 120 acts as a diameter or circumference adjuster allowing an embolic protection device to adapt to difference vessel contours and sizes whilst maintaining apposition with the vessel wall. The strain relieving geometry of the loops enhances the compliance of the bend points without creating a weakened hinge point, thus ensuring that there is no discontinuity in the circumferential seal against the vessel wall.

The loops 120 can also be regarded as distal termination points which have a pair of arms which extend axially and generally parallel. The looped terminations 120 enhance the ability of the filter support 103 to be wrapped down to a low profile.

In addition, the looped configuration of the distal termination 120 spreads the force exerted by the filter support 103 on the filter body 102 over a greater area. In this way, the local pressures applied by the filter support 103 on the filter body 102 and the walls of a vasculature are more evenly distributed, this minimising the possibility of vessel trauma.

Another important advantage of the strain distributing features such as loops 120 is that they provide an anchor to which connecting elements such as tethers may be readily attached as described in more detail below.

In use, the filter element is collapsed down and loaded into a delivery catheter with an associated torqueing of the wires 116 around the hoop. The filter element is then delivered through a vasculature fixed to or over a guidewire using the delivery catheter until the filter element is located at a desired site in the vasculature.

By moving the delivery catheter proximally relative to the filter element 1, the element is deployed out of the delivery catheter at the desired site in the vasculature. The filter support 103 expands radially outwardly to support the filter body 102 in circumferential apposition with the interior wall of the vasculature. In the fully expanded position, the wires 116 of the support frame 103 are substantially free of torque.

The site of deployment of the filter element in the vasculature is typically downstream of a treatment site, such as a region of stenosis in the vasculature. During the performance of a treatment procedure, the filter element captures and safely retains any embolic material in the blood stream within the filter body 102.

After completion of the treatment procedure, the filter element is collapsed down and retrieved into a retrieval catheter with any retained embolic material within the filter body 2. The wires 116 around the support frame 103 are again torqued during collapse. The retrieval catheter is then withdrawn from the vasculature with the filter element within the retrieval catheter.

The delivery, deployment and retrieval of the embolic protection device of the invention, as described above, is similar to the described in our WO 99/23976, WO01/80776A (US 2002-0052626A) and WO01/80773A (US 2002-0049467A), the relevant contents of which are incorporated herein by reference. The filter element may be slidably exchanged over the guidewire without any attachment means between the filter element and the guidewire. A distal stop on the guidewire assists in retrieval of the filter element. The guidewire may remain in the vasculature after retrieval of the filter element.

The support comprises a segmented ring structure which may have two circumferential wire segments. The wire segments may be connected by a strain distributing linkage element at one end and by a bifilar joint at the other end. The bifilar joint may be coupled to the carrier by a single or multiple struts and/or tethers. In one case the strut is attached to the carrier. The connection may permit rotation relative to the carrier either longitudinally distal or proximal to the point of attachement to the segmented ring.

In some cases the attachment to the carrier is rigid, in other cases a flexible joint is provided using a tether, a loop, a thinned wire section or the like. A focal tether may be utilised. A focal tether implies that the strut has tensile and compressive integrity bu the joint is not rigid. The joint can thus flex in all directions but it cannot translate.

Individual wires may taper towards the proximal or distal end.

The support frames may have distal, proximal and/or intermediate anchors. One anchor may be fixed and another translatable and/or rotatable relative to the carrier. For example a proximal anchor may be translatable or in arrangements in which both proximal and distal anchors are provided both may be translatable.

The support frame may comprise a segmented ring or hoop which may have an elliptical cross-section in the free expanded state. The support ring may be angulated relative to the axis of the inner member.

Figure 10:
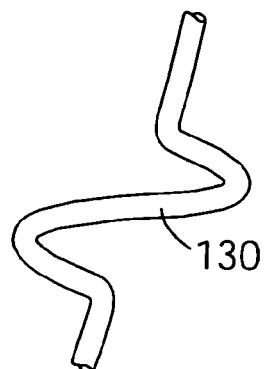
FIGS. 10 to 20 are views of various alternative strain distributing linkage elements.
Figure 11:
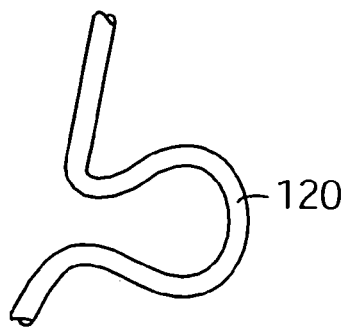
Figure 12:
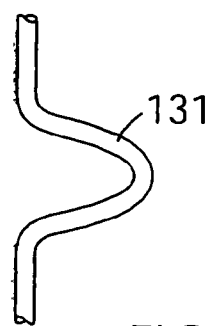
Figure 13:
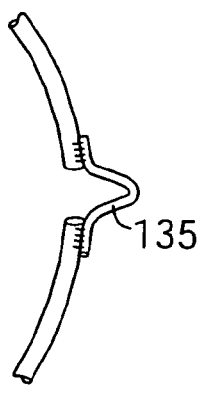
Figure 14:
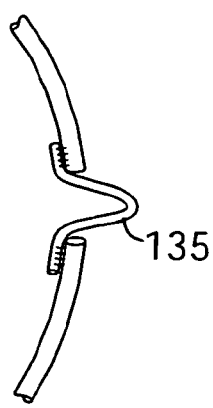
Figure 15:
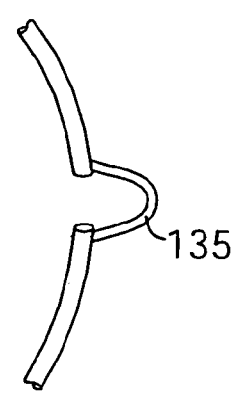
Figure 16:
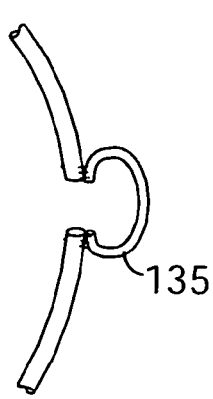
Figure 17:
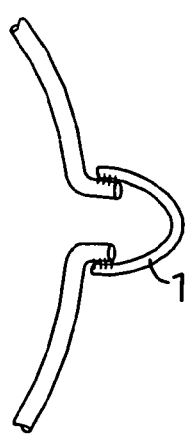
Figure 20:
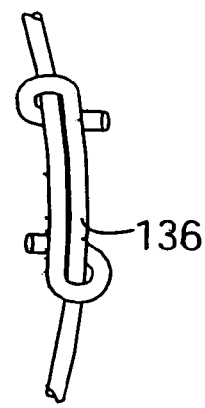

Various strain distributing linkage elements are illustrated in FIGS. 10 to 20. In FIG. 10 the strain distribution is provided by a zig zag linkage element 130. The omega shape of the preferred loop 120 will be apparent in FIG. 11 however the loop may approximate to a curved V shape 131 as illustrated in FIG. 12. Various arrangements in which a strain distributing element is provided by a separate component defining a loop 135 are illustrated in FIGS. 13 to 19. The loops 135 may be attached or formed in a number of ways, as illustrated. Another strain distributing diameter/adjusting feature 136 is illustrated in FIG. 20.

Figure 21:
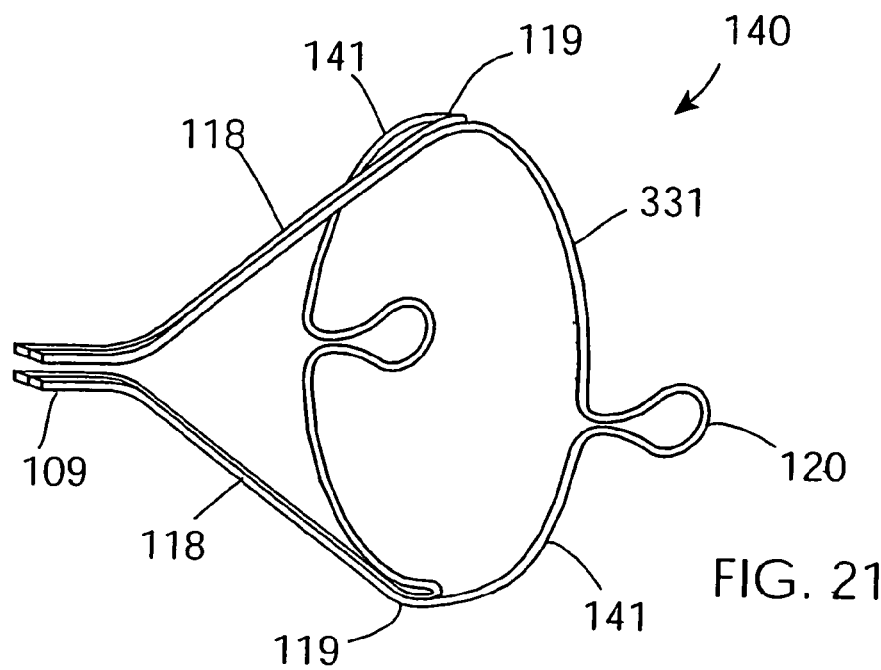
FIG. 21 is a perspective view of another filter support.
Figure 22:
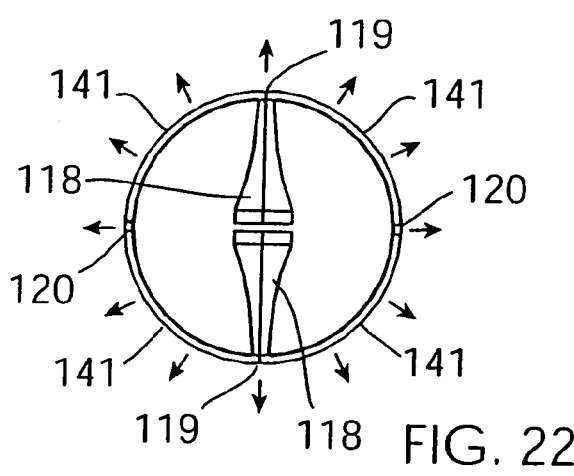
FIG. 22 is an end view of the filter support of FIG. 21.

Referring to FIGS. 21 and 22, there is illustrated a further filter support 140, which is similar to the filter support of FIGS. 1 to 9, and similar elements in FIGS. 21 and 22 are assigned the same reference numerals. In this case the filter support 140 comprises two wires 141 which have an elongate cross-section, in this case a rectangular cross-section, along their proximal section 118. The wires 141 are arranged such that the shorter dimension of the rectangle is aligned along the radial direction of the filter support, as illustrated in FIG. 22.

This flattened wire configuration provides for a filter support 140 with enhanced flexibility. This is achieved because the second moment of area of the wires 118 is reduced in the flattened configuration.

In addition, the flattened wires 141 minimise the influence of the support leg 118 on the outward radial force R1 exerted by the support frame. This results in a filter support 140 which exerts a relatively constant outward radial force R1 around the circumference of the filter support (FIG. 22).

Figure 24:
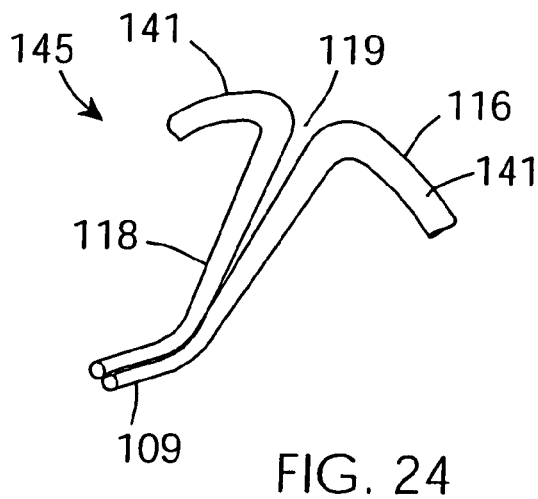

In FIG. 24, there is illustrated a filter support 145 in which the cross-sectional area of the round wire 141 decreases radially inwardly along the support leg 118 from the proximal termination point 119 to the proximal end of the filter support 145. This tapered support leg 118 also achieves the enhanced flexibility, and the relatively constant outward radial force R1 around the circumference of the filter support 145, similar to that discussed previously with reference to FIGS. 21 and 22.

Figure 23:
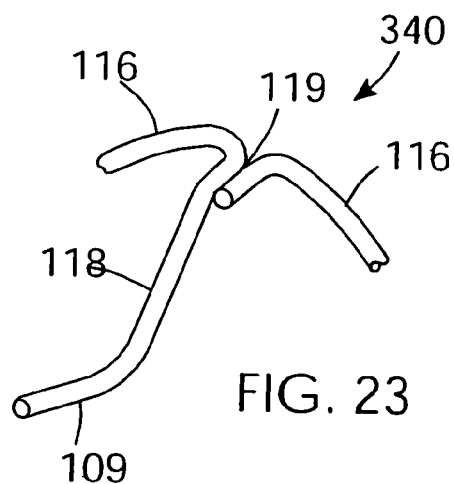
FIGS. 23 to 25 are perspective views of part of other filter supports.
Figure 25:
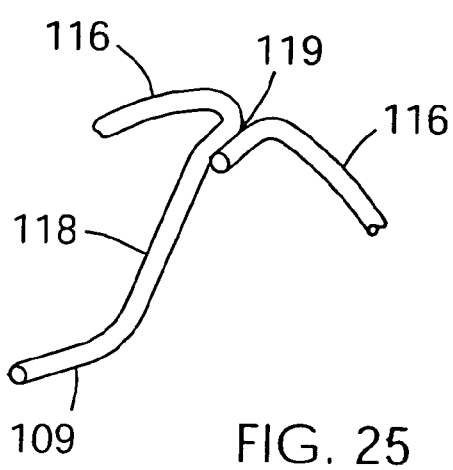

As illustrated in FIG. 23, the support leg 118 may be provided by only one of the two round wires 116, with the other round wire 116 terminating at the proximal termination point 119 where the wires 16 are fixed together. Another arrangement of this type is illustrated in FIG. 25.

The configuration of a single wire support leg 118 also achieves the enhanced flexibility, and the relatively constant outward radial force R1 around the circumference of the filter support 340, similar to that discussed previously with reference to FIGS. 21 and 22.

Figure 26:
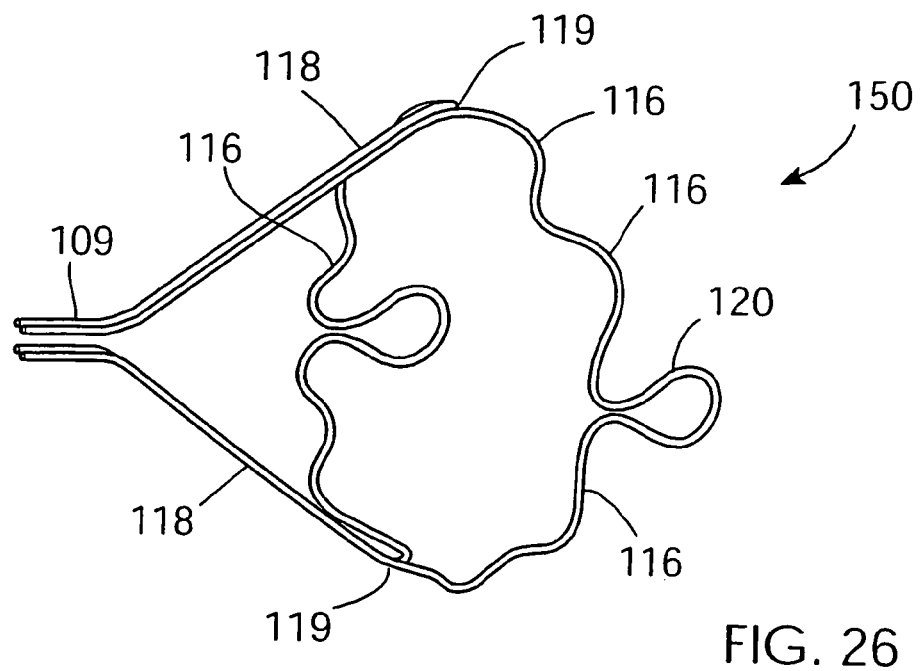
FIG. 26 is a perspective view of a further filter support.
Figure 27:
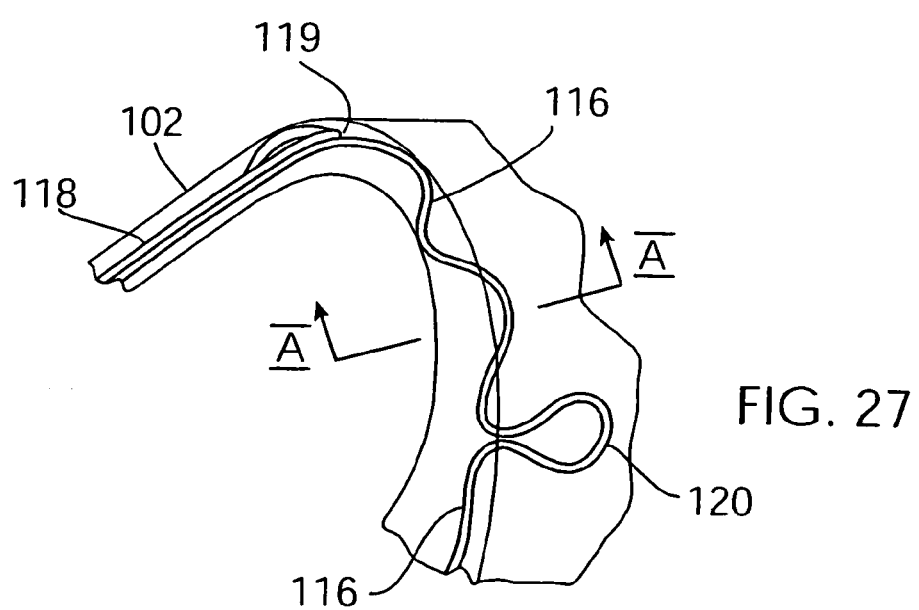
FIG. 27 is a perspective view of part of the filter support of FIG. 26 in use.
Figure 28:
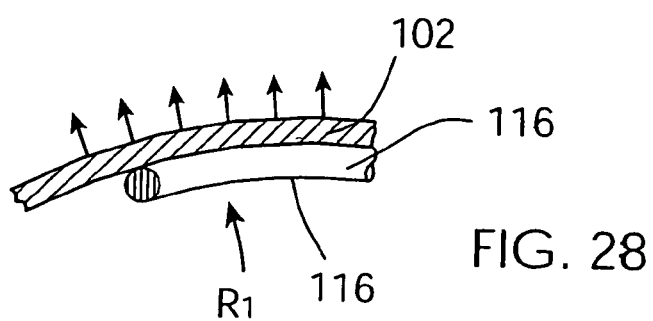
FIG. 28 is a view along line A—A in FIG. 27.

FIGS. 26 to 28 illustrate another filter support 150, which is similar to the filter support described above, and similar elements are assigned the same reference numerals. In the filter support 150, the round wires 116 extend circumferentially around the support frame in an irregular, wave-like pattern. This configuration increases the area of contact between the wires 116 and the filter body 102. As illustrated in FIG. 28 this increased area of contact assists in more evenly distributing the radial forces R1 from the support wires 116 to the filter body 102 and hence to the vessel wall. In this way, the risk of vessel trauma due to the forces exerted by the filter support 150 is minimised.

The radial forces exerted by the filter support on the filter body 102 and the walls of a vasculature depend on a number of factors, such as the diameter of the round wires 116, the material chosen for the wire 116 and the properties of that material, the number of wires 116 in the filter support, the angle of inclination a of the support leg 118 (FIG. 9), and the radii R1, R2, R3 of the bends in the filter support. By suitably varying these factors, the radial force exerted by the filter support 301 may be accurately controlled.

Another important influencing factor on the radial force exerted by the filter support is the fixing of the wires 116 relative to one another at the proximal termination points 119 and/or at the distal termination points 120. It may be advantageous to securely fix the wires 116 relative to one another at the proximal termination point 119 to achieve the required radial force perpendicular to the proximal termination point 119.

Figure 29:
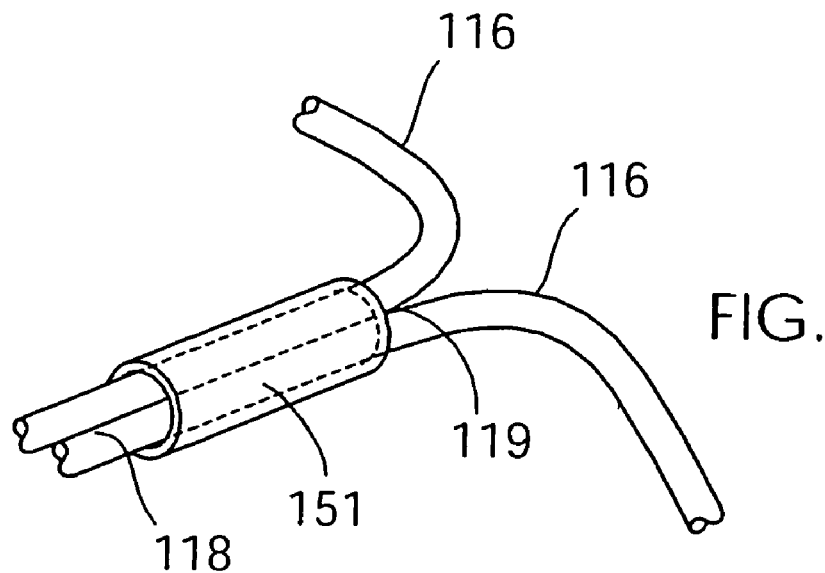
FIGS. 29 and 30 are enlarged perspective views of part of other filter supports.

One means of fixing the two wires 116 of the filter support relative to one another at the proximal termination point 119 is to clamp the wire 116 together using a tubular polymeric sleeve 151, as illustrated in FIG. 29. The sleeve 151 provides a durable means of fixing the wires 116 together which will effectively resist peeling of the wires 116 apart, thus resulting in a highly robust filter element.

The sleeve 151 may be partially of a radiopaque material, such as platinum, or iridium, to provide visualisation of the filter element during use.

Figure 30:
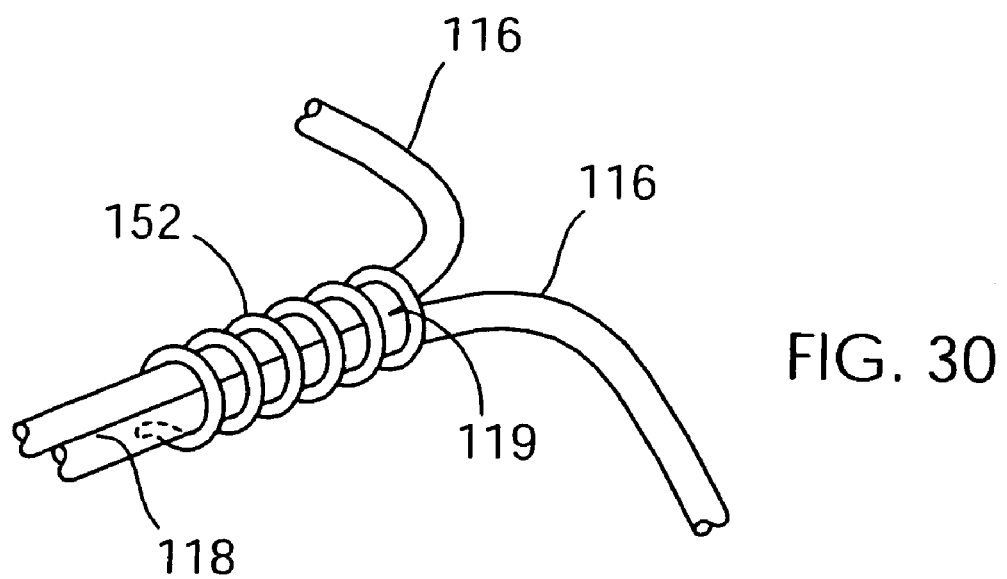

Alternatively the wires 116 may be clamped together by winding a wire 152 around the support wires 16, and then bonding or soldering the wire 152 in place around the clamped support wires 16, as illustrated in FIG. 30. The wire 152 may be radiopaque.

Another suitable means of fixing the two wires 116 together is to directly solder, weld or bond the tow wires 116 together.

It will be appreciated that a variety of different means may be used to effectively fix the wires 116 relative to one another at the proximal termination point 119 and/or at the distal termination point 120.

Figure 32:
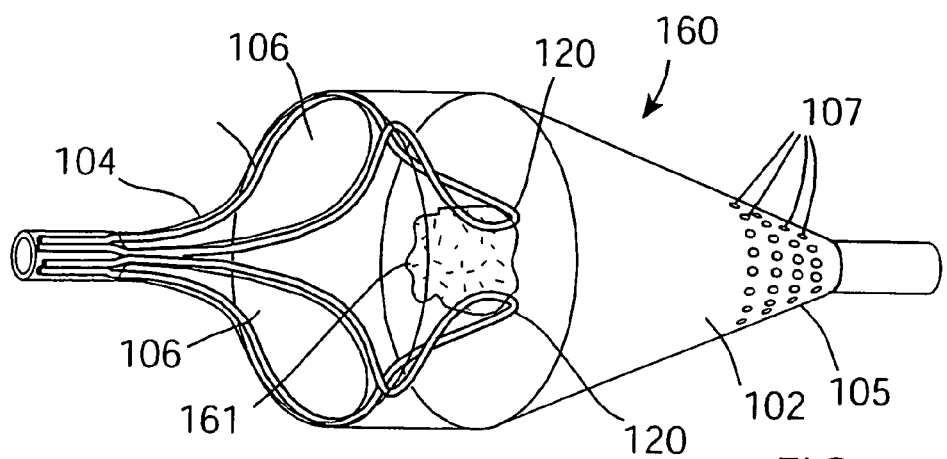
FIG. 32 is a perspective view of the device of FIG. 31, in use.
Figure 31:
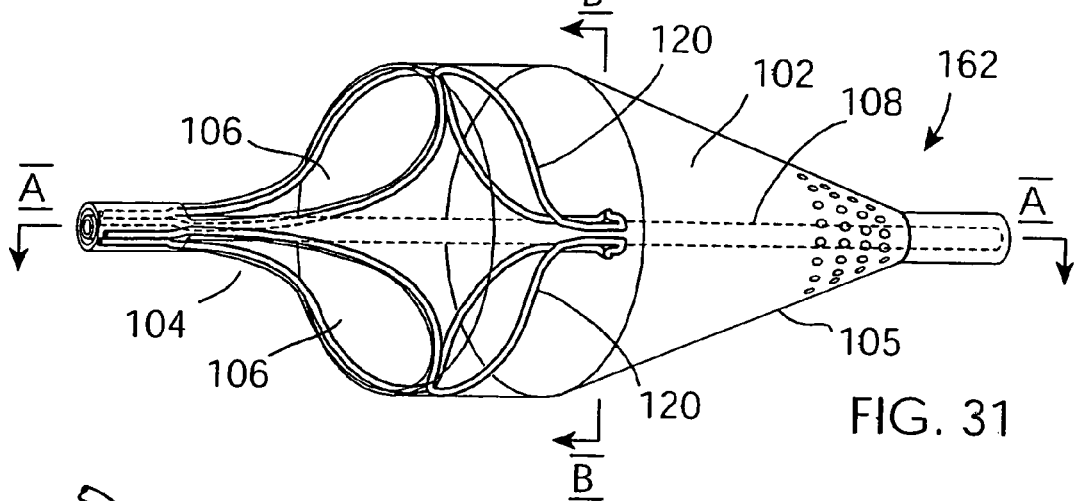
FIG. 31 is a perspective view of another device of invention.
Figure 33:
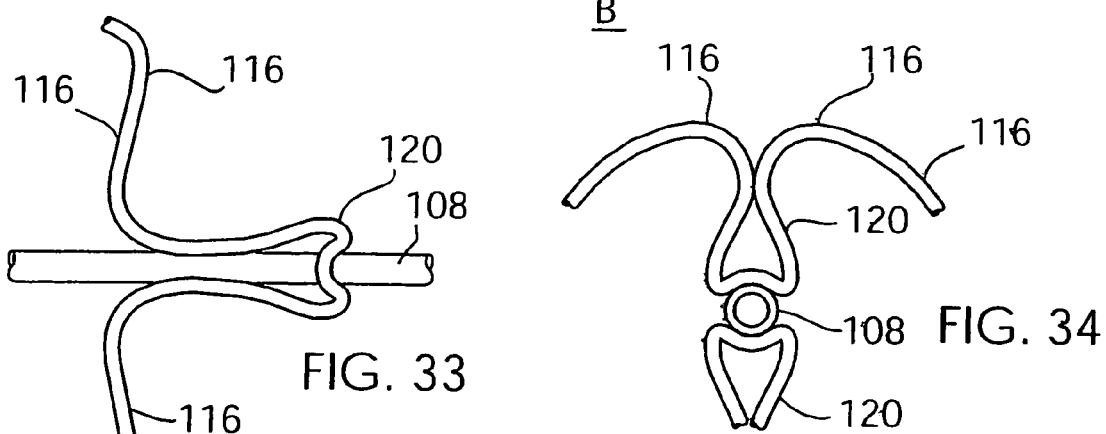
FIG. 33 is a cross sectional view on the line A—A in FIG. 31.
Figure 34:
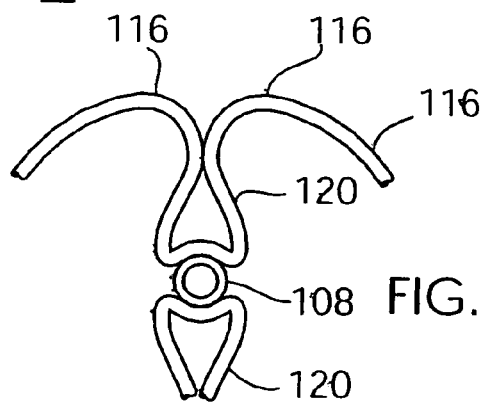
FIG. 34 is a cross sectional view on the line B—B in FIG. 31.

As illustrated in FIG. 32, the looped termination 120 may be configured to fold radially inwardly upon collapse of the filter 160, so that the looped termination 120 will engage emboli 161 which have collected in the filter body 102. In this manner, the looped terminations 120 will assist in holding the emboli 161 in place within the filter body 2 and in preventing extrusion of the emboli 161 out of the filter body 102 during retrieval of the filter 160. Thus the filter 160 will safely retain the emboli 161 for removal from the vasculature.

Furthermore, as illustrated in FIGS. 31 to 35, the looped termination 120 may be folded radially inwardly to engage against the inner tube 108. This arrangement provides enhanced radial support for the filter body 102.

Upon collapse of the filter 162, the looped terminations 120 slide over the inner tube 108 until the filter support is in the fully collapsed, elongated configuration.

Figure 35:
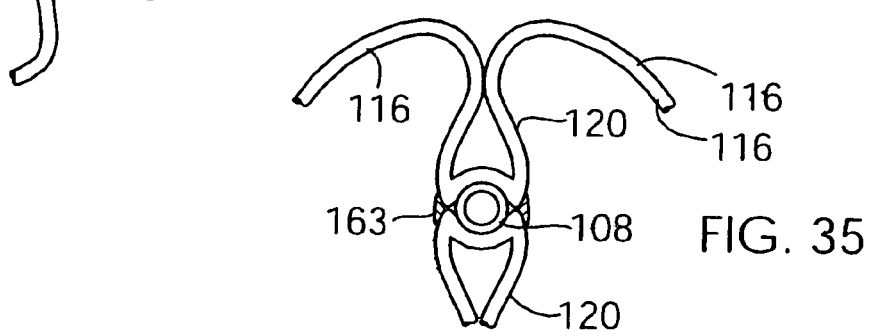
FIG. 35 is a cross sectional view similar to FIG. 34 of an alternative embolic protection device.

The loops 120 may be attached at 163 to constrain their freedom of movement to the axis of the tube 108 (FIG. 35)

Figure 36:
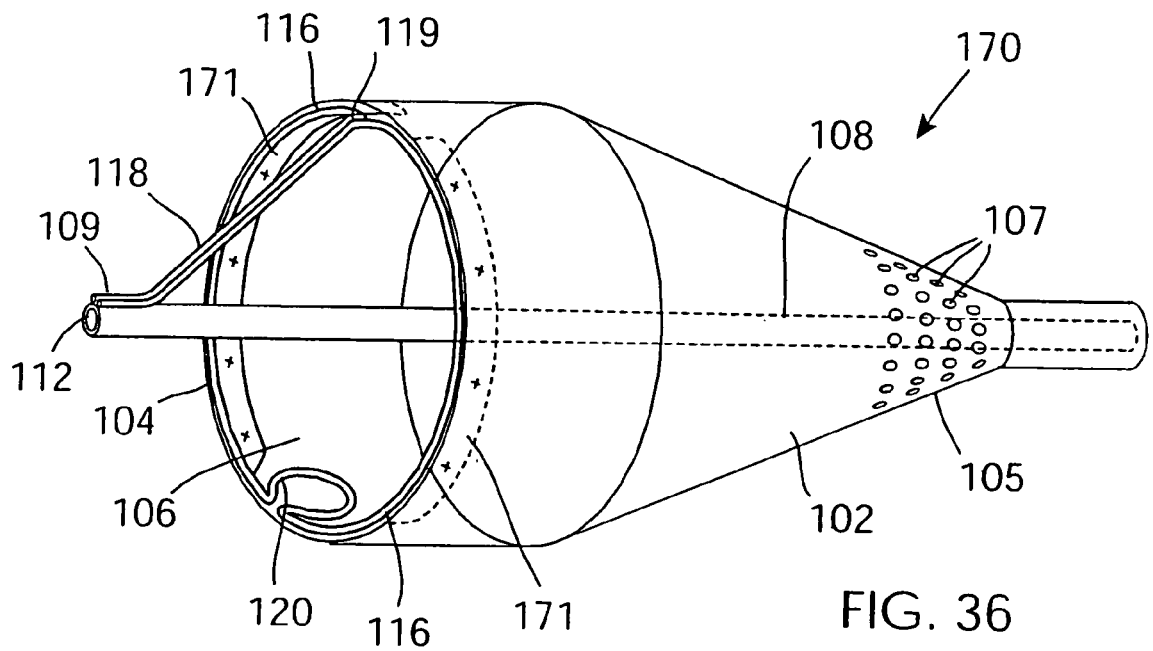
FIGS. 36 and 37 are perspective views of other embolic protection devices according to the invention.

Another filter 170, is illustrated in FIG. 36, and similar elements to those in previous drawing are assigned the same reference numerals. The filter support comprises a single round wire 116 which extends axially and radially outwardly in a single leg 118 to the proximal termination point 119. The wire 116 extends circumferentially around the support frame, looping at the distal termination 120.

The filter body 102, has a single, large inlet opening 106 defined at the inlet end 104. This arrangement further minimises the possibility of any enbolic material becoming caught or hung-up on any parts of the filter at the inlet end 104. This arrangement also further reduces the overall longitudinal length of the filter 170.

In this case the filter body 102 is fixed directly to the filter support at the inlet end 104 by wrapping two flaps 171 of the filter body 102 around the support wires 116 and then fixing the flaps 171 to the filter body 102 in this wrapped position (FIG. 36).

Figure 37:
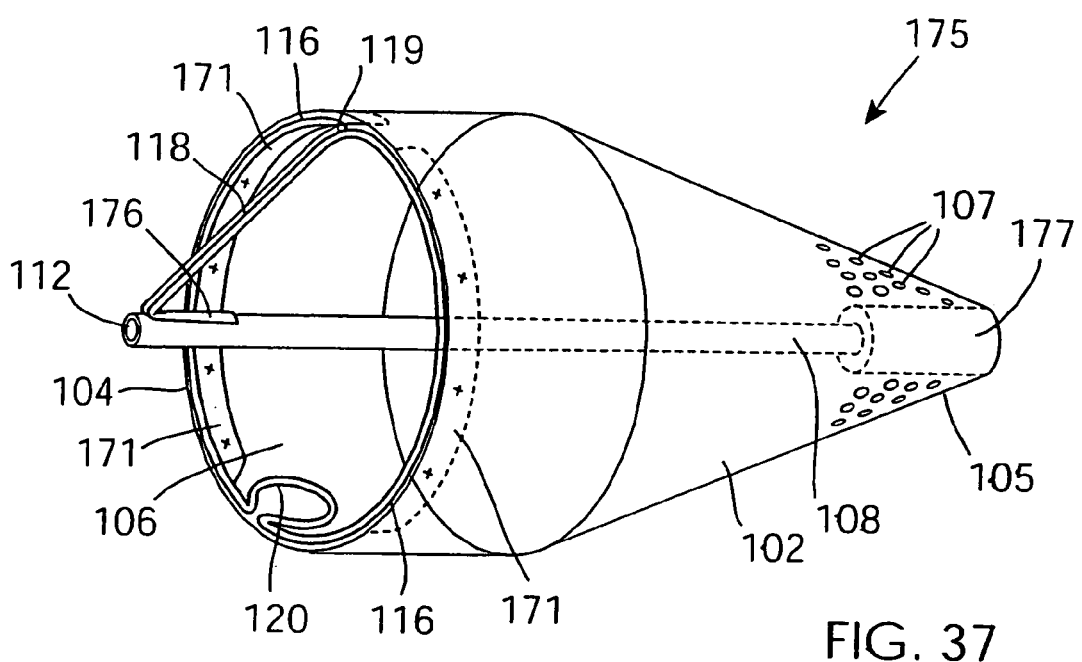

In the filter element 175 of FIG. 37, the support leg 118 is fixed to the inner tube 108 at an inner foot section 176. The inner section 176 is inverted to extend distally along the inner tube 108. In addition, the filter body 102 is configured to slide distally over the inner tube 108 upon collapse by means of a sleeve 177 fixed to the filter body 102 at the distal end 105. The sleeve 117 is also inverted to extend proximally along the inner tube 108.

In this way, by inverting the inner section 176 of the leg 118 and the sleeve 177, the overall longitudinal length of the filter support is minimised. This results in less "parking space" in a vasculature being required to deploy the filter.

Furthermore, by extending the inner section 176 of the leg 118, distally, the possibility of embolic material becoming caught or hung-up at the inlet end 104 of the filter element is reduced.

Figure 38:
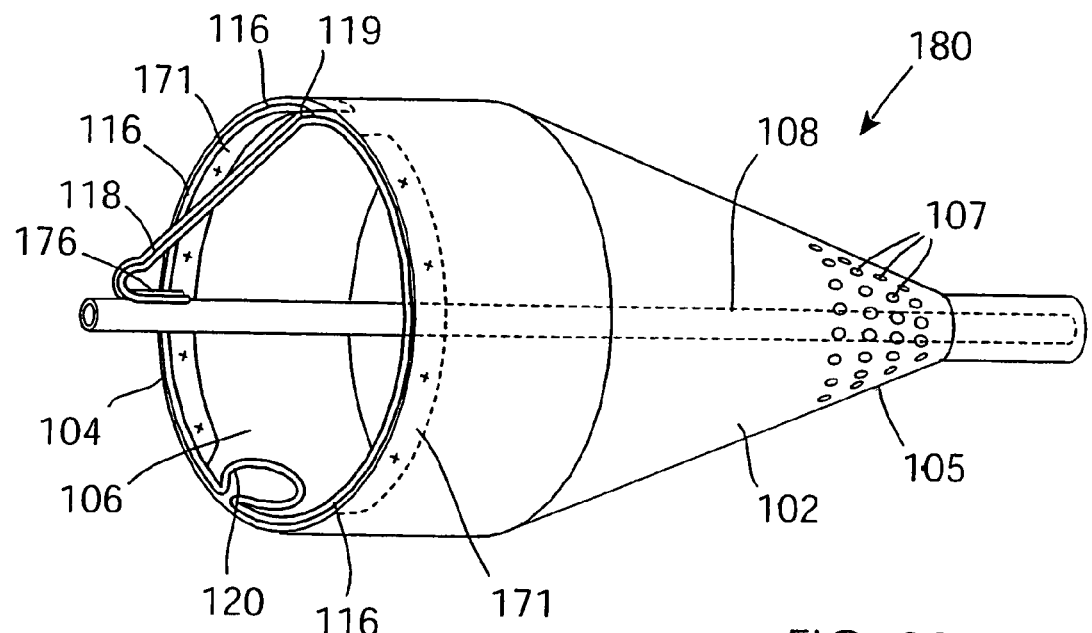
FIG. 38 is a perspective view of another embolic protection device.

Referring to FIG. 38 another filter 180 which has a more enhanced transition to the foot 176 is illustrated.

Figure 39:
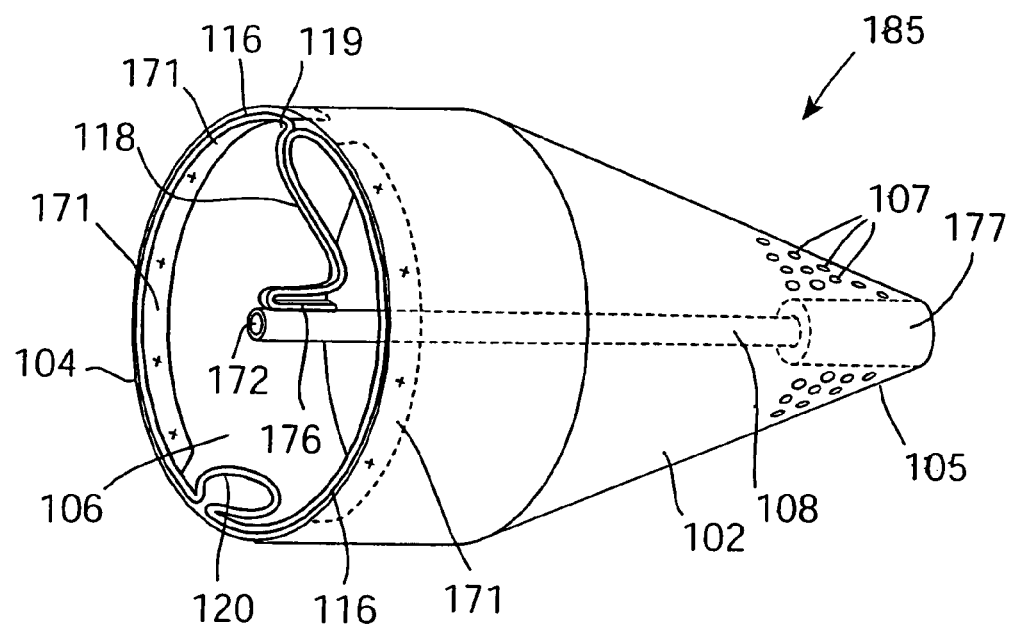
FIG. 39 is a perspective view of an embolic protection device.

The filter 185 of FIG. 39 has a proximal support leg 118 that extends distally to minimise the length and hence the parking space of the filter. A support foot 176 is again provided for load distribution.

Figure 140:
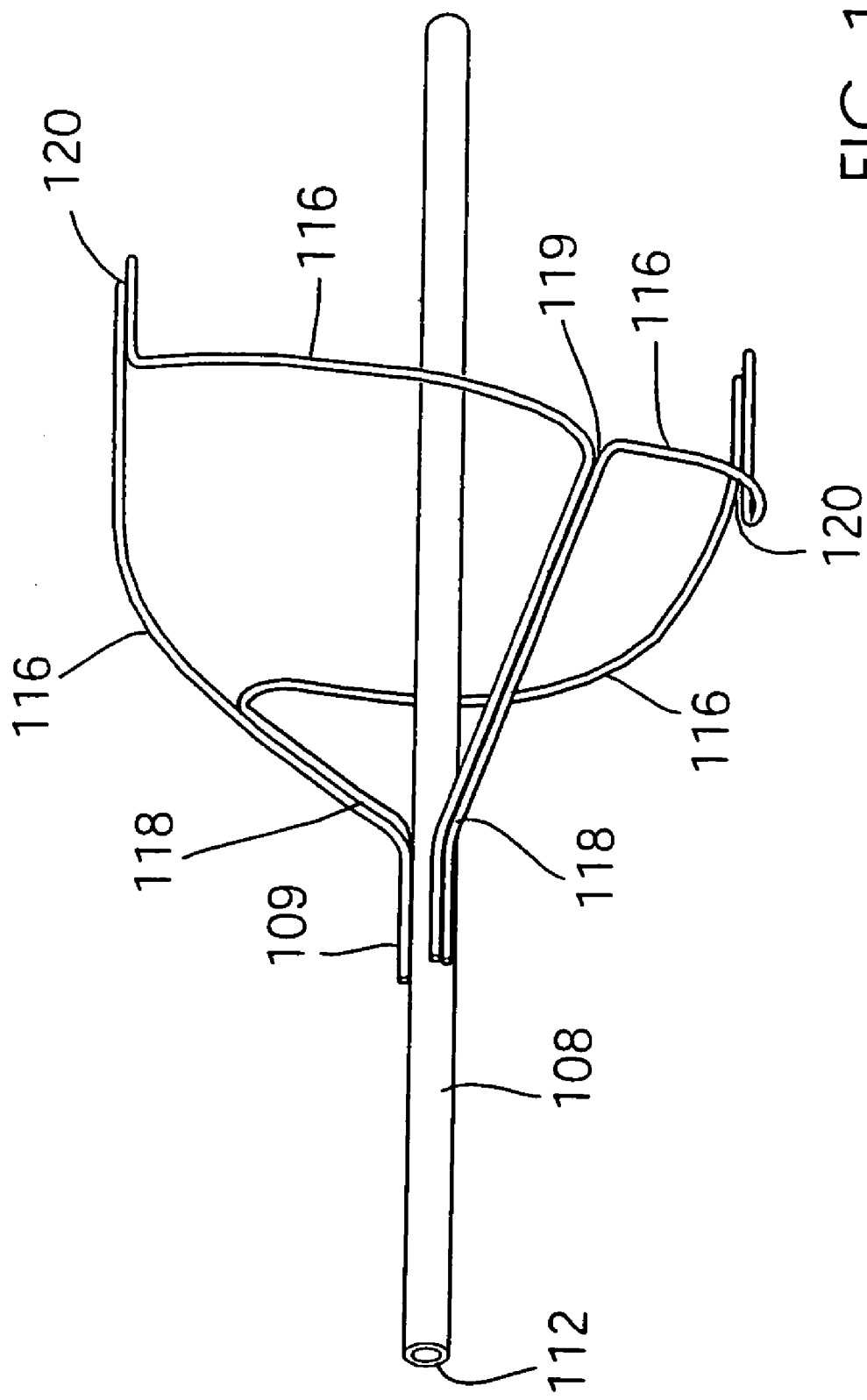
FIG. 140 is a perspective view of another support frame of the invention.
Figure 141:
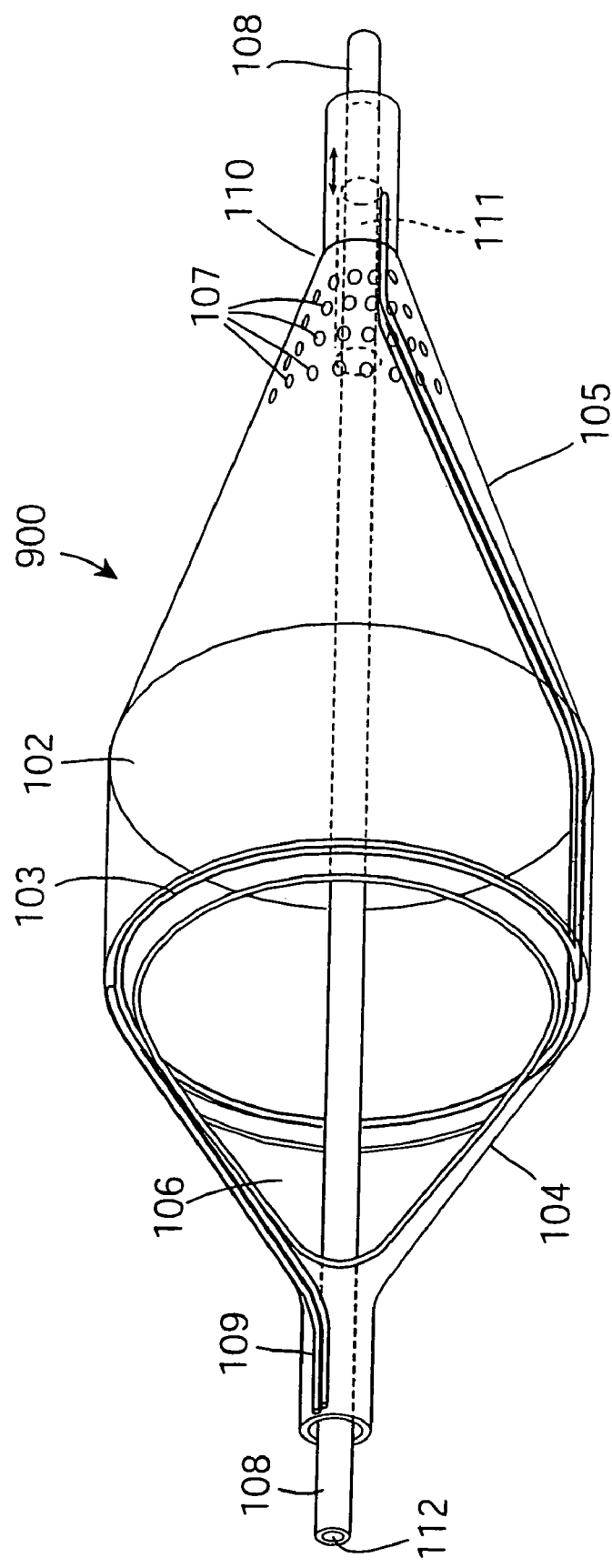
FIG. 141 is a perspective view of another embolic protection device.

The filter 190 of FIG. 140 has two proximal support legs 191, 192 which are axially offset.

Figure 41:
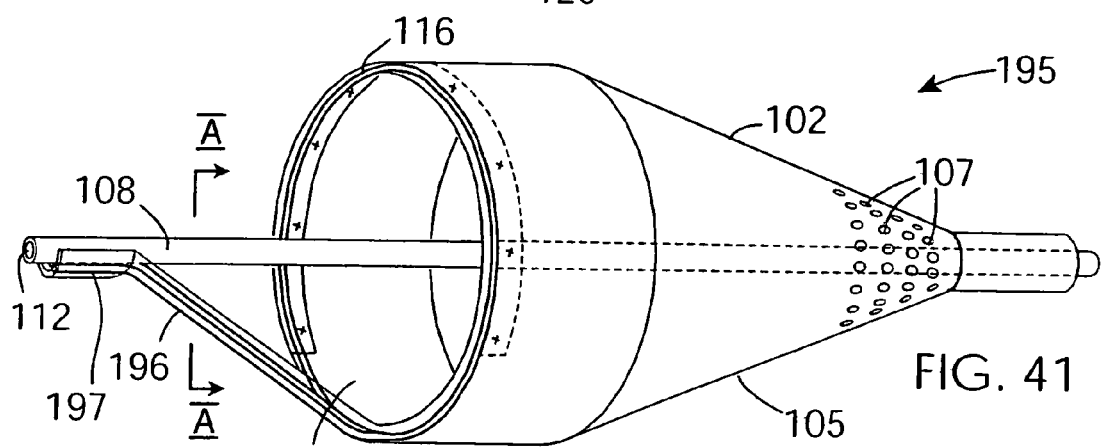
FIG. 41 is a perspective view of another embolic protection device.
Figure 42:
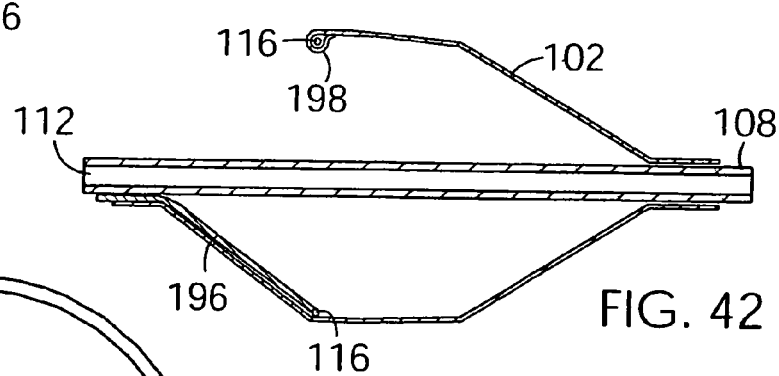
FIG. 42 is a longitudinal cross sectional view of the device of FIG. 41.
Figure 43:
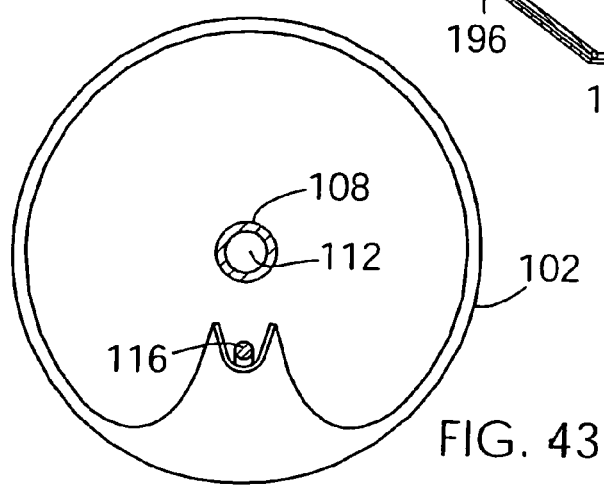
FIG. 43 is a cross sectional view on the line A—A in FIG. 41.

Referring to FIGS. 41 to 43 another filter 195 has a single proximal support arm 196 which terminates in an open collar 197 which is slidably engagable with the tubular member 108. This arrangement provides a large single inlet opening on deployment. The support frame is held in a lip 198 of the filter body/membrane 102.

Figure 40:
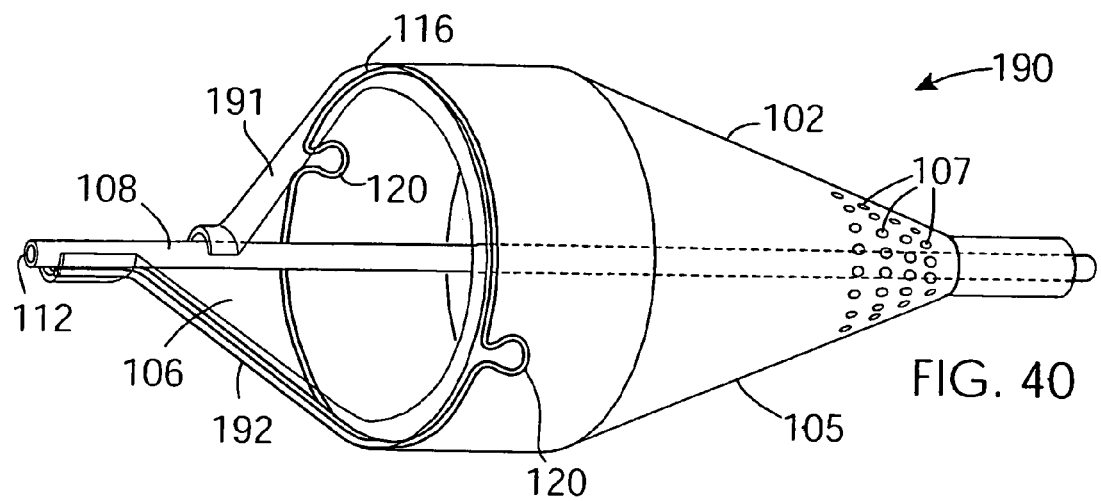
FIG. 40 is a perspective view of a further embolic protection device.
Figure 44:
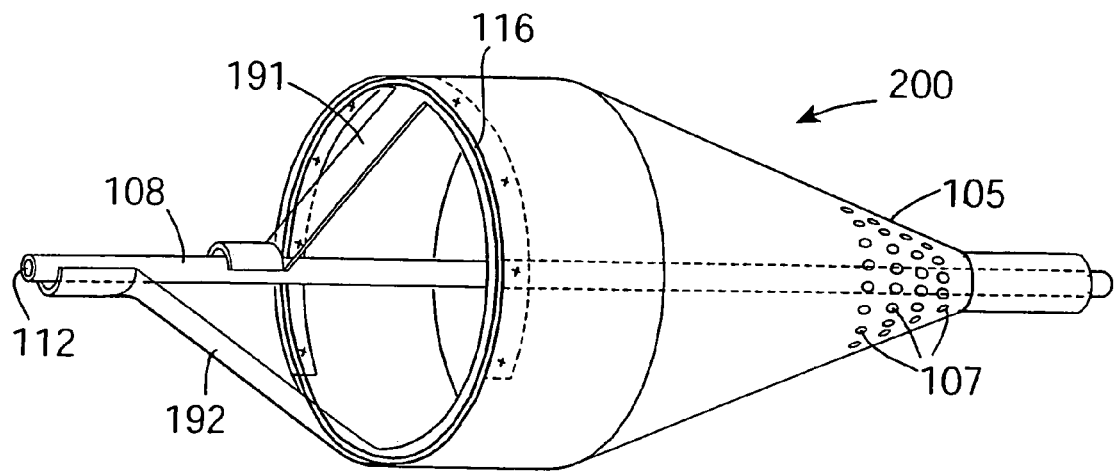
FIG. 44 is a perspective view of another embolic protection device.
Figure 45:
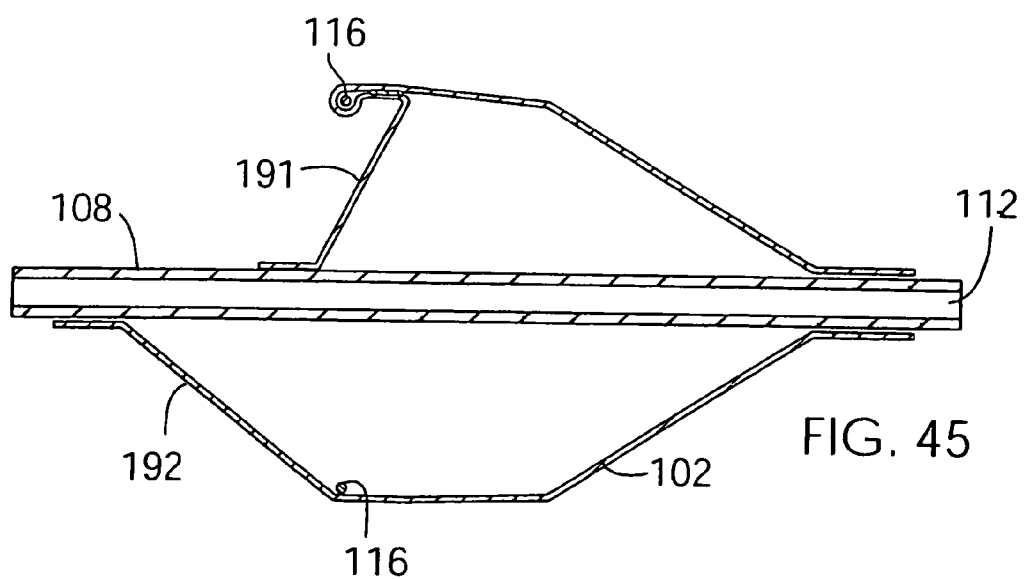
FIG. 45 is a cross sectional view of the device of FIG. 44.

Another filter 200 is illustrated in FIGS. 44 and 45 which has a construction similar to that of FIG. 40 but with the support frame having neither proximal nor distal support arms. This frame design provides a very short wrapped length for superior trackability. The stepped filter arms provide a large inlet opening on deployment.

Various alternative support frames are illustrated in FIGS. 46 to 51. In each case, the support hoop is of generally elliptical shape.

In the support 205 of FIGS. 46 and 47 the hoop is biased towards an elliptical shape in its unconstrained state. When constrained within a vessel the major axis of the elipse will be compressed, which will tend to expand the minor axis. This action may assist in the even distribution of radial force to the vessel wall in the case where the support frame is inherently more flexible at the loops than at the top of its proximal arms.

In the support 215 of FIGS. 48 and 49 the proximal arms of the support frame are staggered so that the hoop is inclined at an angle to the axis of the filter in side view.

Thus although the hoop is actually elliptical it appears circular in end view as shown in FIG. 51.

In the support 210 of FIGS. 50 and 51 the loops of the support frame are offset so that the hoop is inclined at an angle to the axis of the filter in top view. Thus although the hoop is actually elliptical it appears circular in end view as shown in FIG. 51.

Figure 52:
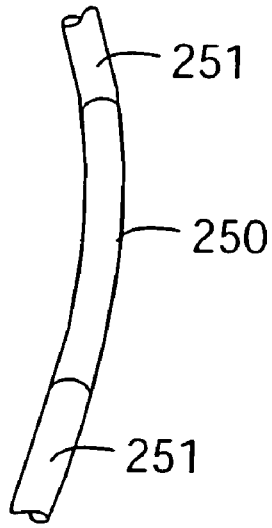
FIGS. 52 to 62 are various views of linkage elements rendered radiopaque.
Figure 53:
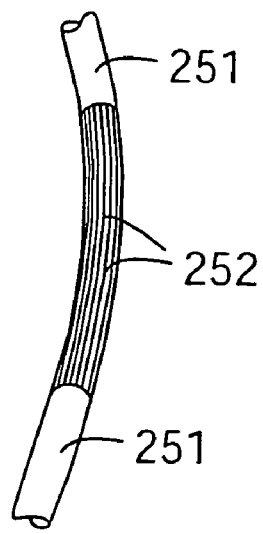
Figure 54:
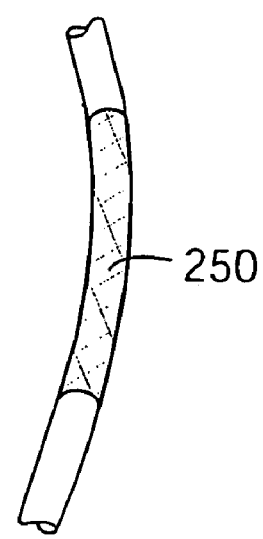
Figure 55:
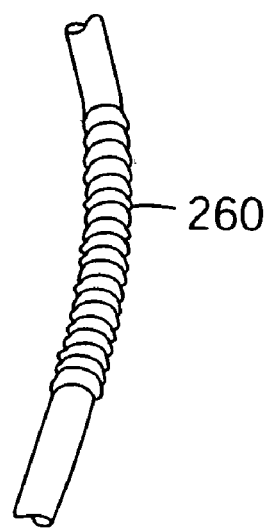
Figure 56:
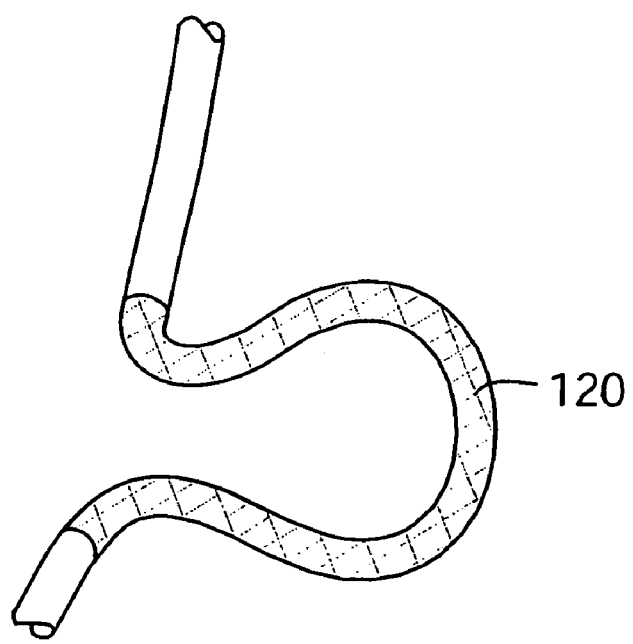

To enhance visualisation of the filter the wire segments and/or the linkage elements may be rendered radiopaque. Referring to FIG. 52 a section 250 is of a different material or has different properties than that of the wire or linkage element 251. The section 250 is ductile and radiopaque. In FIG. 53 the section 250 is formed by straight wires 252 some or all of which may be radiopaque. In FIG. 54 the section 250 is of braided construction, some or all of which may be radiopaque. A radiopaque coil 260 is provided in FIG. 55. In FIG. 56 a linkage element 120 is rendered radiopaque by using a radiopaque braid. The linkage element 120 may be of different material and/or have a similar radiopacifying arrangement as shown in FIGS. 52 to 55.

Figure 57:
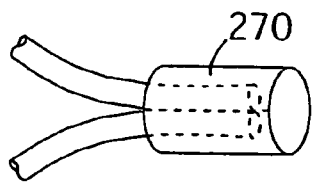
Figure 59:
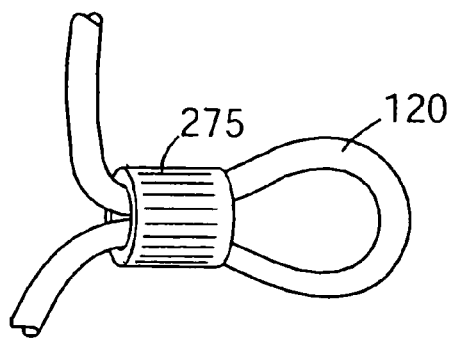
Figure 58:
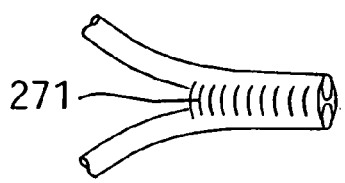
Figure 60:
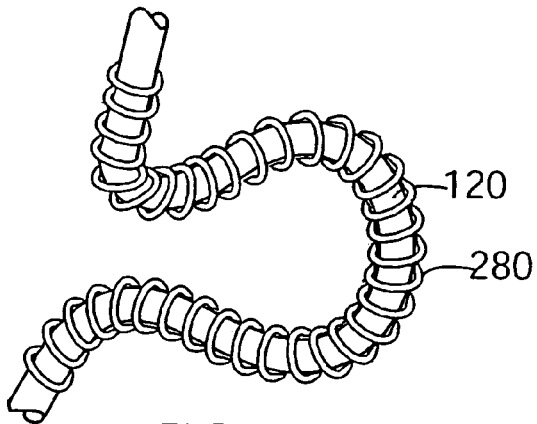
Figure 61:
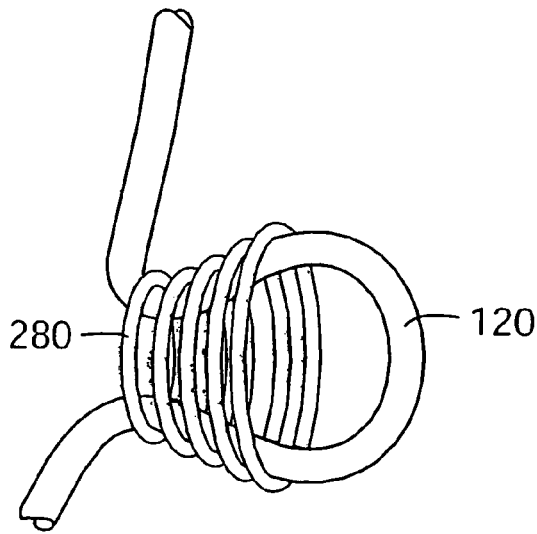
Figure 62:
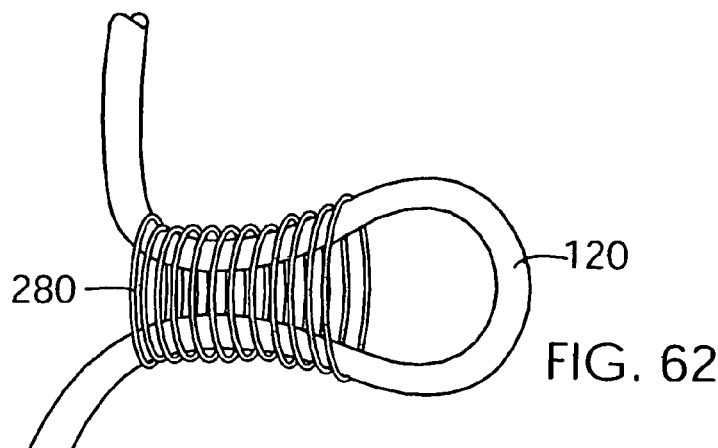

Methods of rendering terminations and/or linkage element radiopaque are illustrated in FIGS. 57 to 62. In FIG. 57 a radiopaque band or cup 270 may be used. A radiopaque solder 271 may also be used (FIG. 58). Similarly a radiopaque band 275 may be crimped around the neck of a loop 120 as illustrated in FIG. 59. A coil 280 of radiopaque material may be wound around the loop 120 as illustrated in FIG. 60 or across the loop as illustrated in FIGS. 61 and 62.

As illustrated in FIG. 63, at least part of the support may be of a multifilament wire construction. In this case seven Nitinol wires 300 are wound in a spiral around a single radiopaque wire 301, the radiopaque wire 301 being located substantially along the axis of bending of the support. The support may have the multifilament wire construction along the entire length of the support in this instance.

During bending of the support (FIG. 64), for example upon movement of the support to the expanded configuration, each wire 300, 301 bends independently of the other wires. As a result, the force required to bend the multifilament support is minimised, and thus the filter achieves enhanced trackability during transport through a tortuous vasculature, such as in coronary applications.

Because the Nitinol wires 300 are wound in a spiral around the radiopaque wire 301, this configuration acts to decrease the bending stresses induced in each wire 300, 301 upon bending. (FIG. 64)

The radiopaque wire 301 provides visualisation for a clinician during transport of the filter 1 through a vasculature and deployment of the filter in the vasculature. Because the radiopaque wire 301 is located along the neutral axis of the support, the forces required to plastically deform the radiopaque wire 301 as the support moves from the collapsed configuration to the expanded configuration, upon deployment of the filter 1, are minimised. In this way the dampening effect of the radiopaque material is minimised.

FIG. 65 illustrates portion of a support 310 of another embolic protection filter according to the invention. In this case, the support comprises two radiopaque wires 311 around which are wound in a spiral a plurality of Nitinol wires 312.

A support 315 of a further embolic protection filter according to the invention is illustrated in FIG. 65. The Nitinol wires 318 and the radiopaque wire 317 are braided together to form the multifilament wire support 35.

Referring to FIGS. 67 and 68 there is illustrated a support 320 of another embolic protection filter according to the invention. The support comprises a single radiopaque wire 321 which extends substantially longitudinally, and a single Nitinol, wire 322 which is wrapped around the radiopaque wire 321 in a coil. As illustrated in FIG. 68, the bending stress induced in the Nitinol wire 322 upon bending is substantially less than the bending stresses induced in a solid wire bent through the same angle.

Figure 69:
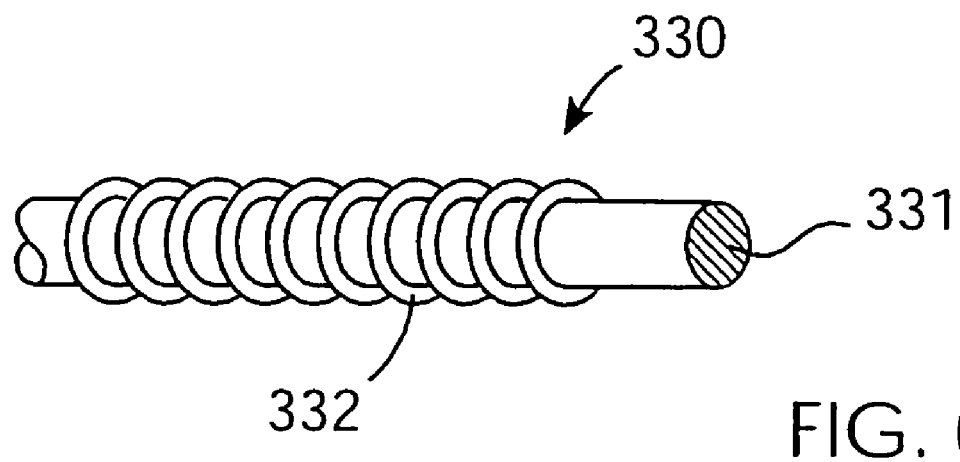
FIGS. 69 to 77 are perspective views of portions of frame elements or linkage elements.

A portion of a wire support 330 of another embolic protection filter is illustrated in FIG. 69. In this case, a single Nitinol wire 331 extends substantially longitudinally, and a single radiopaque wire 332 is wrapped around the Nitinol wire 331 in a coil.

Figure 70:
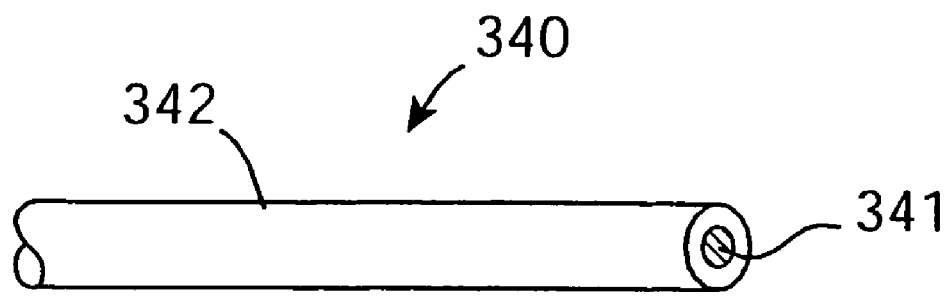

FIG. 70 illustrated part of a support 340 of another embolic protection filter according to the invention. The support 340 does not have any radiopaque wire filaments, instead radiopacity is achieved by a radiopaque core 341 embedded within at least one of the wires 342. The radiopaque core 341 is located substantially along the neutral axis of the Nitinol wire 342, and thus the force required to plastically deform the radiopaque core during movement of the support from the collapsed configuration to the expanded configuration is minimised, and the dampening effect of the radiopaque material is minimised.

Figure 71:
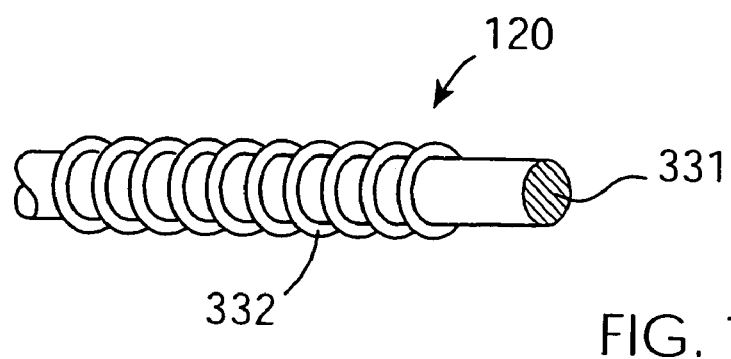
Figure 72:
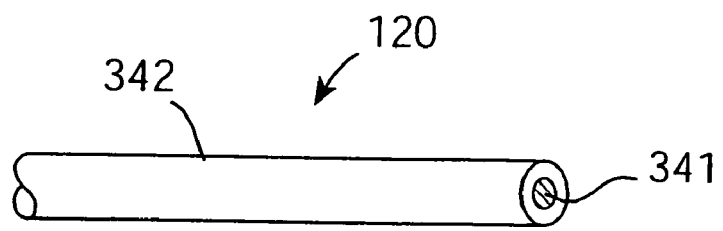

Referring to FIGS. 71 to 72 a linking element loop 120 may be provided with radiopacity in a similar manner.

Figure 73:
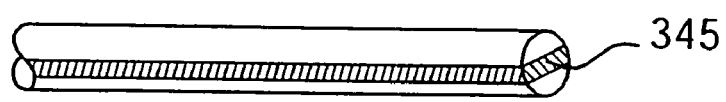
Figure 74:

Referring to FIGS. 73 or 74 a radiopaque material 345 may be sandwiched between two outer layers. Such a frame could be constructed by laser machining an entire frame (or portion thereof) from a large diameter bi-metal or tri-metal tube. The frame cross section could thus be square or rectangular as shown in FIG. 73, or could be electropolished to create an elliptical or round wire shape as shown in FIG. 74.

The support wire(s) may be of any suitable superelastic material, or alternatively of a high strength material, such as stainless steel.

Figure 75:
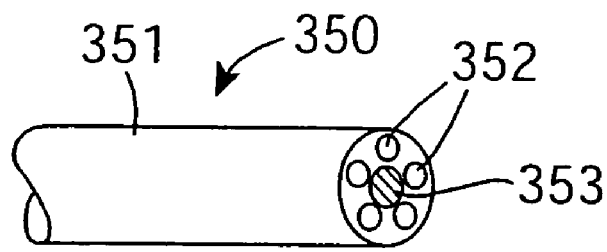

Referring to FIG. 75, there is illustrated portion of a support 350 of another embolic protection filter according to the invention. In this case, the support 350 comprises a jacket 351 of a polymeric material around multifilament wires 352, 353. The Nitinol wires 352 and the radiopaque wire 353 are embedded within the polymeric jacket 351. A variety of manufacturing procedures, such as overmoulding, heat-shrinking, dipping, spraying, painting, depositing may be used to fabricate the wires embedded within the jacket 351. The jacket 351 acts to maintain the structure of the multifilament wire construction intact, and ensures that the wires move in a co-ordinated manner.

Figure 76:
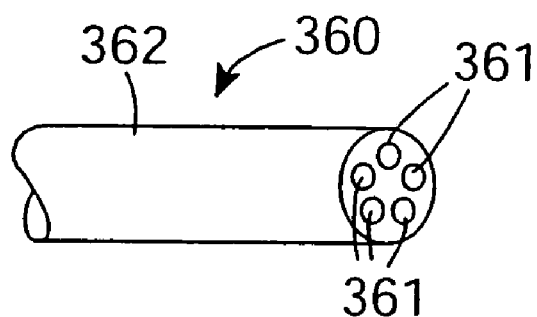

FIG. 76 illustrates a support 360 of another embolic protection filter which comprises five Nitinol wires 361 wound together in a spiral without any radiopaque wire filaments. A radiopaque material, such as tungsten, bismuth subcarbonate, barium sulphate, may be loaded into the polymeric jacket 362 to achieve visualisation.

Figure 77:
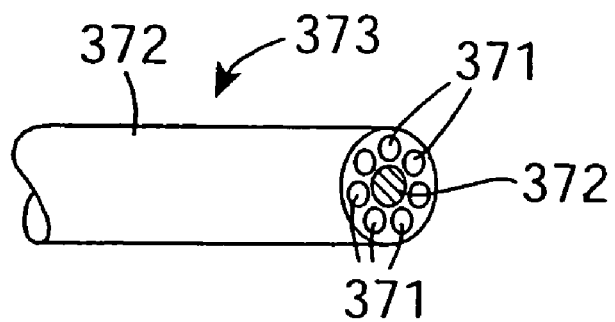

It will be appreciated that a jacket may be used with any of support structure described previously. For example, FIG. 77 illustrated a support 370 of a further embolic protection filter in which the Nitinol wires 371 and the radiopaque wire 372 are braided together and embedded in the polymeric jacket 373.

Various ways of rendering a wire, linkage element or tubular member of the embolic protection devices of the invention radiopaque are illustrated in FIGS. 78 to 83. In general a radiopaque material 390 is provided around the element or may itself define the element such as in the case of the tubular member of FIG. 83.

Figure 84:
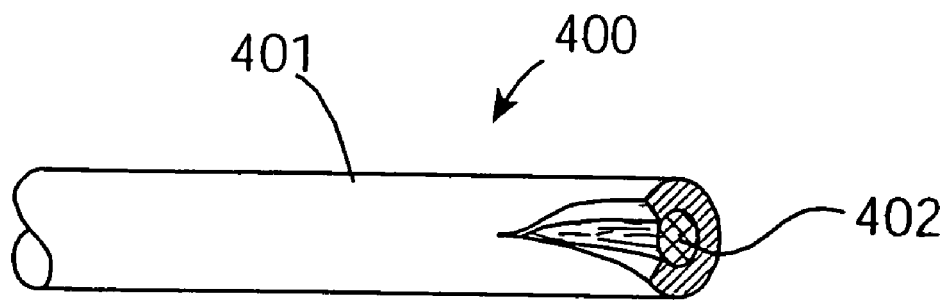
FIGS. 84 to 86 are perspective views of portions of other frame elements or linkage elements.

Referring to FIG. 84 a portion of a support 400 may be in the form of one or more wires 401 of superelastic material, such as Nitinol. A core of radiopaque material is embedded within at least portion of at least one of the support wires 401. In this case, the core is also in the form of a wire 402 of a suitable radiopaque material, such as gold, or platinum, or mercury and extends along the length of a support wire. The radiopaque wire 402 is located substantially along the neutral axis of bending of the support wire 401. The radiopaque wire 402 provides visualisation for a clinician during transport of the filter through a vasculature and deployment of the filter in the vasculature. By providing the radiopaque wire 402 as the core of the support wire 401, this minimises the diameter of the radiopaque wire 402 and its distance from the neutral axis. Because the second moment of area of the radiopaque wire 402 is proportional to the fourth power of its diameter, the second moment of area of the radiopaque wire 402 is also minimised. Correspondingly, the forces required to plastically deform the radiopaque wire 402 as the support wire 401 moves from the collapsed configuration to the expanded configuration, upon deployment of the filter, are also minimised. In this manner, the radiopaque core configuration of the invention acts to minimise the dampening effect of the radiopaque material, which is necessary to achieve visualisation of the filter.

Figure 85:
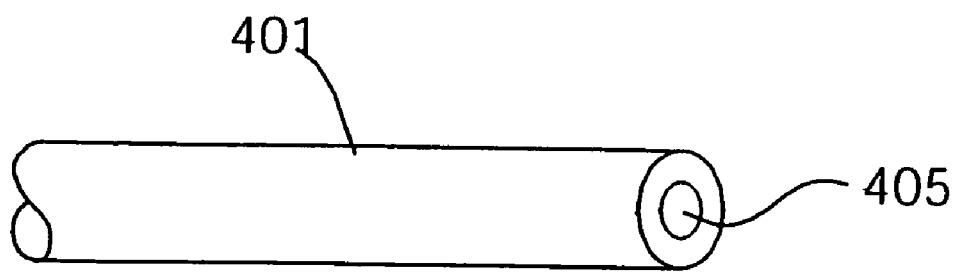
Figure 86:
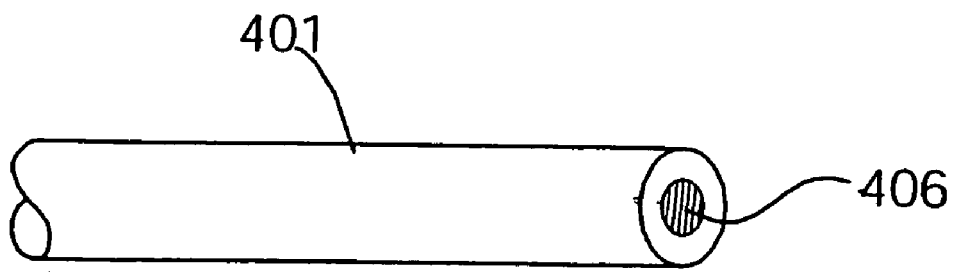

The radiopaque material may also be provided in powder form 405, as illustrated in FIG. 85, or in liquid form 406, as illustrated in FIG. 86. Because the radiopaque core 405, 406 is embedded within the support wire 401, the radiopaque powder or radiopaque liquid 26 will be safely retained and controlled within the support wire 401.

By using a powder or liquid for the radiopaque material, the yield stress of the radiopaque material is reduced. Thus the forces required to move the support wire 401 from the collapsed configuration to the expanded configuration are further reduced.

The support may comprise a reservoir for enclosing a fluid, the reservoir being provided, which extends circumferentially around the filter at the inlet end 104 to form an enclosed loop around the inlet opening.

The tube may enclose a fluid such as mercury. The temperature of the fluid increases towards body temperature upon deployment of the filter in a vasculature, which causes the fluid to expand. This expansion of the fluid forces the support tube towards the expanded configuration until the support tube is fully expanded and the filter is supported in the expanded configuration.

It will be appreciated that the expansile fluid may be of any suitable material. By using a radiopaque material, such as mercury, this provides the additional advantage that visualisation of the filter will be possible during transport of the filter through a vasculature and deployment of the filter in a vasculature.

In another embolic protection filter according to the invention, the fluid enclosed in the reservoir may be pressurised. In this case, upon release of a constraint on the filter, such as upon deployment of the filter out of the pod of the delivery catheter, the pressurised fluid in the support reservoir forces the support towards the expanded configuration until the filter is supported in the fully expanded configuration.

It will be appreciated that the radiopaque core aspect of the invention, and/or the temperature expansile fluid aspect of the invention, and/or the pressurised fluid aspect of the invention may be used in any suitable manner or combination with any appropriate medical device.

It will further be appreciated that aspects of the invention may be applied with any medical device for transport through a body passageway and deployment in a body.

Referring to FIGS. 87 to 105 there are illustrated various alternative support frames incorporating tethering features for connecting the support frame distally and/or proximally and/or intermediately to a carrier. Tethers may also be used additionally or alternatively for connecting various elements of a support frame.

In all cases the tethers may be of any suitable material such as fine gauge wire, for example Nitinol wire, fibre or polymers. The tethers may be of solid or braided construction, for example.

Figure 87:
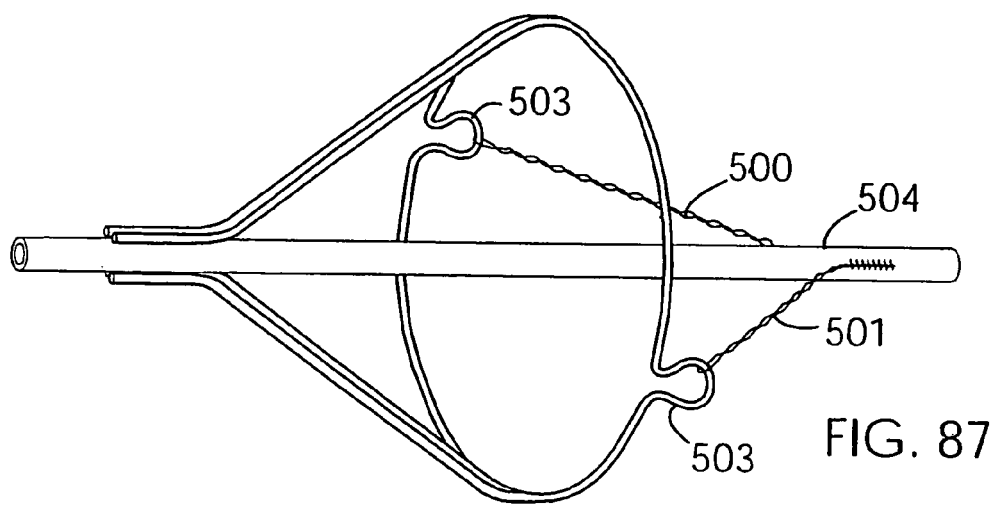
Figure 88:
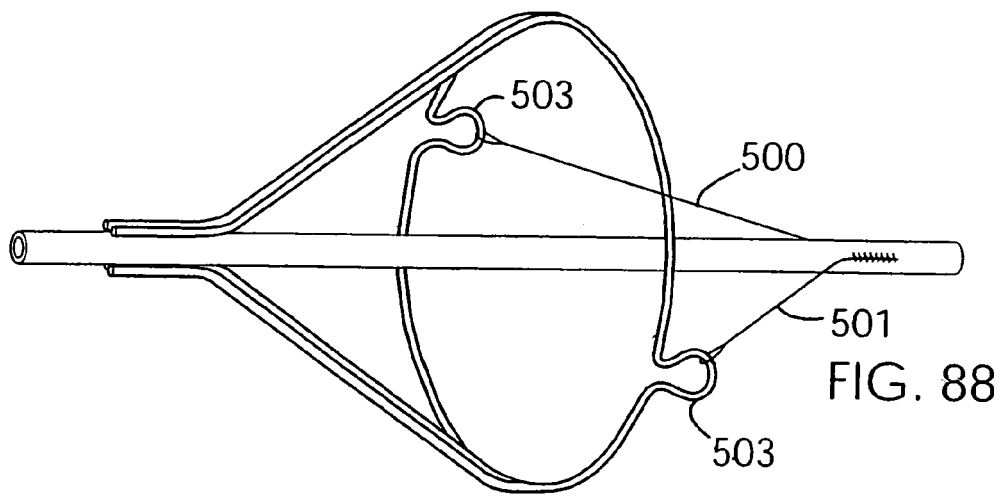
Figure 89:

Referring to FIGS. 87 to 89 two distal tethers 500, 501 are used to connect a support hoop 503 to a tubular member 504. The distal tethers provide added safety and stability to the frame without any increase in the length of the device when wrapped down as illustrated in FIG. 89.

Figure 90:
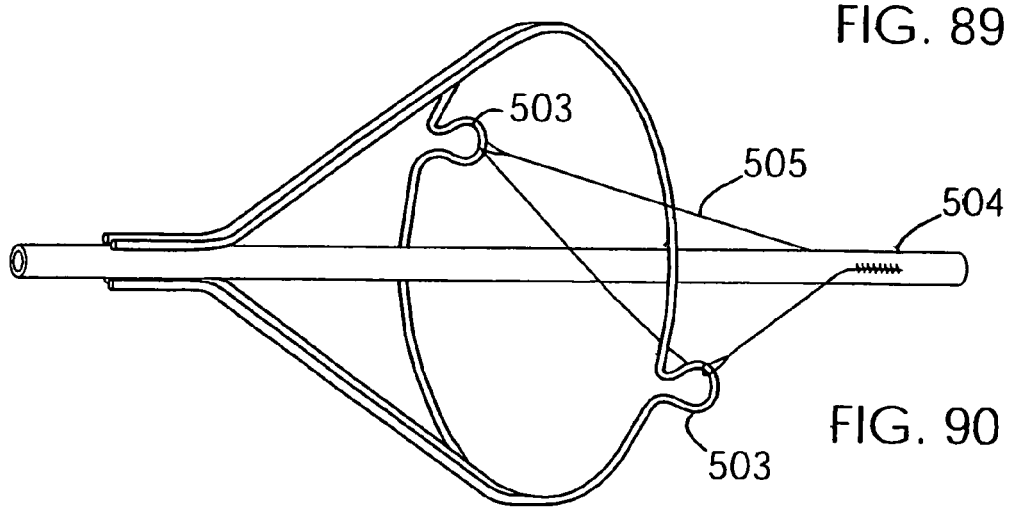

FIG. 90 illustrates an alternative arrangement of distal tethers 505.

The tethers may be connected to the support frame and carrier in any suitable fashion. For example, the distal tethers may be double stranded and looped around the support frame as shown in FIG. 87.

Referring to FIGS. 91 to 96 there are illustrated various constructions with proximal tethers, with FIG. 90 illustrating a basic construction of two tethers 520 and a simple hoop support frame.

FIG. 92 illustrates a similar frame to that shown in FIG. 9 previously, but with the proximal frame arms replaced with tethers 520. Additional strain relieving loops are provided at the tether connection points to assist in the wrap down of the device as discussed previously in relation to the distal loops. The use of flexible tethers in place of wire arms enables the length and stiffness of the wrapped down frame to be reduced, enhancing the trackability of the device. The flexibility of the tethers also enables an even radial force to be provided around the circumference of the frame without interference from the proximal arms.

In FIGS. 93 to 95 there are two tethers 521, 522 one 521 of elastic and the other 522 of inelastic material. The elastic tether acts to expand the filter and frame during deployment, but stretches to enable the frame to collapse into two parallel wires during retrieval/wrapping as shown in FIGS. 94 & 95. This mode of collapse provides a longer wrapped frame than would be the case for FIG. 92. By varying the size, shape and position of the strain relieving loops as shown benefits in the wrapped profile of the frame support may be provided.

Figure 97:
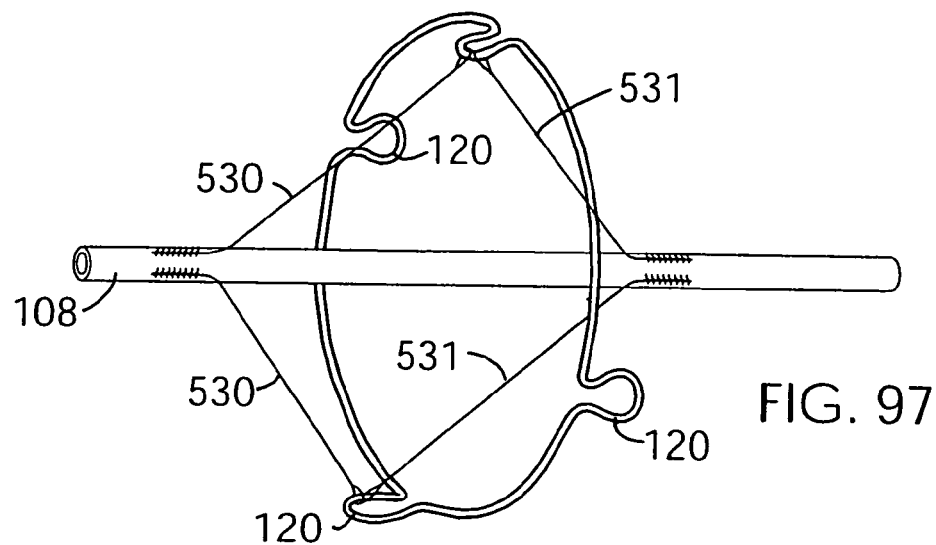

In FIG. 97 there are proximal tethers 530 and distal tethers 531. This construction provides the benefits described in relation to FIG. 92 with the added benefit of the safety and stability provided by the distal tethers. Again the tethers provide a means of anchoring the support frame to the carrier without affecting the stiffness or profile of the wrapped device.

Figure 98:
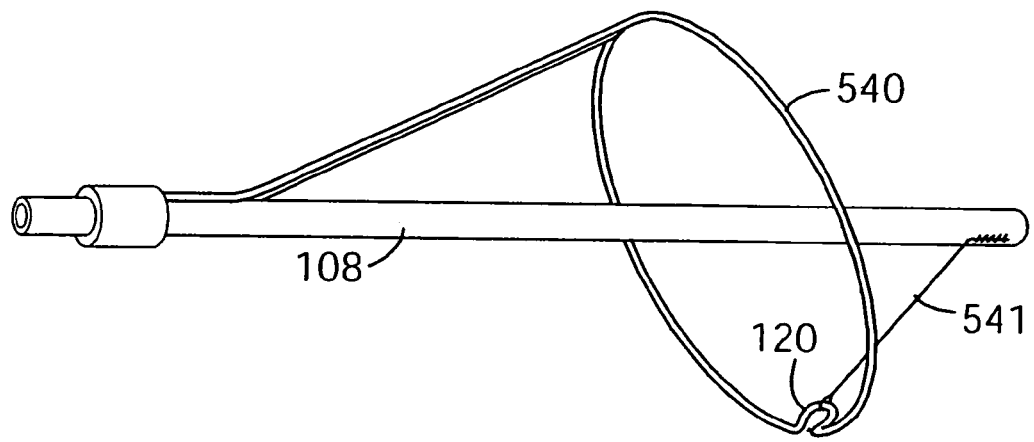

In FIG. 98 an offset loop support 540 has a distal tether 541 to prevent the support frame from moving too far proximally and outside the filter body.

Figure 99:
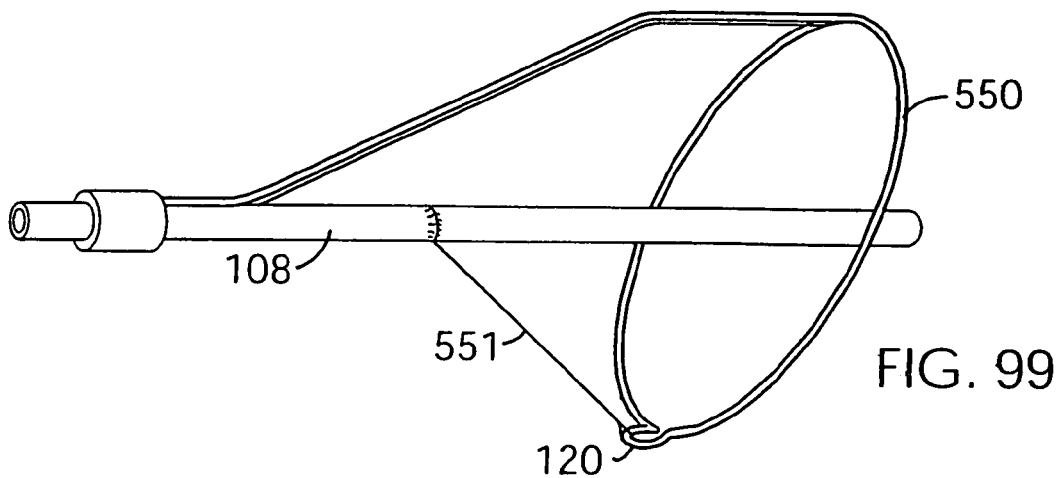
Figure 100A:
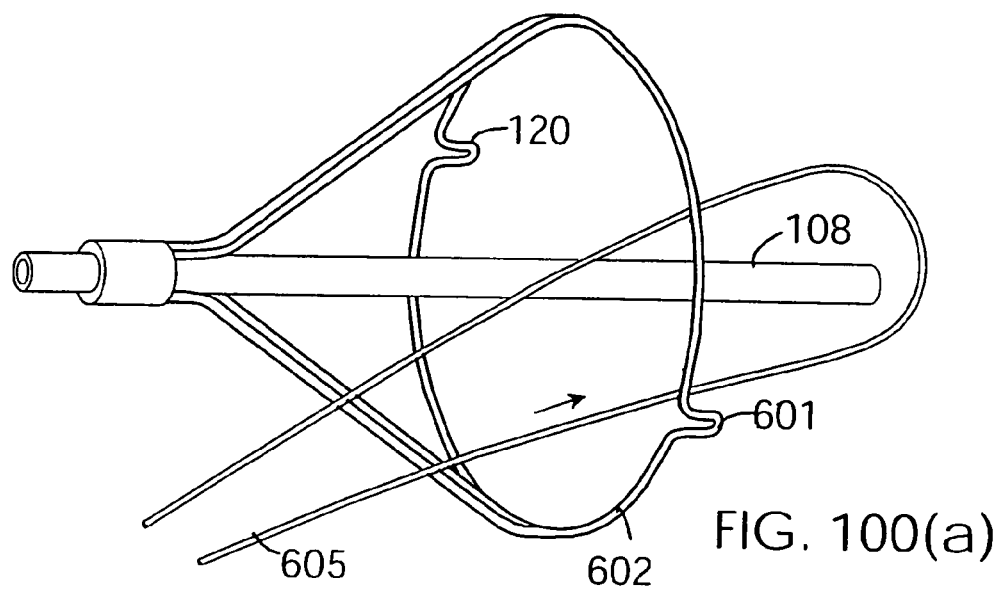
FIGS. 100(a) to 100(d) are perspective views illustrating one attachment of a tether to a support frame.
Figure 100B:
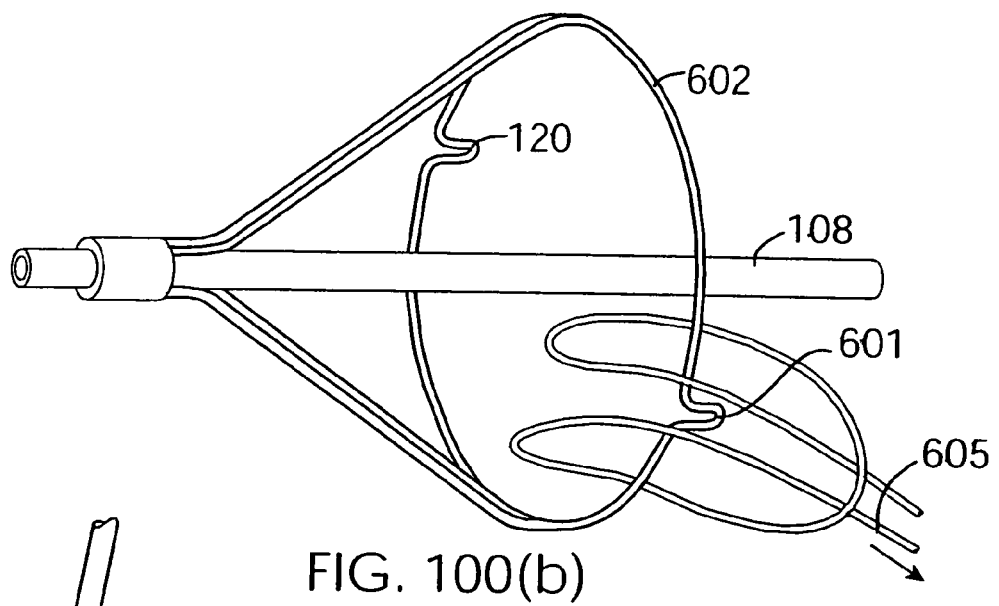
Figure 100C:
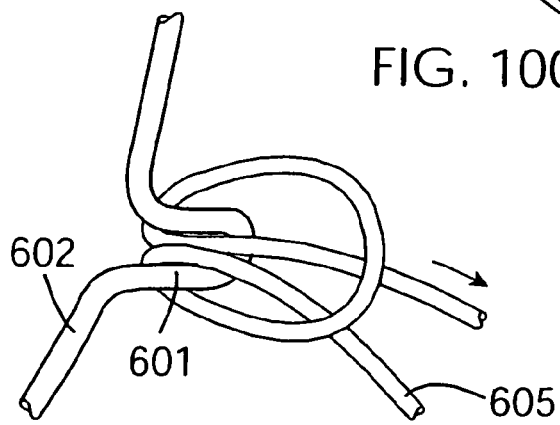
Figure 100D:
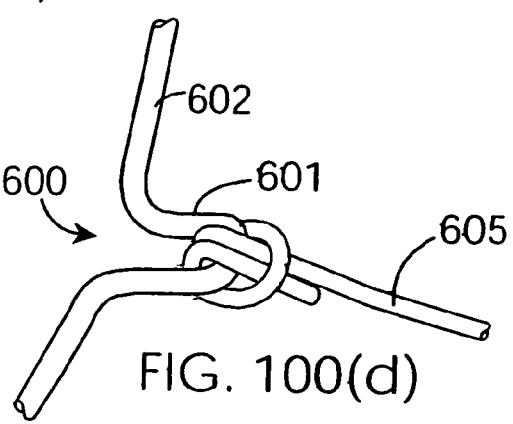

In FIG. 99 another offset loop 550 has a proximal tether 551 to restrain the movement of the loop section of the frame and thus reduce the overall length of the wrapped device.

Referring now to FIGS. 100(a) to 100(d) there is illustrated one type of knot 600 in a tether 605 being tied to a linkage element loop 601 of a support hoop 602.

Figure 101:
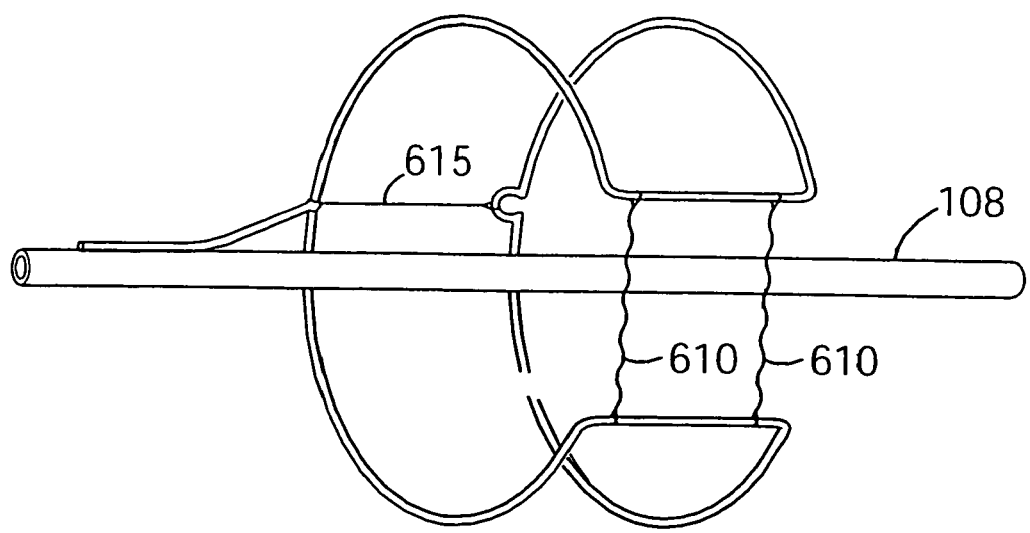
FIG. 101 is a perspective view of another support frame including tethers.

Referring to FIG. 101 there is illustrated a support frame with circumferentially extending tethers 610 which allows the frame to move circumferentially to accommodate a broad vessel size range. The tethers 610 also assist in providing added support to a filter body, especially in large vessels. There is also an axially extending tether 615 interconnecting elements of the support frame.

Figure 102:
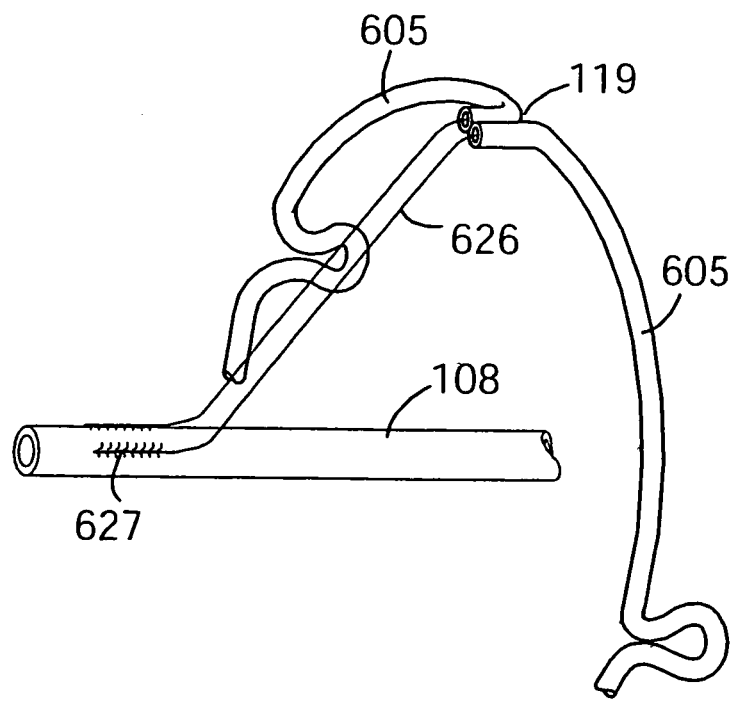
FIG. 102 is a perspective view of partion of a further support frame.

Referring to FIG. 102, there is illustrated a filter support 620 comprising a hollow tube 605 which extends circumferentially around the support frame to define a hoop. A tether 626 is looped through the tube 605, passing out of the tube 605 at the proximal termination point 119. The tether 626 extends proximally and radially inwardly from the proximal termination point 119 to the inner tube 108 to which the ends 627 of the wire 626 are fixed. The tether 626 could be of wire and/or of a radiopaque material.

Torqueing of the tether 626 within the tube 605 is possible during collapsing and expanding of the filter. In the filter support, the tube 605 exerts the outward radial force to support the filter body 102 in the extended outwardly projecting position, and the element 626 acts as a flexible tether to maintain safe, reliable control over the support tube 605.

The support tube 605 may be of any suitable material, such as polyamide or a superelastic material, for example Nitinol. The tube 605 may be flexible or rigid. The tube 605 strengthens the proximal termination point 119 while permitting a degree of flexibility at the proximal termination point 119.

One end of the tether 626 may terminate at the proximal termination point 119 where the end is attached to the other side of the looped tether 626, with the other end of the tether 626 fixed to the inner tube 605.

The invention incorporates circumferential wire angulation into support structure design to give maximum circumferential support to the filter membrane.

Figure 103:
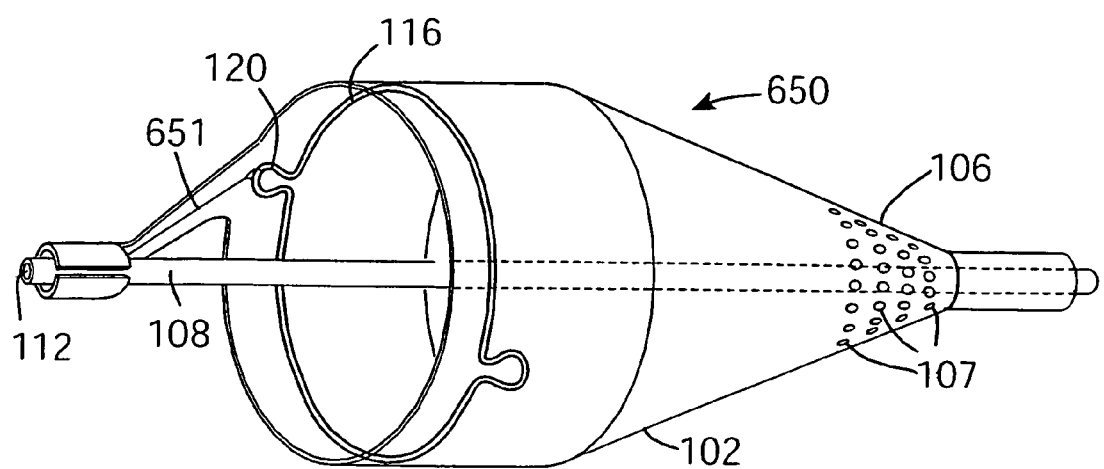
FIG. 103 is a perspective view of another embolic protection device of the invention.

Referring now to FIG. 103 a filter 650 with a proximal tether 651 extending from the support hoop is illustrated. Other details of this filter are as described with reference of FIGS. 36 and 41.

Figure 104:
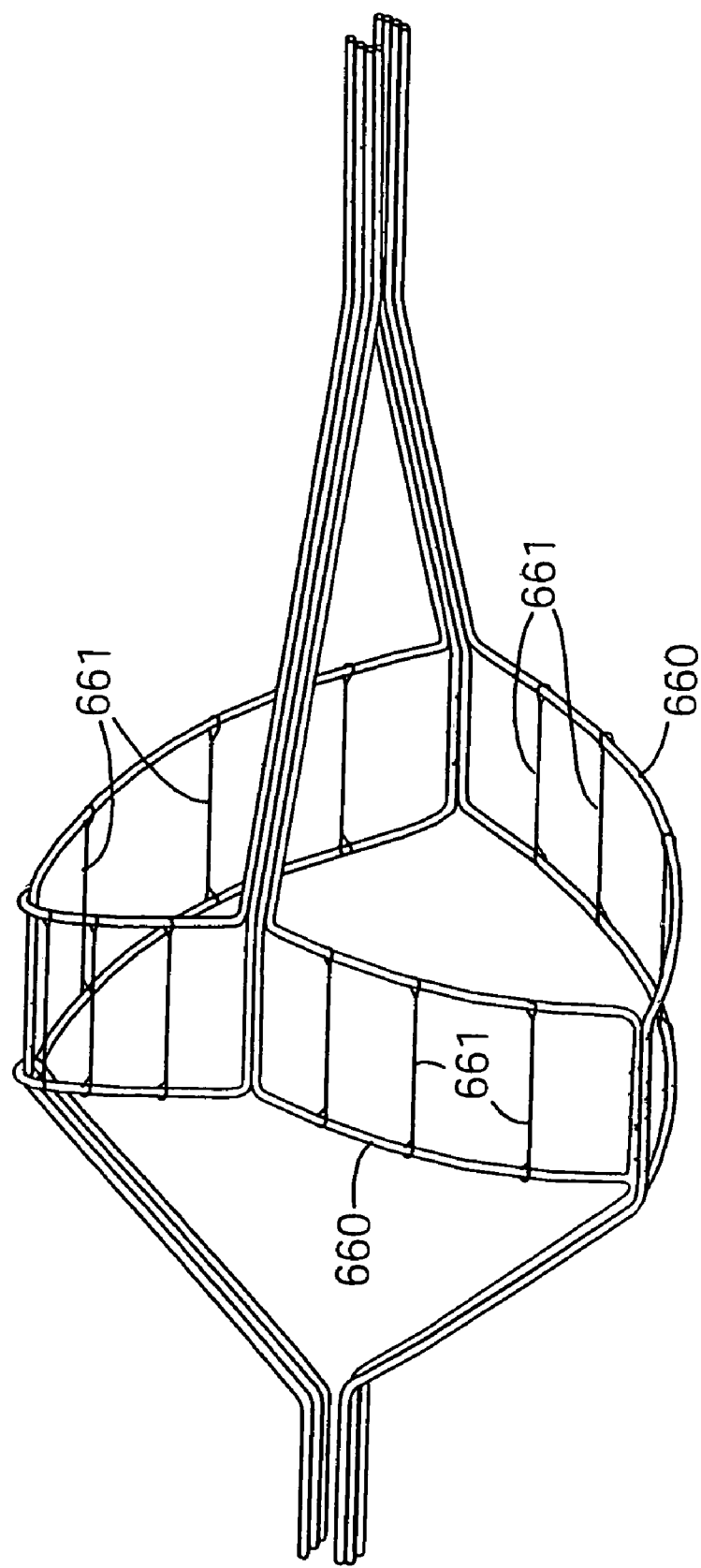
FIG. 104 is a perspective view of another support frame.

Referring to FIG. 104 there is illustrated an alternative support frame in which axially adjacent frame elements 660 are interconnected by tethers 661 which provide additional support for the filter body. The tethers 661 may be of light gauge thread or wire to facilitate ease of wrapping down.

Figure 105:
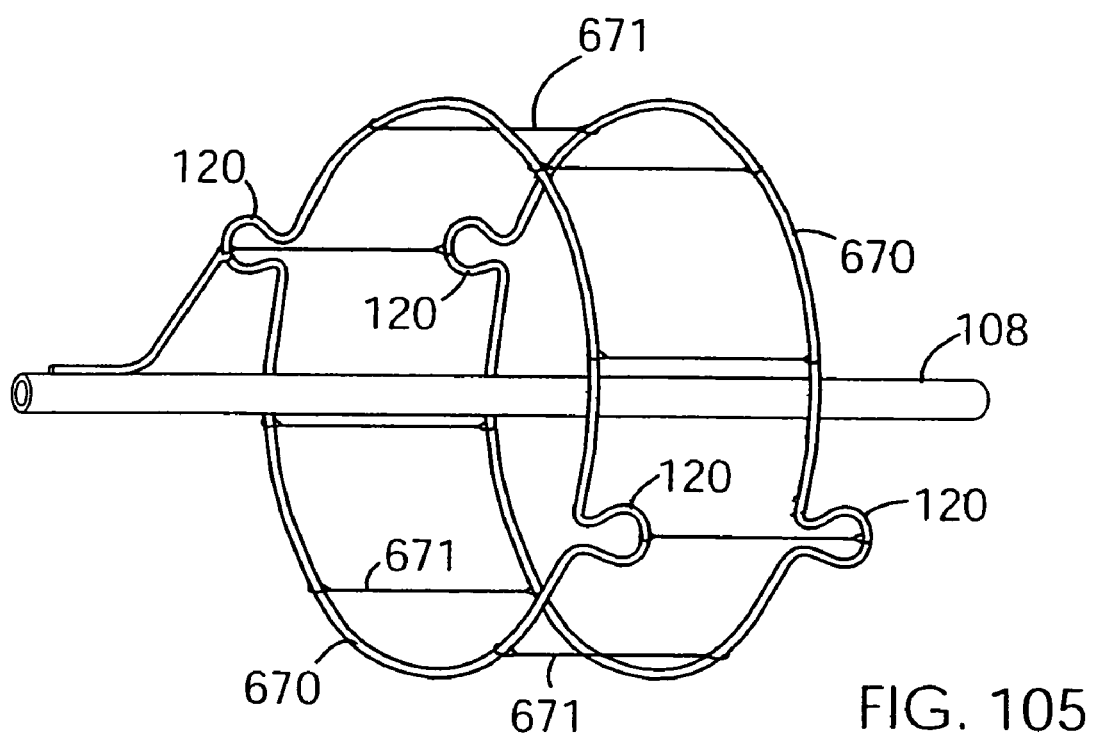
FIG. 105 is a perspective view of a further support frame.

Referring to FIG. 105 there is illustrated another filter support frame comprising two axially spaced-apart support hoops 670 interconnected by axially extending tethers 671. The tethers 671 provide membrane support but are of light and flexible material which will add very little to the wrapped profile or stiffness of the support frame.

Referring next to FIG. 106, there is illustrated another filter element 700. In this case, the filter support comprises four round wires 116 which extend axially and radially outwardly in two legs 118 from the proximal end to two opposed proximal termination points 119.

The wires 116 separate at the proximal termination points 119 and extend circumferentially around the support frame 115 until two opposed distal termination points 120 are reached. The wires 116 then regroup into legs 121 at the distal termination points 120, the legs 121 extending axially and radially inwardly to the sleeve 111 to which the wires 116 are fixed.

In this case, the proximal termination points 119 are 90° offset from the distal termination points 120.

FIG. 107 illustrates a support frame 710 of simpler construction that than of FIG. 106.

Figure 108:
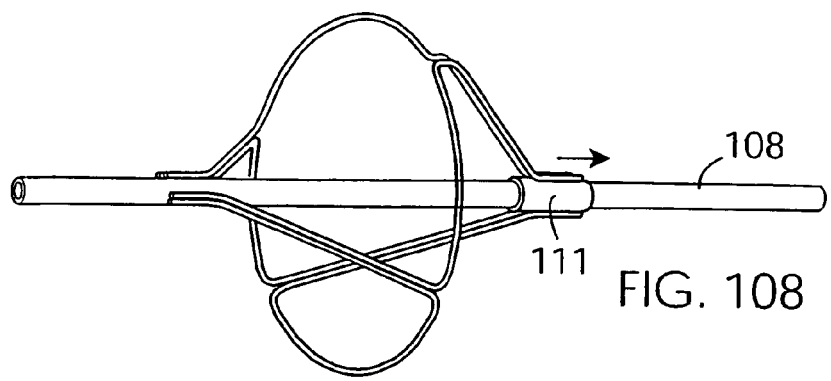
FIG. 108 is a perspective view of a further support frame.
Figure 109:
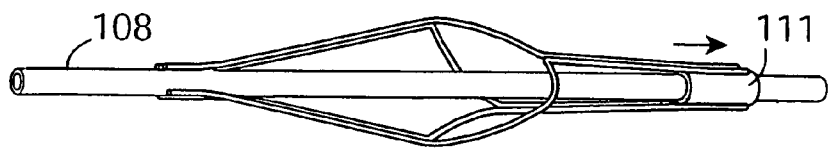
FIG. 109 is a perspective view illustrating the wrapping down of the frame of FIG. 108.

FIGS. 108 and 109 illustrate the wrapping down of the support frame of the filter of FIG. 106.

Figure 110:
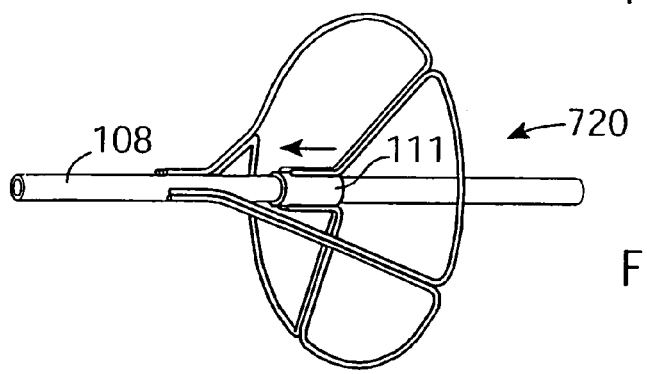
FIGS. 110 and 111 are views similar to FIGS. 108 and 109 of another support frame.
Figure 111:
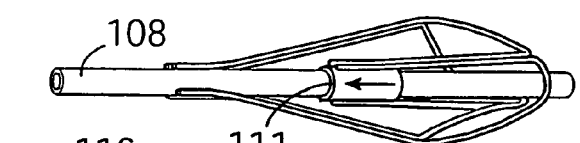
Figure 112:
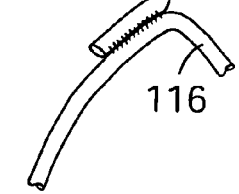
FIGS. 112 to 115 are perspective views illustrating termination details.
Figure 113:
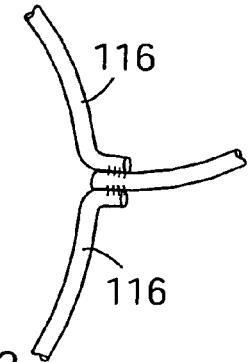
Figure 114:
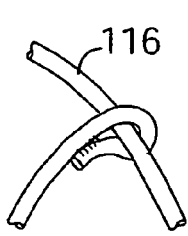
Figure 115:
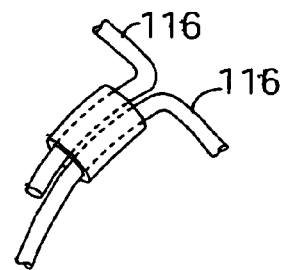

FIGS. 110 and 111 illustrate another support frame 720 in which the sleeve 111 is located proximally resulting in a shorter wrapped down configuration.

FIGS. 112 to 115 illustrate various terminations for the wires in the wire frames of the invention which could be employed to connect a single proximal or distal frame arm to the circumferential hoop portion of the frame. A construction such as that shown in FIG. 114 allows rotation of the hoop relative to the arm, reducing the stresses induced during wrapping.

Figure 116:
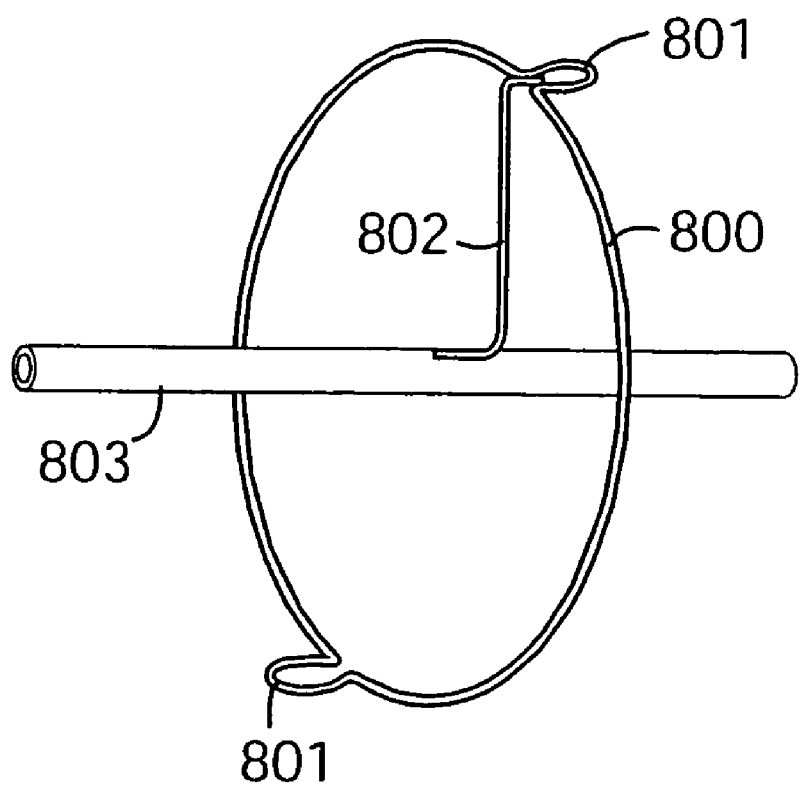
FIG. 116 is a perspective view of another support frame.

Referring to FIG. 116 there is illustrated another support frame comprising a single hoop 800 with two strain distributing loops 801. One of the loops 801 has an arm or tether 802 connecting the hoop 800 to a tubular member 803. This arrangement provides a support frame with a very short parking space in use. Thus, it can be deployed even if only a short segment of vessel is available downstream of a treatment location. The support can wrap down in either direction for loading and/or retrieval.

It will be appreciated that the wires 116 may be slidably mounted to the inner tube 108 at both the proximal support leg 118 and the distal support leg 121.

Figure 117:
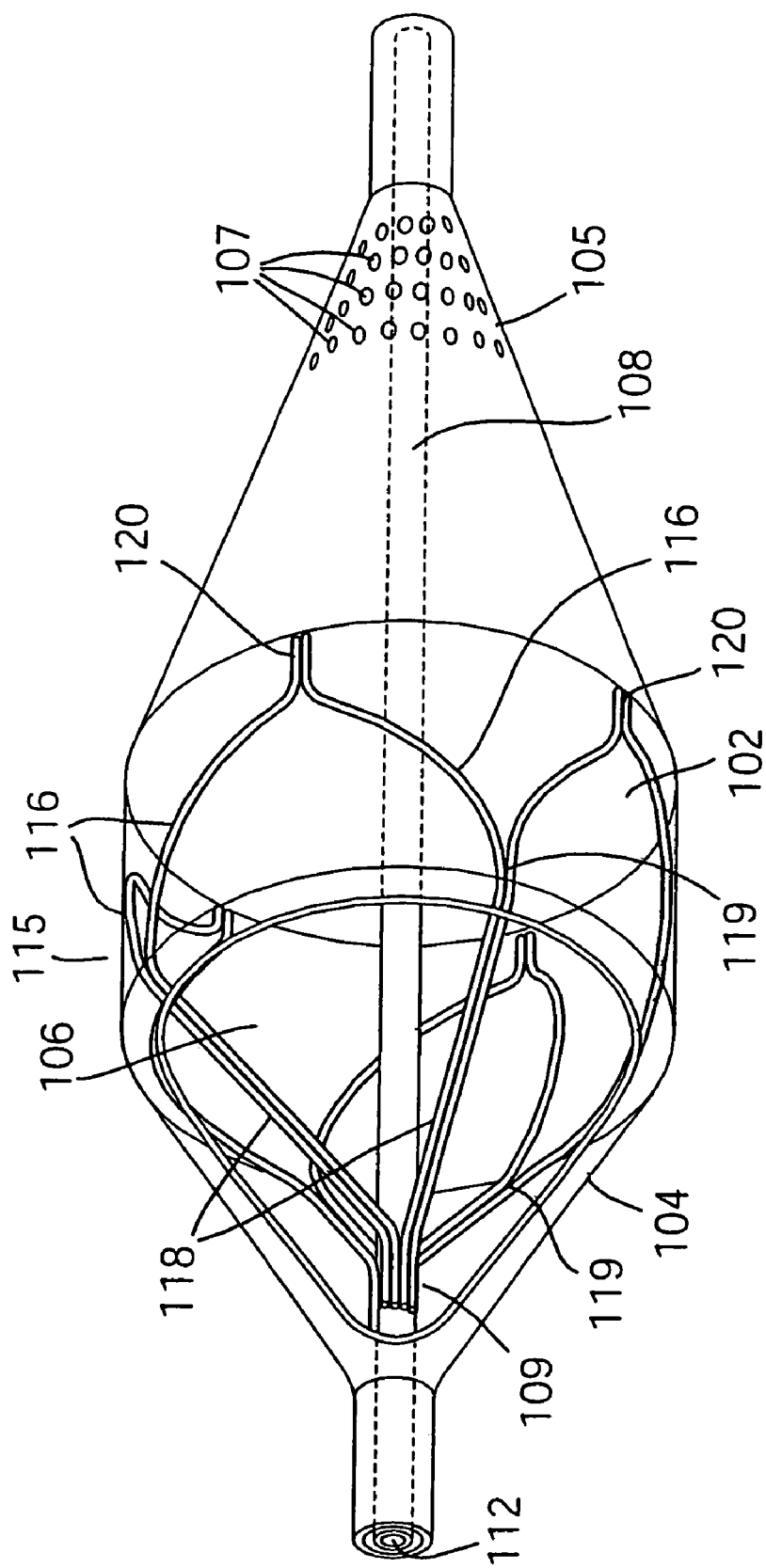
FIG. 117 is a perspective view of another embolic protection device.

It will be further appreciated that by increasing the number of wires 116 which define the complete looped cell 117 of the support frame 115, the elongation of the overall filter support, when collapsed down, will be reduced. For example, the filter support of FIG. 117 comprises eight round wires 116 which extend axially and radially outwardly in four legs 118. In this manner, the space required in a vasculature to deploy and retrieve the embolic protection device is correspondingly reduced.

Depending on the configuration of the filter element, the inner tube may or may not be present. In this case the filter support may be mounted directly onto a guidewire for exchange of the filter element over the guidewire.

It will also be appreciated that the shape of one wire 116 of a cell 117 does not have to be symmetrical or similar to the shape of the other wire 116 of the cell 117, provided that the length of each wire 116 is equal.

Figure 118:
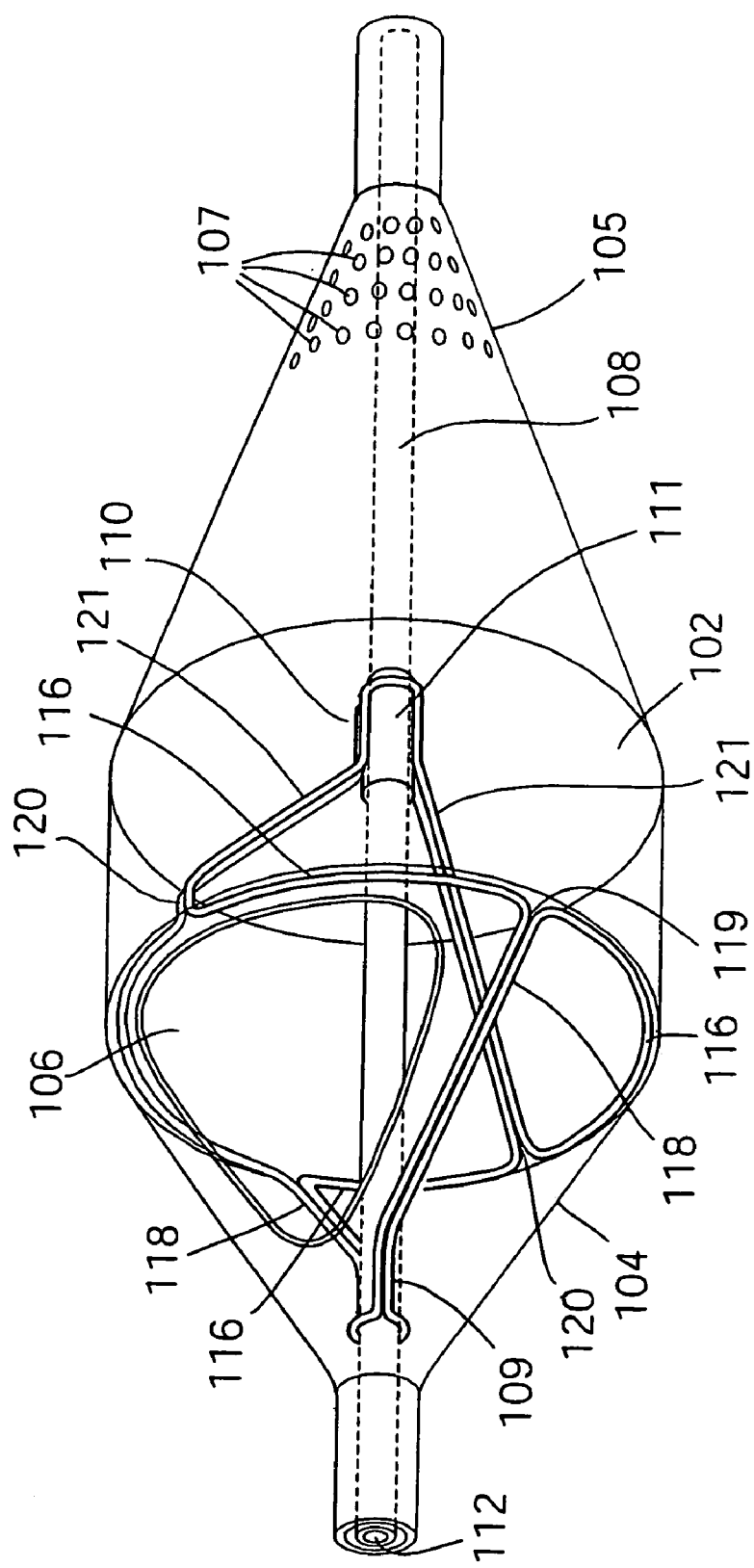
FIG. 118 is a perspective view of a further embolic protection device.

Furthermore it will be appreciated that a single wire 116, bent back on itself, may be used to define the support frame, in which case the cells 117 of the support frame are defined by elements of the single wire, as illustrated in FIG. 118.

Figure 119:
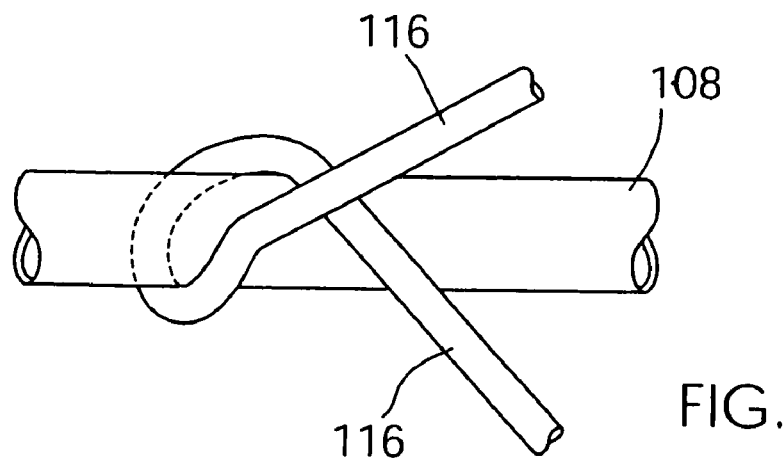
FIGS. 119 to 125 are perspective views of various terminations.
Figure 120:
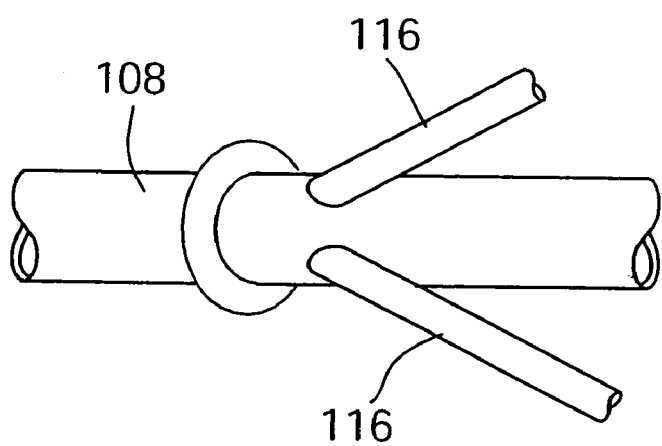
Figure 121:
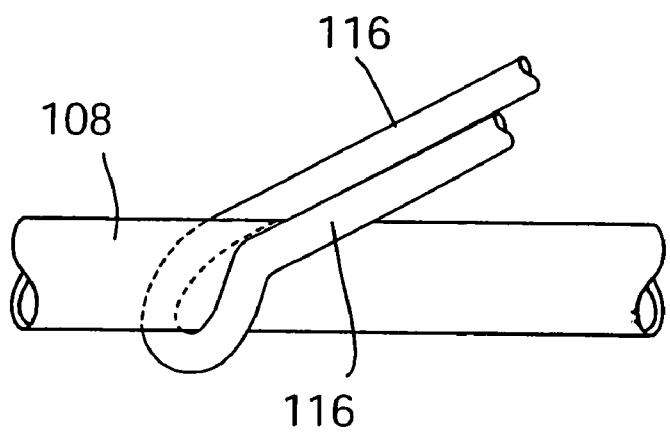

FIGS. 119 to 121 illustrate possible means by which the single wire 116 may be bent back on itself and wrapped around the inner tube 108. This single wire arrangement enables ease of attachment to the inner tube 108 without stress concentration points occurring at the regions of looping of the wire 116 around the inner tube 108.

Figure 122:
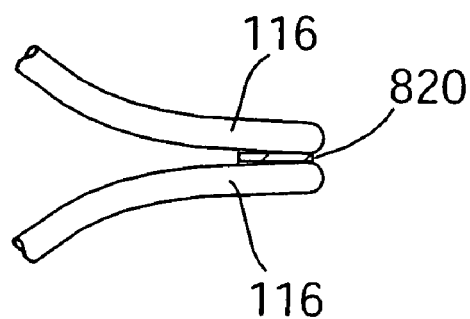

The fixing of two separate wires 116 to each other in a bi-filar arrangement is illustrated in FIG. 122. The fixing means may be provided by, for example, welding, brazing, soldering, or an adhesive joint at the point of fixation 820.

Figure 123:
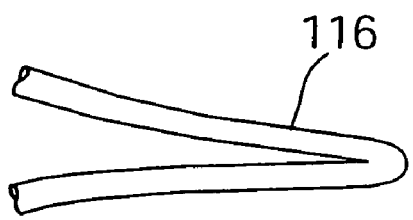
Figure 124:
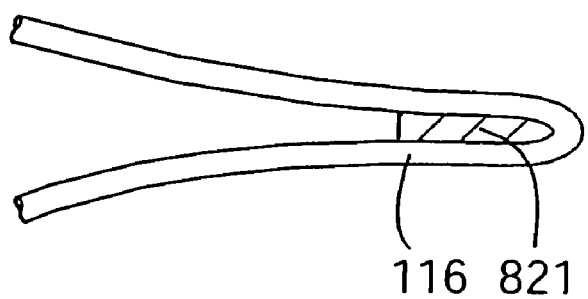
Figure 125:
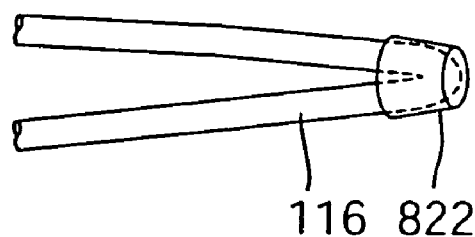
Figure 126:
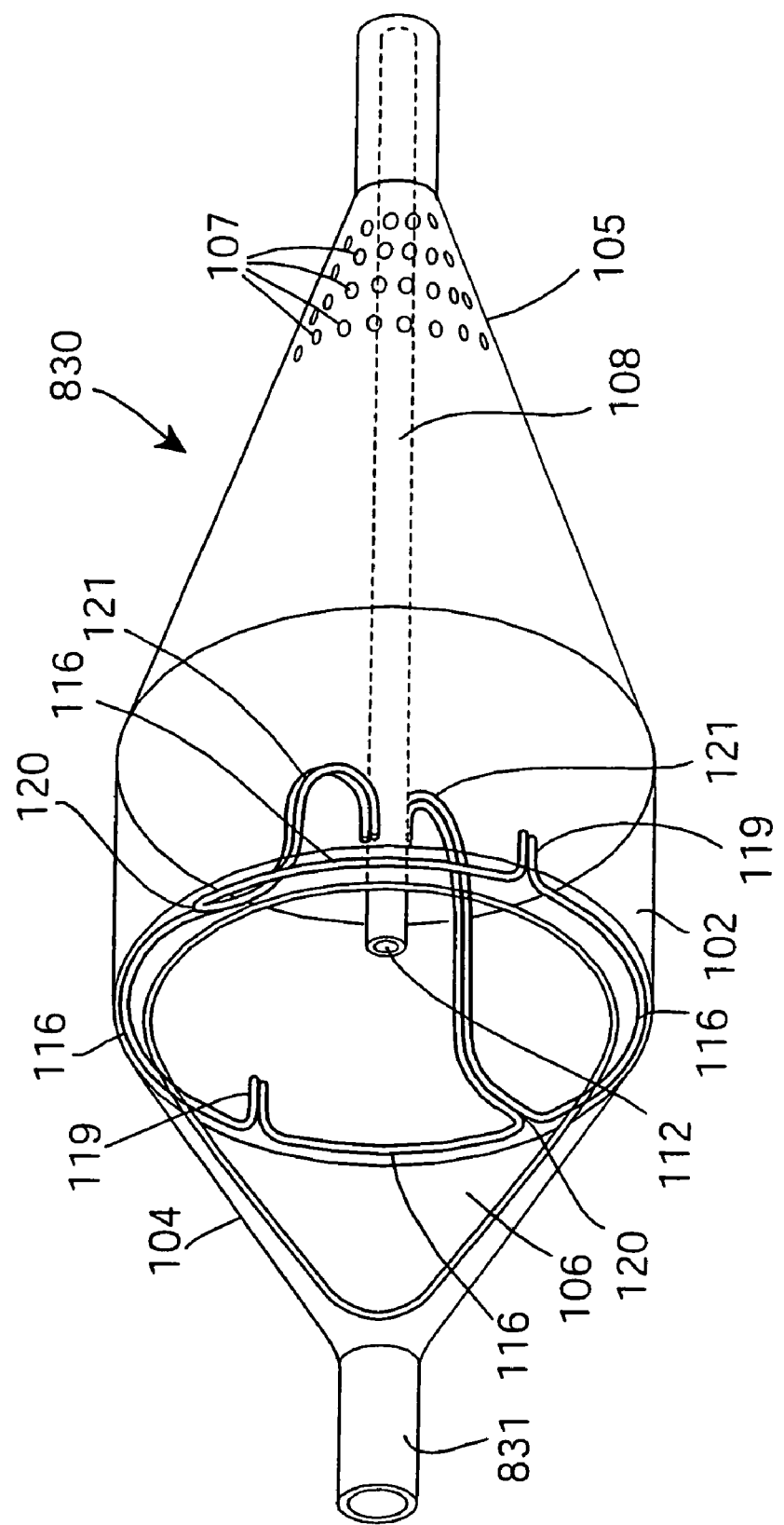
FIG. 126 is a perspective view of another embolic protection device of the invention.
Figure 127:
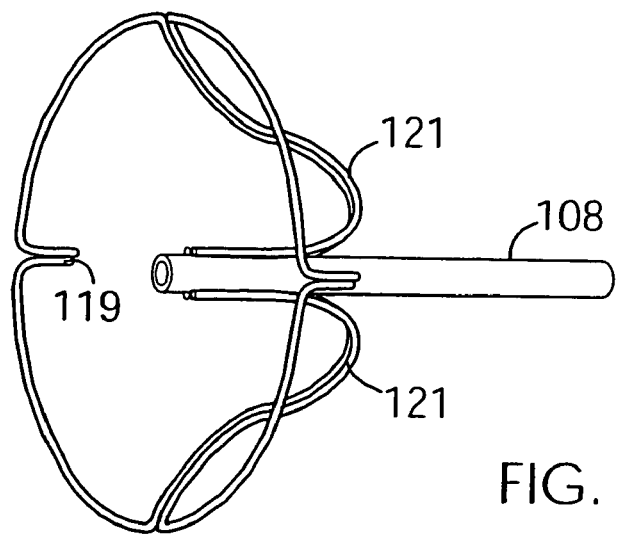
FIG. 127 is a perspective view of the support frame of FIG. 126.

In the case of a single wire 116 bent back on itself to define the support frame, a 180° U-bend at the end of the wire 116 may be formed in multiple strain-temperature stages to prevent plastic deformation of the wire 116 (FIG. 123). A strain relief means 821, such as solder, braze or adhesive, may be provided at the base of the U-bend, as illustrated in FIG. 124. Alternatively, a strain relief tube 822 may be provided at the end of the single wire 116 (FIG. 125).

Referring to FIGS. 126 to 129 there is illustrated another embolic protection filter 830. The wires 116 of the filter support 830 are connected to the inner tube 108 by two legs 121, in this case, which are fixed directly to the inner tube 108. The four round wires 116 of the filter support extend axially proximally and radially outwardly in the two legs 121 to the two opposed distal termination points 120. The wires 116 then separate and extend circumferentially around the support frame until the two opposed proximal termination points 119 are reached. Upon collapse of the filter element, the support frame flips distally over the legs 121 until the filter support is fully collapsed against the inner tube 108 with the legs 121 at the proximal end of the filter support.

Figure 128:
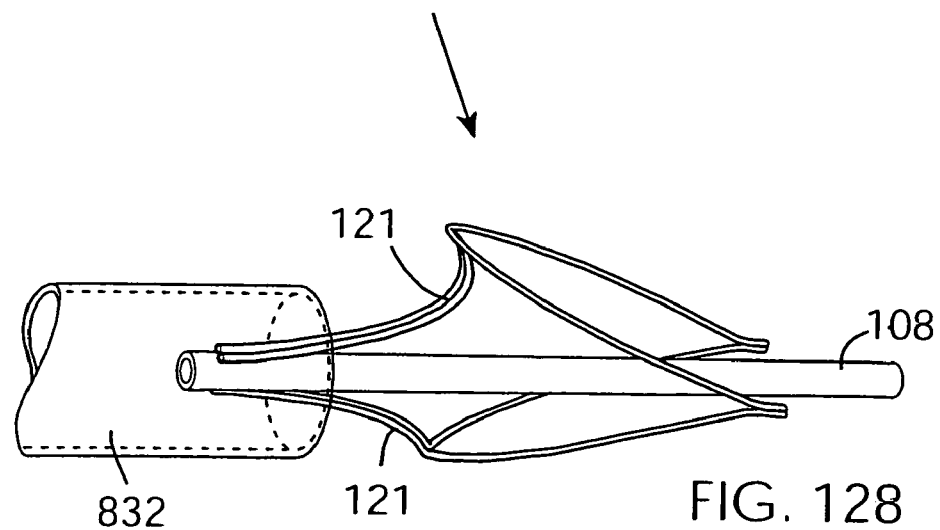
FIGS. 128 and 129 are perspective views illustrating the wrap-down of the frame of FIG. 127.

By locating the support legs 121 distally of the inlet end 104 of the filter body 102, this arrangement minimises the possibility of embolic material becoming caught or hung-up at the inlet openings 106. In this manner, substantially all of the embolic material is retained safely with the filter body 102 for subsequent retrieval from the vascular system using a retrieval catheter 832 as illustrated in FIGS. 128 and 129.

Figure 129:
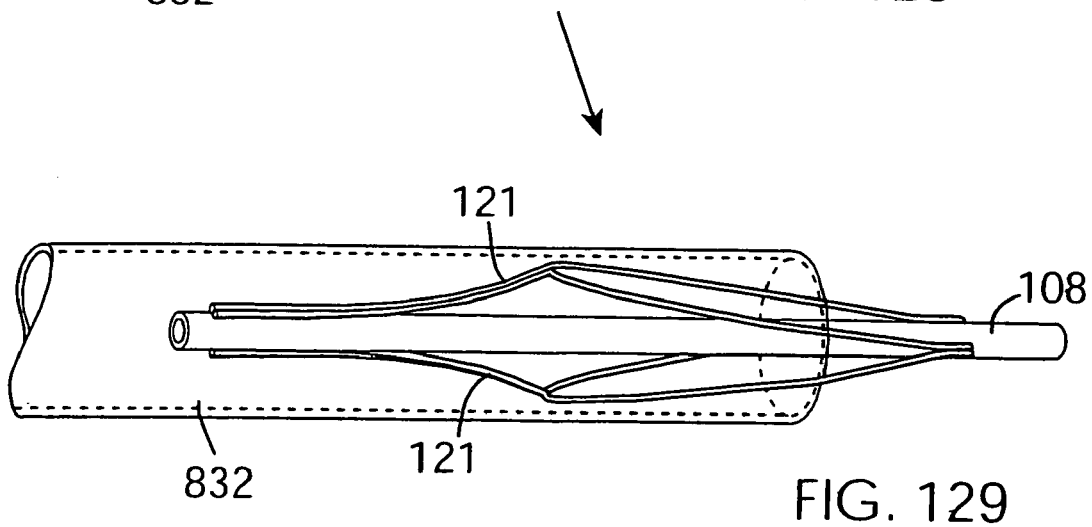
Figure 130:
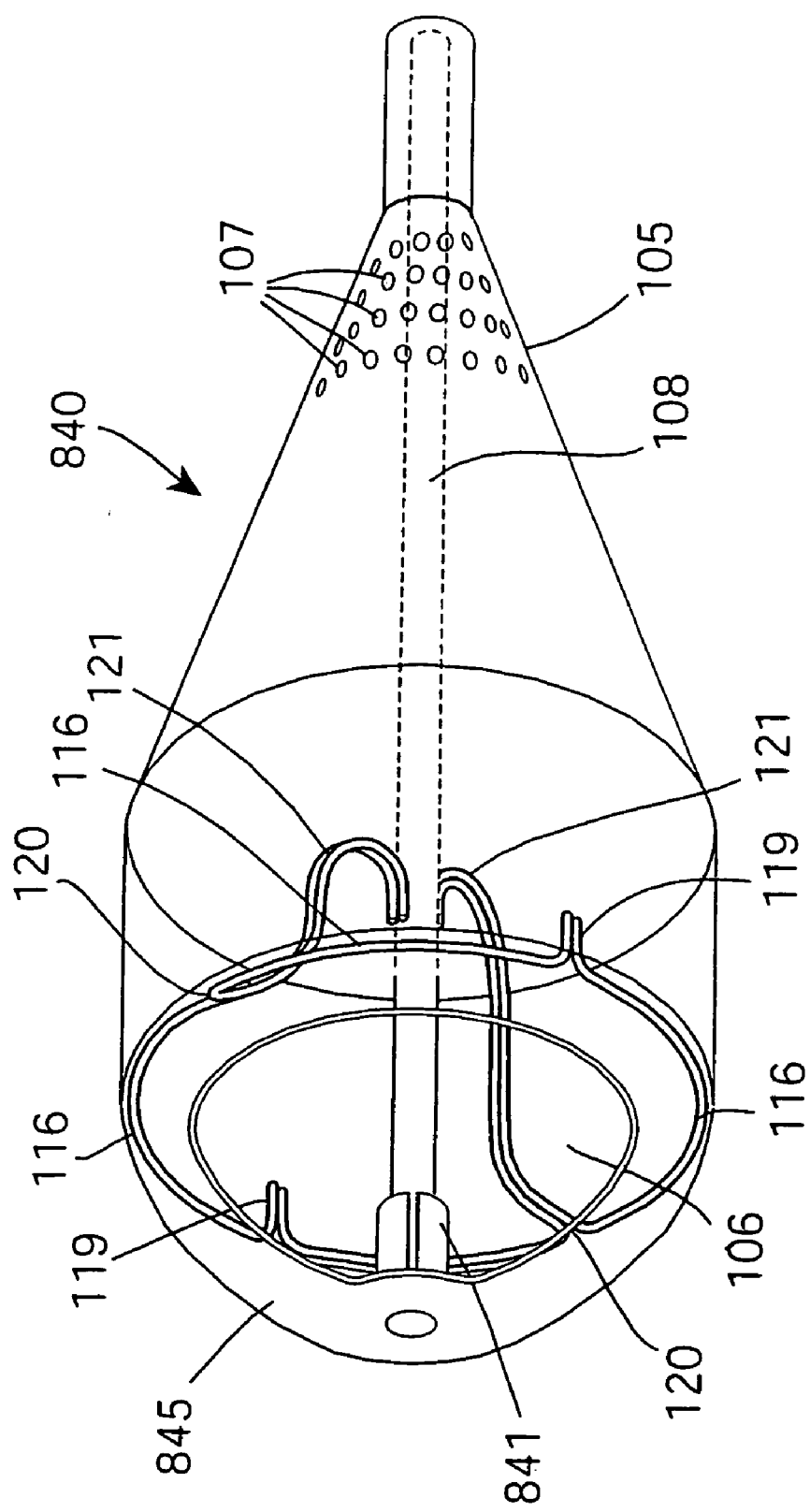
FIG. 130 is a perspective view of another embolic protection device.
Figure 131:
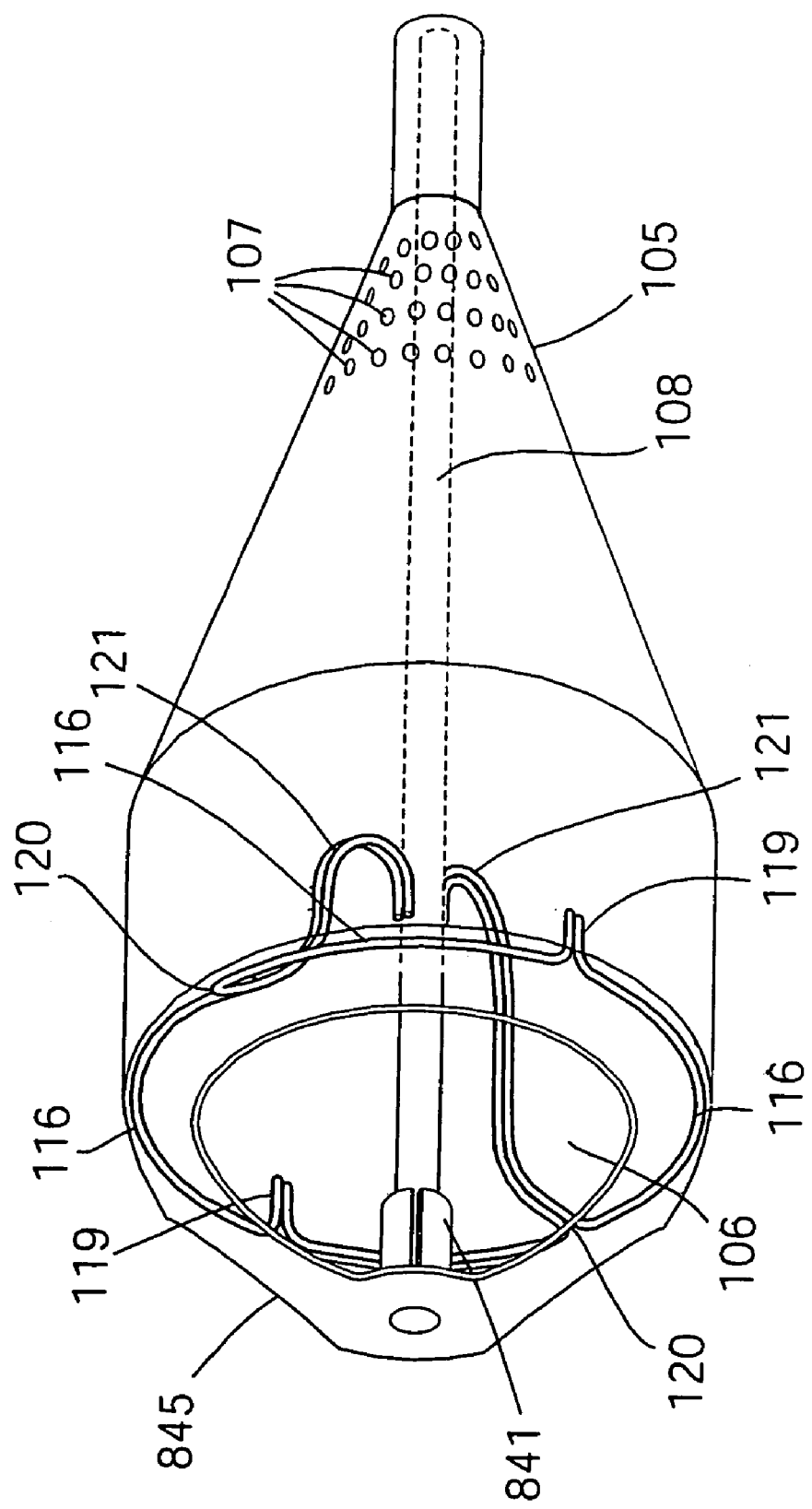
FIG. 131 is a perspective view of a further embolic protection device.

As illustrated with the filter 840 of FIGS. 130 and 131, a proximal neck 841 of the filter body may be inverted to extend distally rather than proximally, as is the case with the filter element of FIG. 129. This arrangement reduces the overall longitudinal length of the filter element, and thus the filter element may be deployed and retrieved with a shorter "parking space" in the vasculature.

Figure 132:
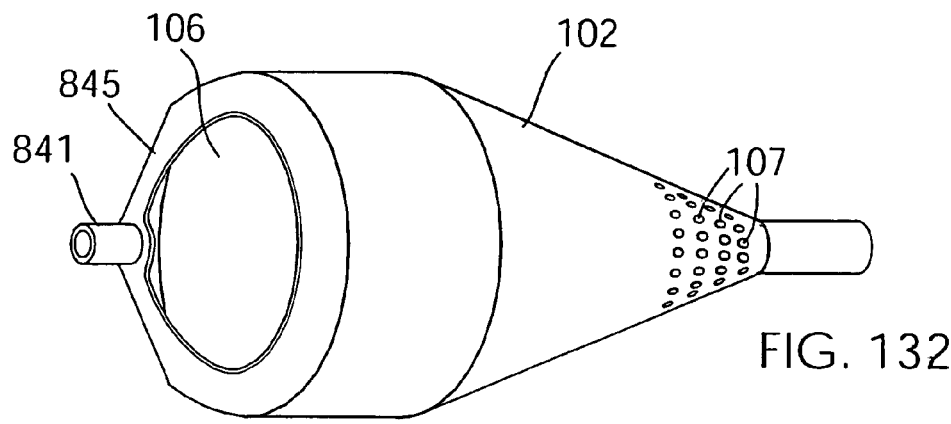
FIGS. 132 to 134 illustrate steps in the method for forming embolic protection devices of FIG. 131.
Figure 133:
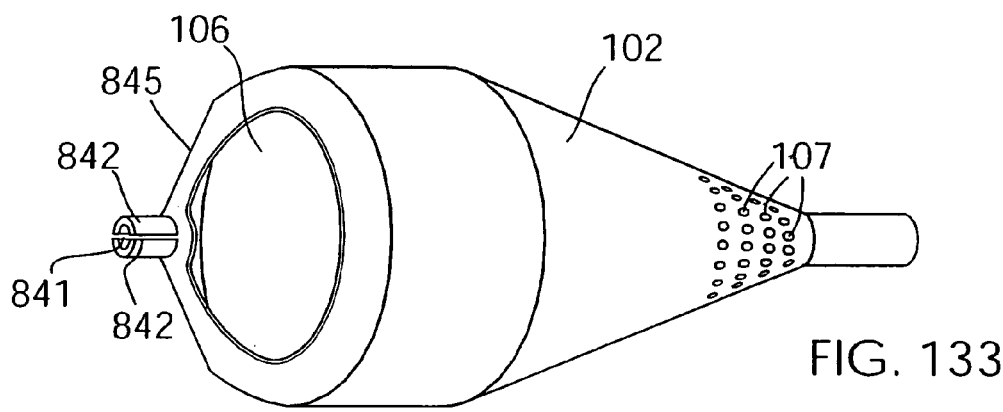
Figure 134:
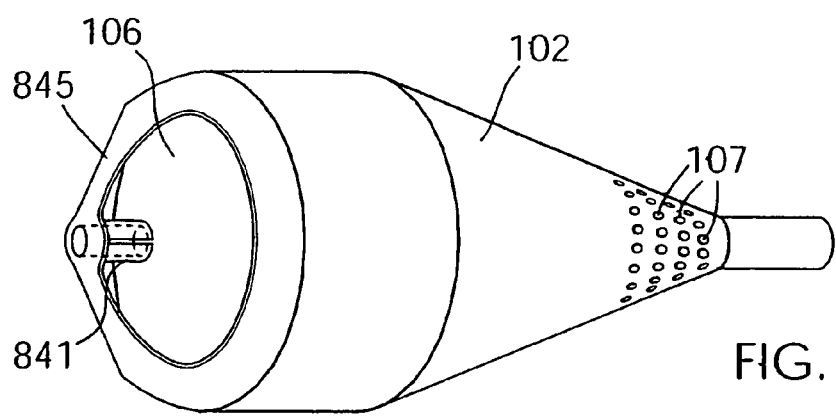

FIGS. 132 to 134 illustrate the process of inverting the proximal neck 841. The neck 841 is split along each side 842 (FIG. 133), and the neck 841 is then pushed distally into the interior of the filter body (FIG. 134).

In addition, the longitudinal length of the filter element of FIG. 130 is further shortened by providing a hemi-spherically shaped proximal nose 845 instead of a conical nose, as is the case with the filter element of FIG. 129. Furthermore, the overall crossing profile of the filter element is reduced by means of the hemi-spherical nose 845.

Figure 135:
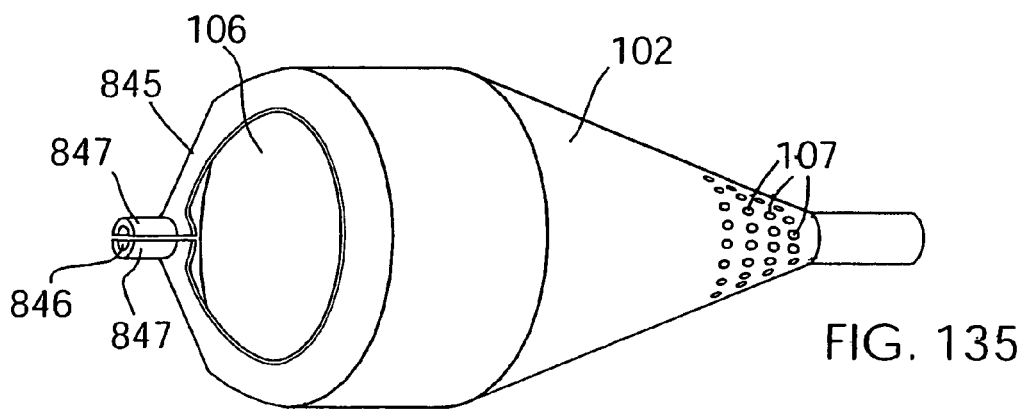
FIG. 135 is a perspective view of another embolic protection device.

Referring to FIG. 135 there is illustrated a filter with a proximally extending neck 847 which is split into two parts 847.

Figure 136:
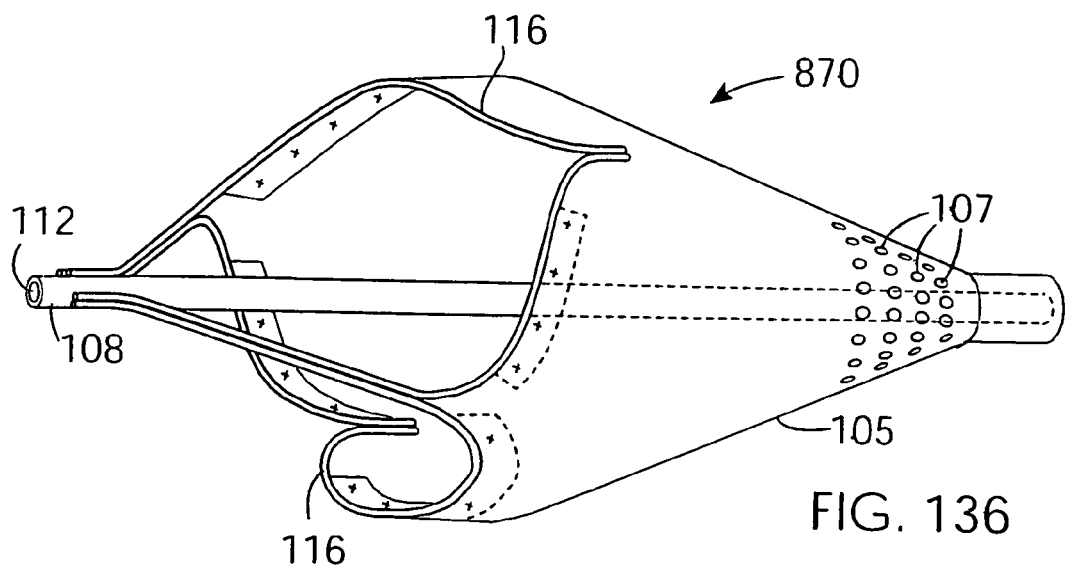
FIG. 136 is a perspective view of an embolic protection device.
Figure 137:
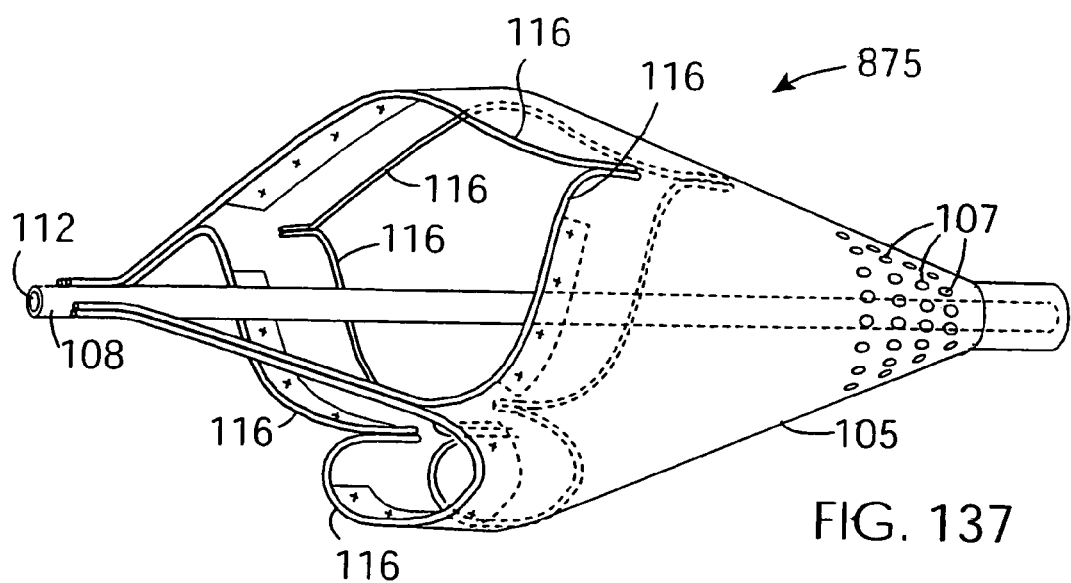
FIG. 137 is a perspective view of another embolic protection device.

Referring to FIGS. 136 and 137 there is illustrated a filter 870 in which the filter body is connected directly to the frame by means of folded filter seams.

FIG. 137 shows a variant filter 875 in which a second frame provides additional body support to the filter.

Figure 138:
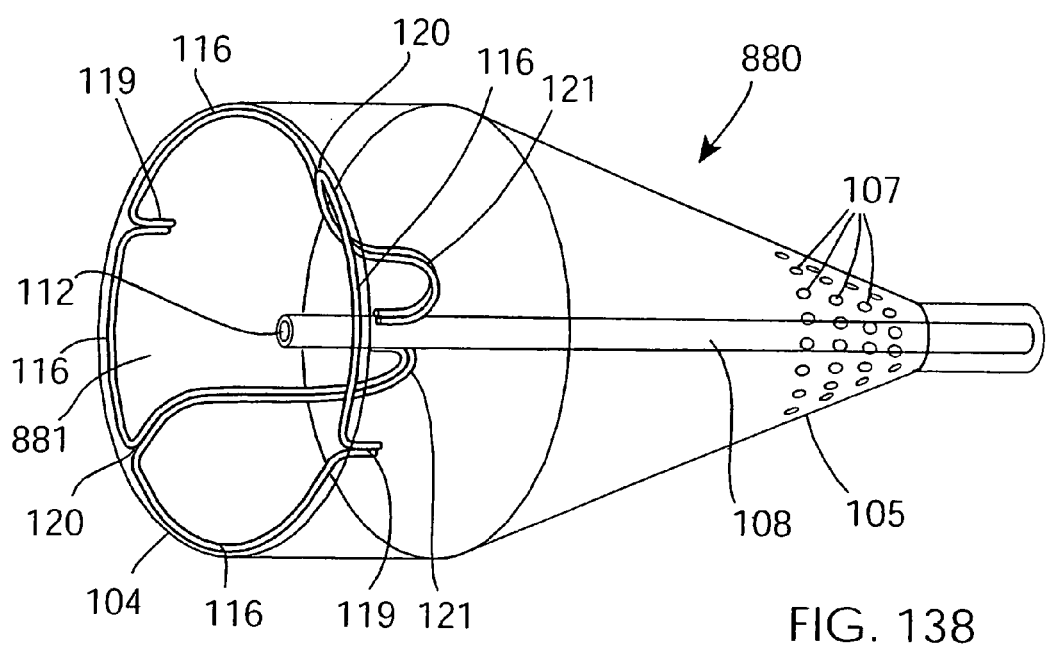
FIG. 138 is a perspective view of a further embolic protection device.

Referring to FIG. 138, there is illustrated another filter element 880, with a filter body which, in this case, has a single, large inlet opening 881 defined at the inlet end 104. This arrangement further minimises the possibility of any embolic material becoming caught or hung-up on any parts of the filter element at the inlet end 104. This arrangement also further reduces the overall longitudinal length of the filter element.

Figure 139:
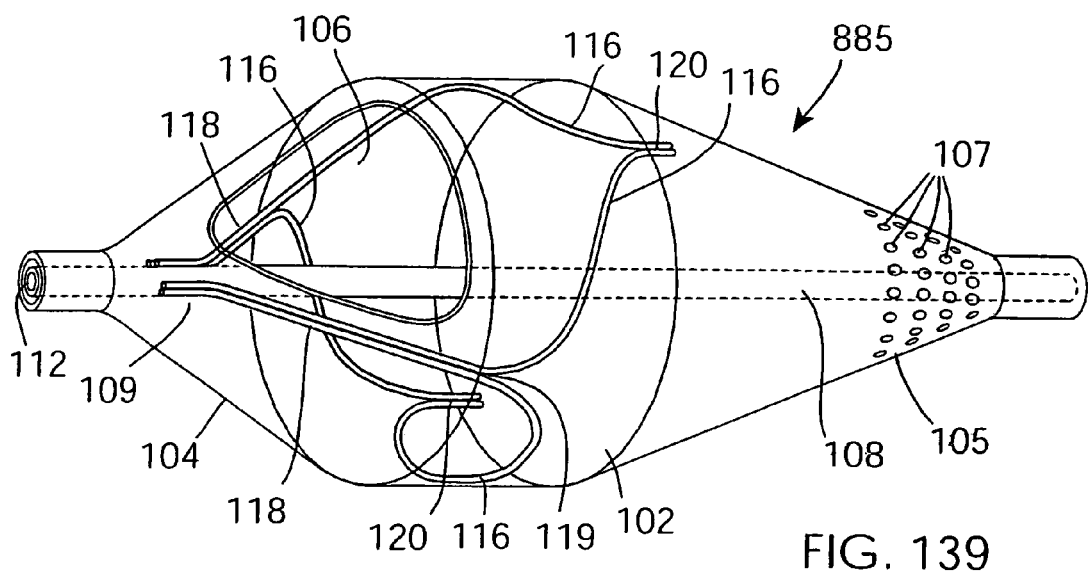
FIG. 139 is a perspective view of another embolic protection device.

FIGS. 139 and 140 illustrate a further filter element 885, in which the proximal end 9 of the filter support is fixed to the inner tube 108, while the distal end 110 of the filter support remains unconnected to the inner tube 108. The filter support comprises four round wires 116 which extend axially and radially outwardly in two legs 118 from the proximal end 109 to the proximal termination points 119. At the proximal termination points 119, the wires 116 separate and extend circumferentially around the support frame until the two distal termination points 120 are reached. The proximal termination points 119 are circumferentially offset by 90° from the distal termination points 120.

The proximal end 109 of the filter support 103 is fixed to the inner tube 108, and the distal end 110 of the filter support 103 is fixed to a sleeve 111 which is slidable over the inner tube 108. Upon collapse of the filter element, the proximal end 109 of the filter support 103 remains fixed relative to the inner tube 108, and the distal sleeve 111 slides over the tube 108, until the filter support 103 is fully collapsed against the inner tube 108. In this collapsed position, the filter support 103 is axially elongated relative to the expanded position.

The filter support 103 is illustrated in FIG. 142. The filter support 103 comprises two round wires 116 which extend from the proximal end 109 to the distal end 110. The wires 116 extend together axially and radially outwardly in a leg 118 from the proximal end 109, where the wires 116 are fixed to the inner tube 108, to a central support hoop 115. The junction of the leg 118 with the support hoop 115 is referred to in this specification as the proximal termination point 119.

At the proximal termination point 119, the wires 116 separate, and extend circumferentially around the support hoop 115 until a symmetrical distal termination point 120 is reached. In this way, the two wires 116 define the support hoop 115.

At the distal termination point 120, the wires 116 regroup into a leg 121 which extends axially, and then axially and radially inwardly to the sleeve 111 to which the wires 116 are fixed.

The path of the two wires 116 around the support hoop 115 together define a cell 116 which forms a complete loop, as illustrated in FIG. 142. This arrangement of the circumferential looped cell 117 ensures that in the expanded position, the filter body 102 will be supported by the support hoop 115 in circumferential apposition with the interior wall of the vasculature.

The length of each wire 116 around the cell 117 is equal. At the proximal and distal termination points 119, 120, the wires 116 are fixed to each other, and extend generally axially and parallel in a bi-filar arrangement.

As the filter support 103 collapses down against the inner tube 108, the wires 116 around the cell 117 become torqued. This torqueing action is similar to the process of elongation of a coiled spring.

Because the support frame 115 is defined by round wires 116, the torque developed in each wire 116 will be evenly distributed along the length of each wire 116. In addition, the bi-filar connection of the wires 116 to each other at the termination points 119, 120 further assists in torque distribution along the wires 116.

Thus, collapse of the filter support 103 does not induce high, localised stresses in the filter support 103. In this way, the filter support 103 may be constructed of wires 116 of a small cross-sectional area which will collapse down to a very low profile.

Furthermore the collapsed filter element with small wires 116 has greater flexibility for ease of advancement of the filter element through the vascular system.

As illustrated in FIG. 142, the proximal termination point 119 is circumferentially offset by 180° from the distal termination point 120.

The wires 116 are preferably of a self-expanding material, such as Nitinol, and the inner tube 108 is preferably of gold. This arrangement provides for radiopacity.

In use, the filter element is collapsed down and loaded into a delivery catheter with an associated torqueing of the wires 116 around the cell 117. The filter element is then delivered through a vasculature fixed to or over a guidewire using the delivery catheter until the filter element is located at a desired site in the vasculature.

By moving the delivery catheter proximally relative to the filter element, the filter element is deployed out of the delivery catheter at the desired site in the vasculature. The filter support 103 expands radially outwardly to support the filter body 102 in circumferential apposition with the interior wall of the vasculature. In the fully expanded position, the wires 116 of the support frame 115 are substantially free of torque.

The site of deployment of the filter element in the vasculature is typically downstream of a treatment site, such as a region of stenosis in the vasculature. During the performance of a treatment procedure, the filter element captures and safely retains any embolic material in the blood stream within the filter body 102.

After completion of the treatment procedure, the filter element is collapsed down and retrieved into a retrieval catheter with any retained embolic material within the filter body 102. The wires 116 around the support frame 115 are again torqued during collapse.

The retrieval catheter is then withdrawn from the vasculature with the filter element within the retrieval catheter.

Referring to FIGS. 142(a) and 142(b) there is illustrated a lower portion and a top view of a modified support frame similar to FIG. 142 in which the loops defined by the wires 115 are offset at point 120. This offset could also be applied to point 119. Such a design may be of benefit in broadening the area of circumferential apposition and sealing provided by the filter.

Figure 143:
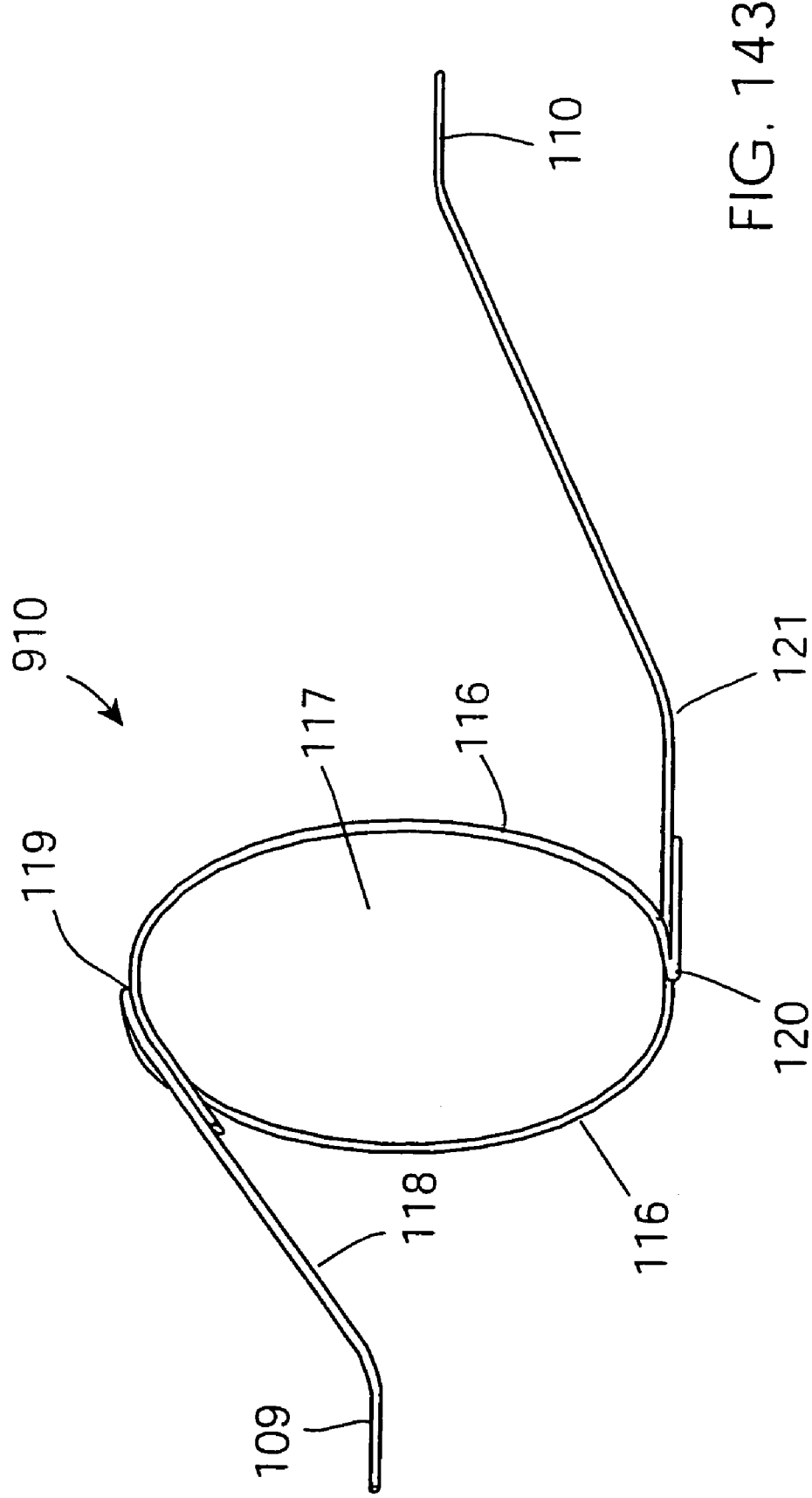
FIG. 143 is a perspective view of an alternative support frame.

Referring to FIG. 143 there is illustrated a support frame 910 similar to that of FIG. 142 except that in this case the distal and proximal legs 121, 118 are defined by a single wire, the second wire extending only a short distance distally or proximally from the distal and proximal termination points respectively.

Figure 144:
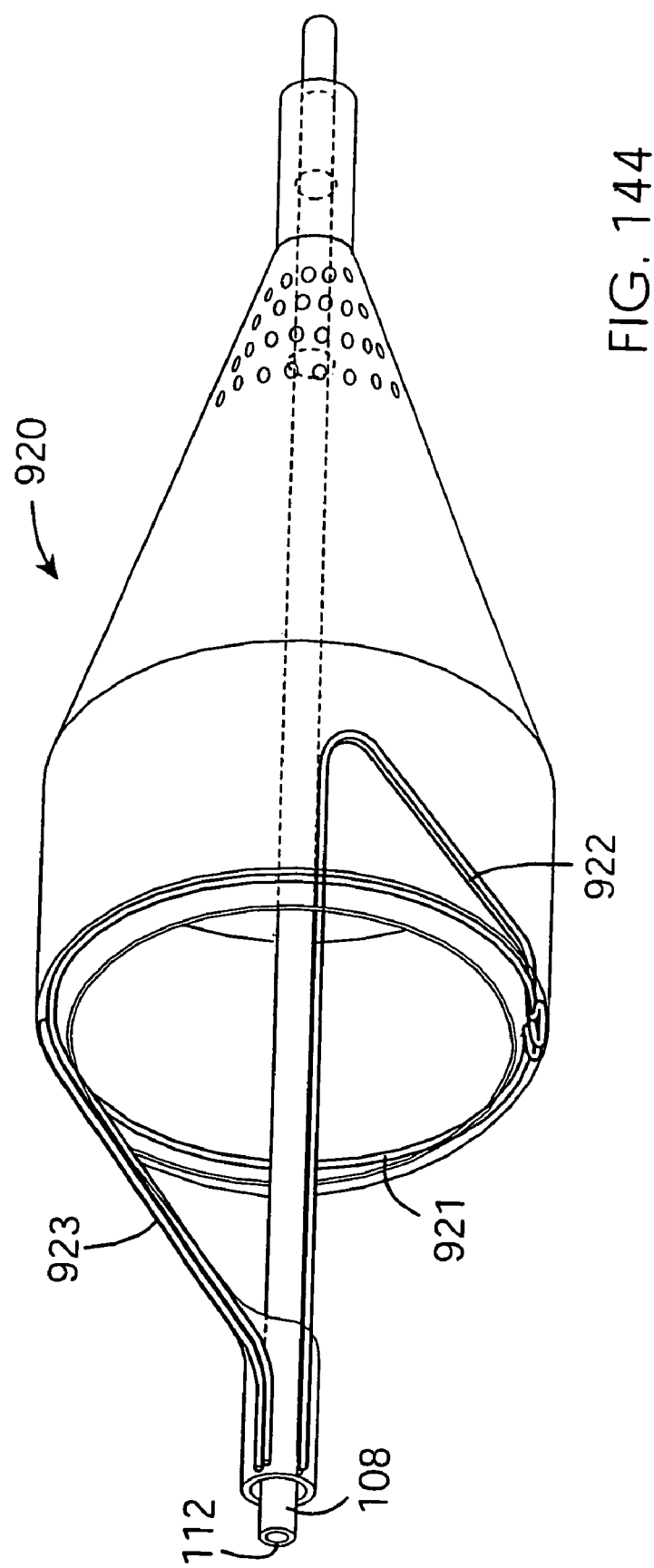
FIG. 144 is a perspective view of an embolic protection device with a single loop support frame.

Referring to FIG. 144 there is illustrated another embolic protection filter 920 which comprises a single hoop support frame 921 with additional wire support arms 922, 923. In this case the distal support leg is connected to the proximal end of the carrier. Thus additional support is provided to the hoop without any impact on the wrapped length of the device.

Figure 145:
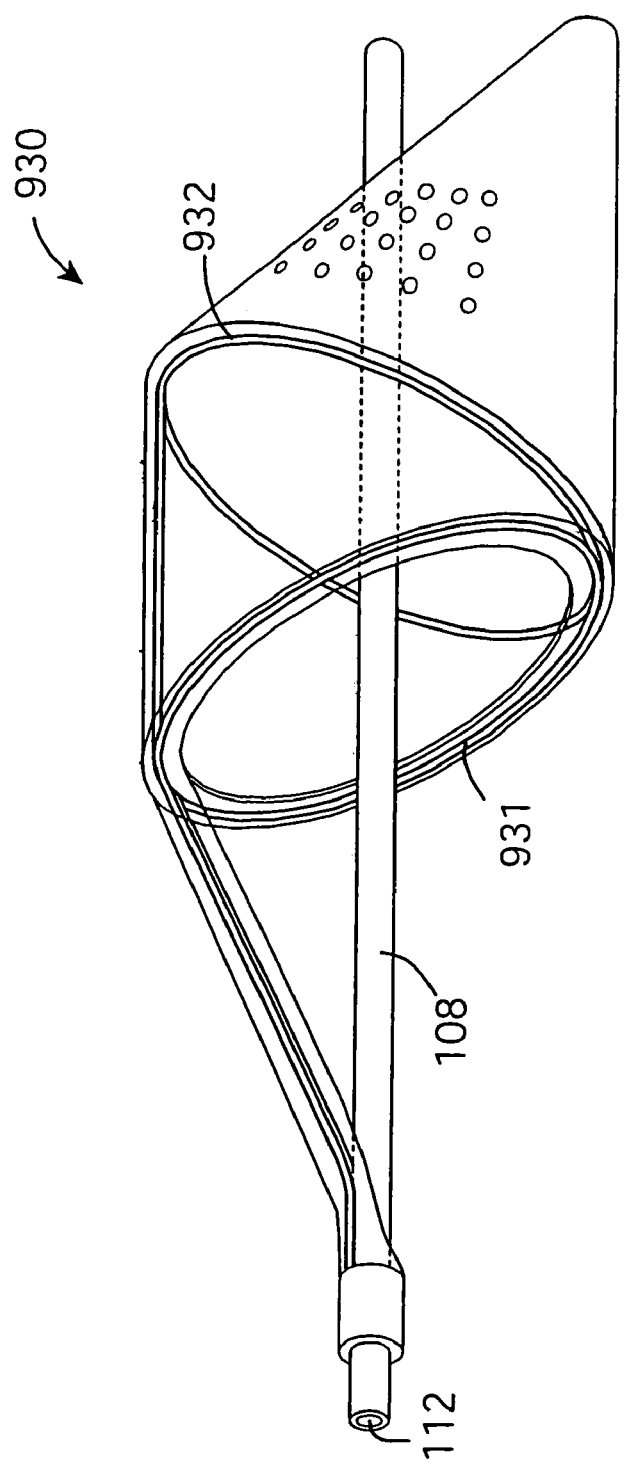
FIG. 145 is a perspective view of another embolic protection device.

Referring to FIG. 145 there is illustrated a further embolic protection filter 930 comprising support hoops 931, 932 which are offset.

Figure 146:
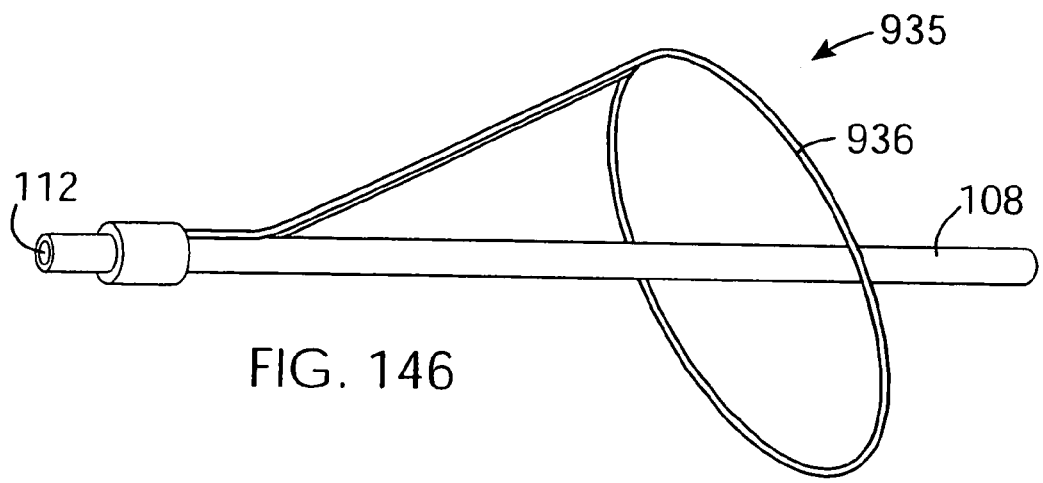
FIGS. 146 to 148 are perspective views of support frames of the invention.
Figure 147:
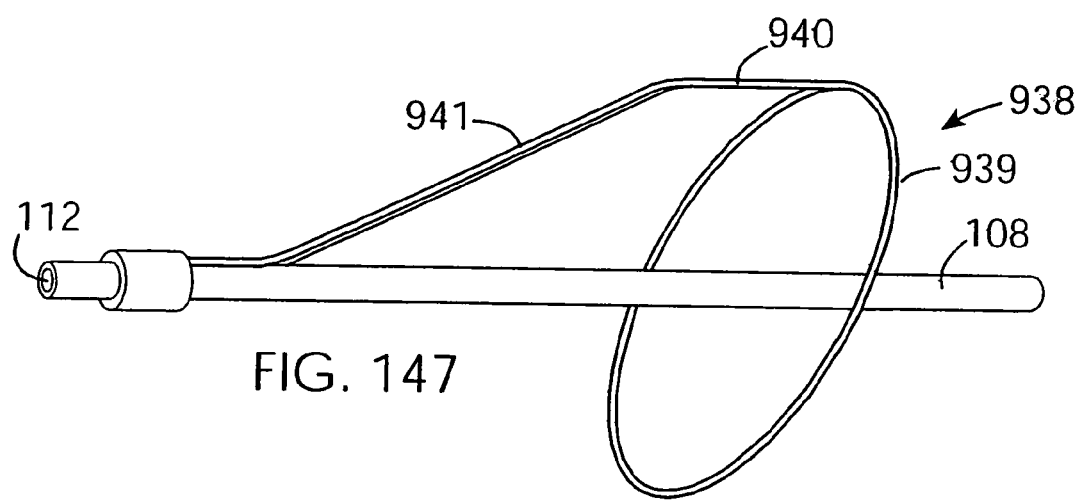
Figure 148:
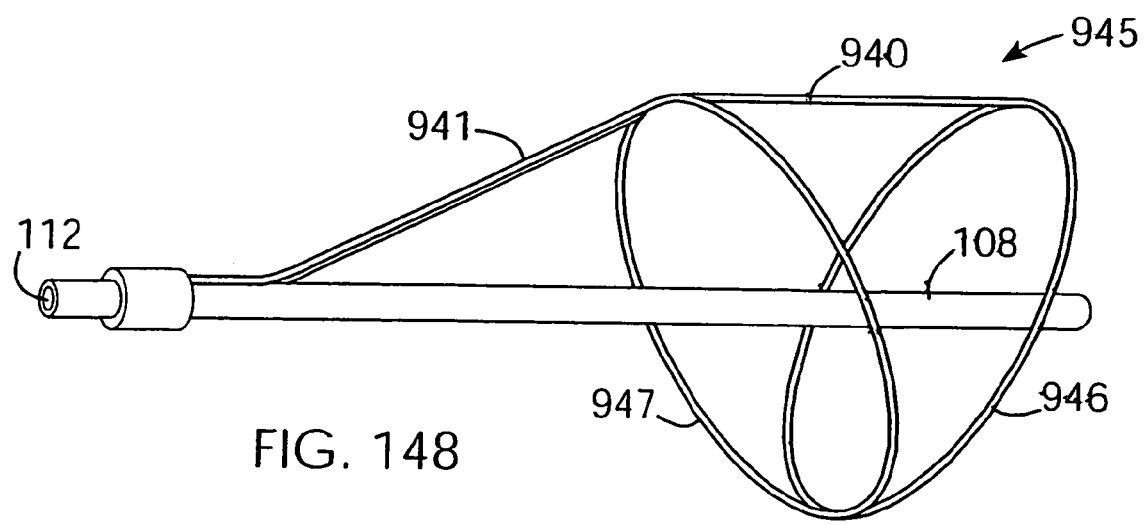

Referring to FIGS. 146 to 148 there are illustrated various filter frames comprising a wire support hoops which may have strain distribution features and/or tethers as described above.

The frame 935 of FIG. 146 comprises a single wire offset hoop 936. The frame 938 of FIG. 147 is preferred because parking space is minimised while facilitating wrap-down. It will be noted the support comprises an offset wire support hoop 939 with an axially extending proximally extending wire section 940 and an inwardly extending support arm 941. The frame 945 of FIG. 148 is similar to that of FIG. 147 except that there are two oppositely directed offset hoops 946, 947 similar to the frame used in the filter of FIG. 145.

Another support frame 950 is illustrated in FIGS. 149 to 150 which is again of wire and includes strain distributing loop features 951 which may be of any suitable type as described above and exemplified in FIGS. 150 and 151.

The support frame 960 of FIGS. 152 and 153 again has an offset hoop 961 which can wrap down as illustrated in FIG. 153.

Figure 154:
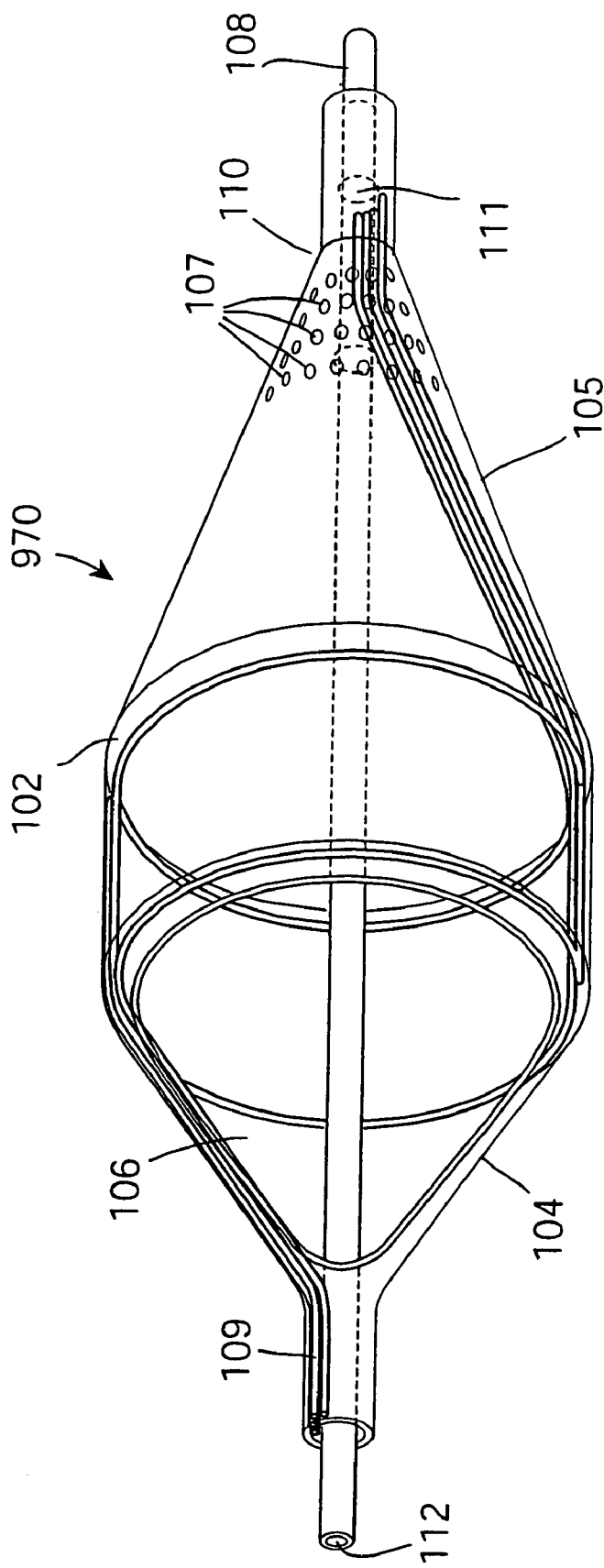
FIG. 154 is a perspective view of another embolic protection device.
Figure 155:
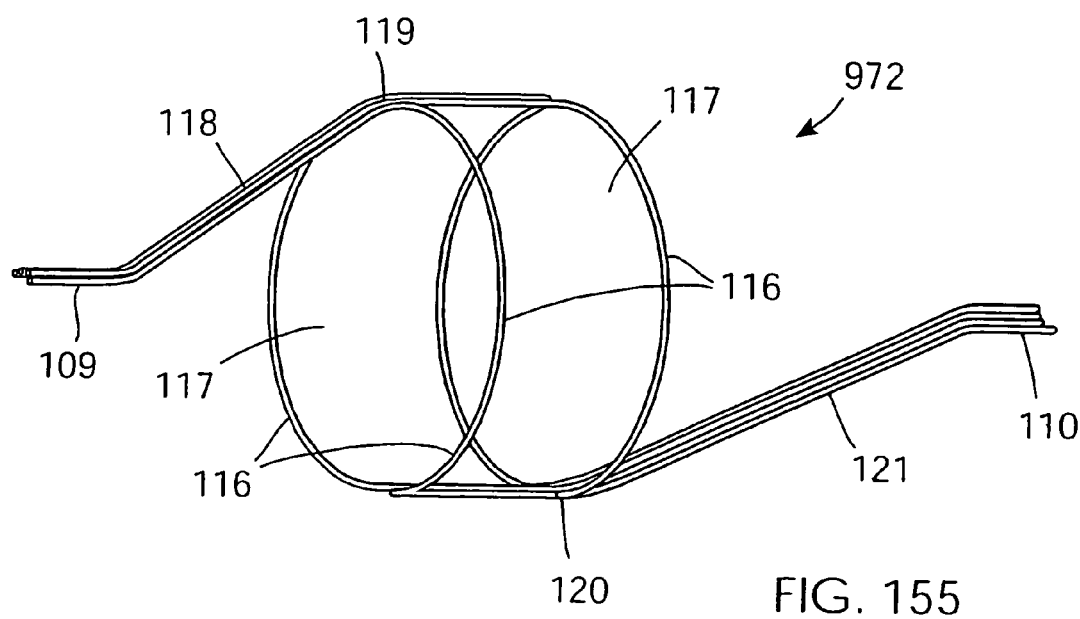
FIG. 155 is a perspective view of a support frame of the device of FIG. 154.

Referring to FIGS. 154 and 155, there is illustrated another filter element 970, in which the filter support 972 comprises four round wires 116. At the proximal termination point 119, two of the wires 116 extend circumferentially around the support frame 115 to define a first cell 117, and the other two wires 116 extend axially and then extend circumferentially around the support frame to define a second cell 117.

In this manner, the wires 116 define two axially spaced-apart cells 117, each cell 117 forming a complete loop, as illustrated in FIG. 155. This arrangement ensures that in the expanded position, the filter body 102 will be supported by the support frame in tubular apposition with the interior wall of the vasculature. The tubular apposition further minimises the possibility of any flow path for blood occurring between the filter body 102 and the vasculature wall to bypass the filter element. At the distal termination point 120, all four wires 116 regroup into leg 121.

Figure 156:
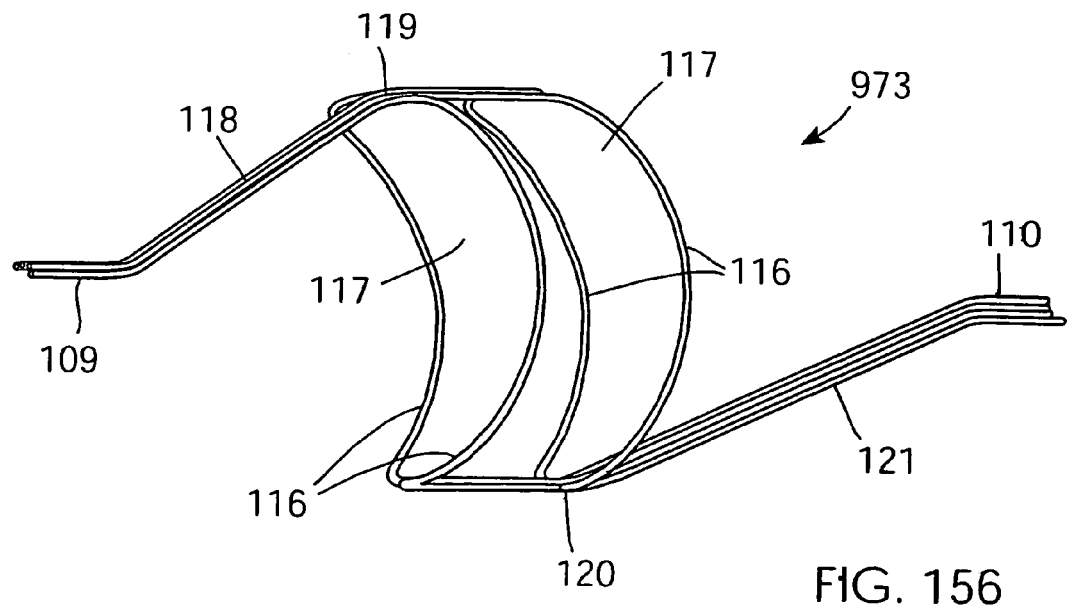
FIG. 156 is a perspective view of an alternative support frame for the device of FIG. 155.

It will be appreciated that as the wires 116 extend circumferentially around the support frame 115, the wires 116 may also extend partially axially, so that the defined cell 117 partially slopes axially. Furthermore, the wires 116 may be at least partially of an arcuate shape, as illustrated in the support frame 973 of FIG. 156. In either case, the sloping or arcuate configuration of the wires 116 increases the contact area between the wires 116 and the filter body 102, and in this way, the supporting force exerted by the wires 116 on the filter body 102 is more evenly distributed. This arrangement minimises any trauma experienced by the vasculature due to the apposition of the filter element with the vasculature.

Figure 157:
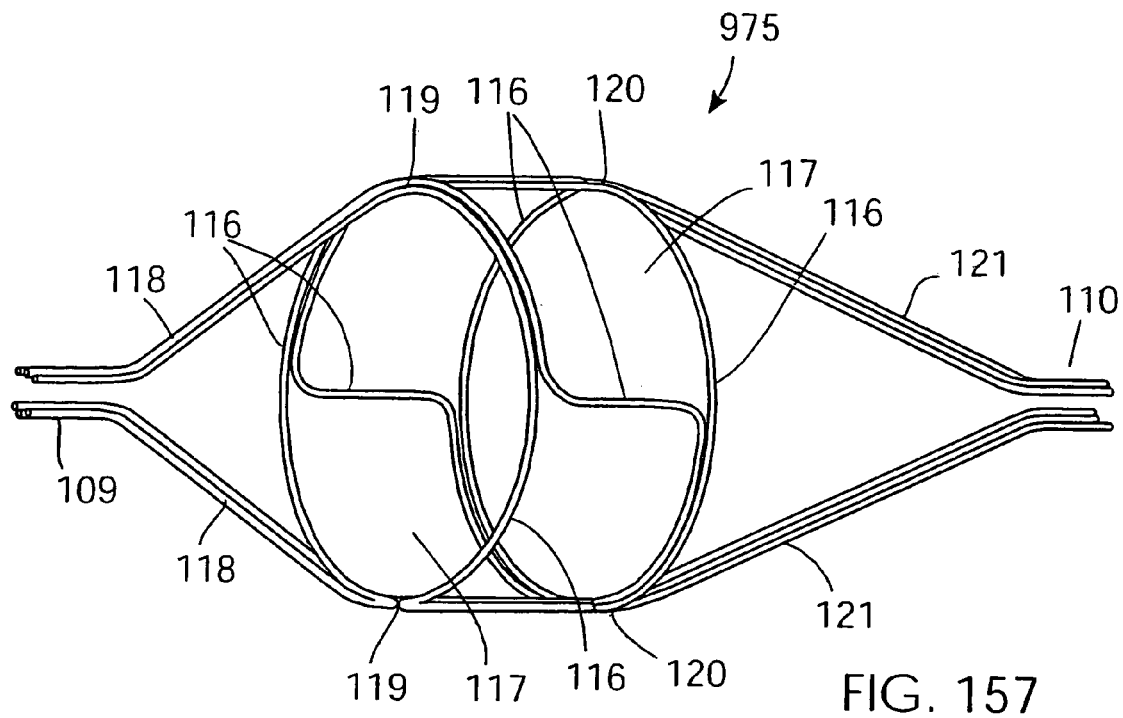
FIGS. 157 and 158 are perspective views of alternative support frames.

FIG. 157 illustrates another filter support 975, which is similar to the filter support of FIGS. 154 and 155, and similar elements in FIG. 157 are assigned the same reference numerals. In this case, the filter support comprises six round wires 116. The wires 116 extend axially and radially outwardly in two legs 118 from the proximal end 109 to two opposed proximal termination points 119. As illustrated in FIG. 157, the wires 116 are arranged to define two axially spaced-apart, complete loop cells 117. In addition, two of the wires 116 act as axial bridges to connect the two cells 117. At the distal termination points 120, the wires 116 regroup into two legs 121. The proximal termination points 119 are circumferentially aligned with the distal termination points 120, in this case.

Figure 158:
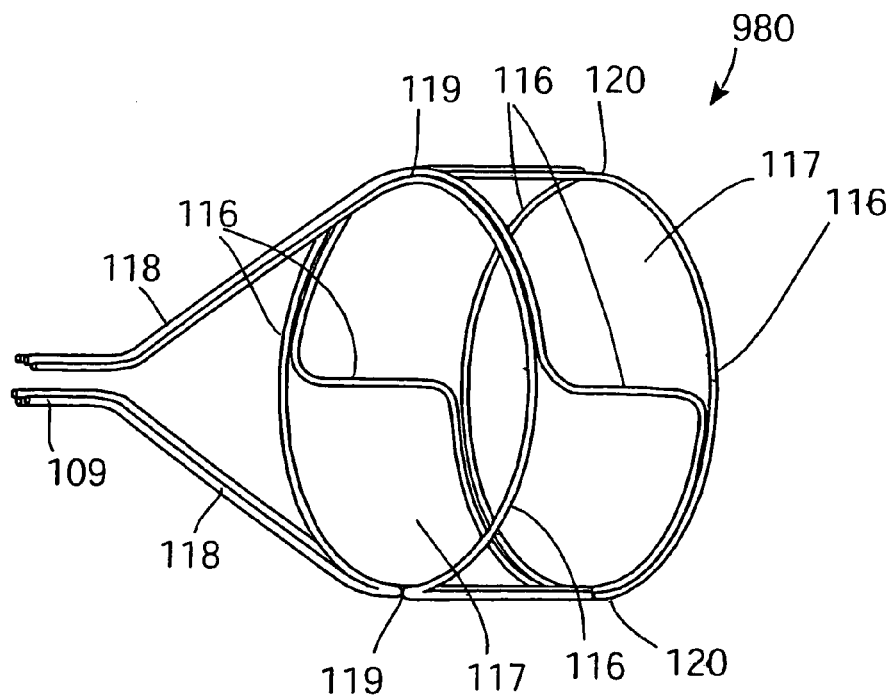

The support frame 980 of FIG. 158 is similar to that of FIG. 157 except that in this case there are no proximal support arms with consequential reduced filter length.

Figure 159:
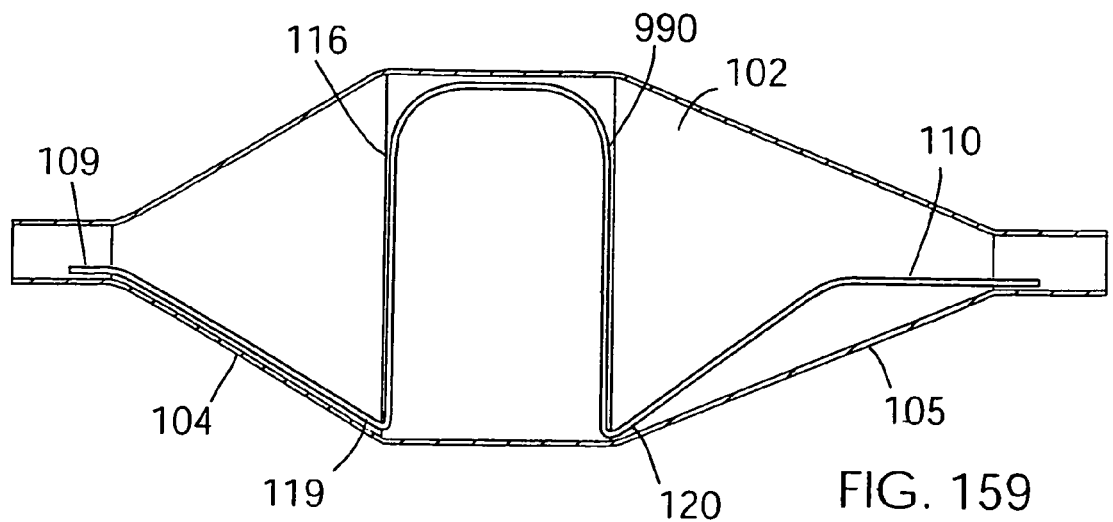
FIGS. 159 to 161 are side, plan and perspective views of another embolic protection device.
Figure 160:
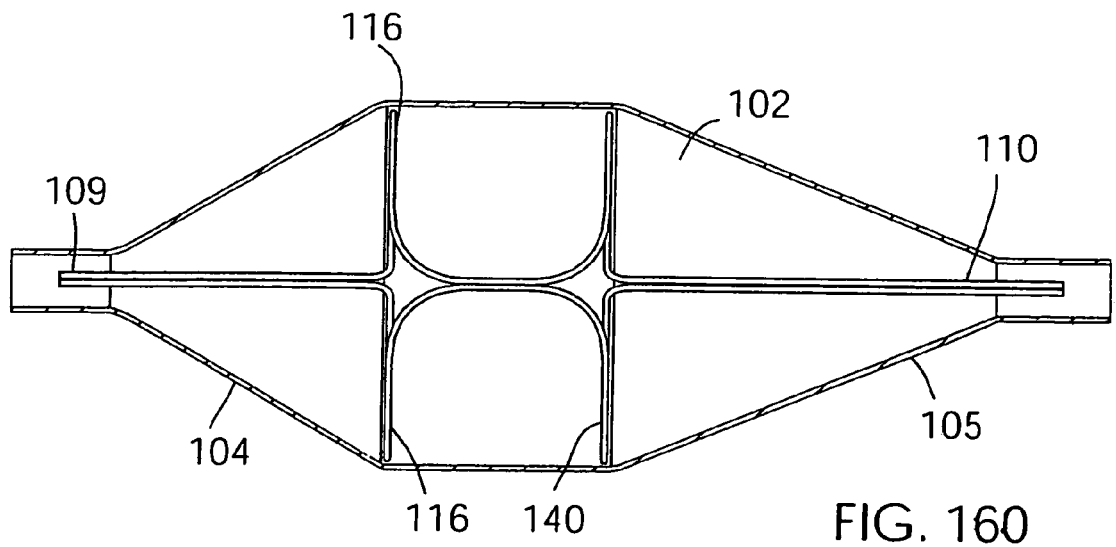
Figure 161:
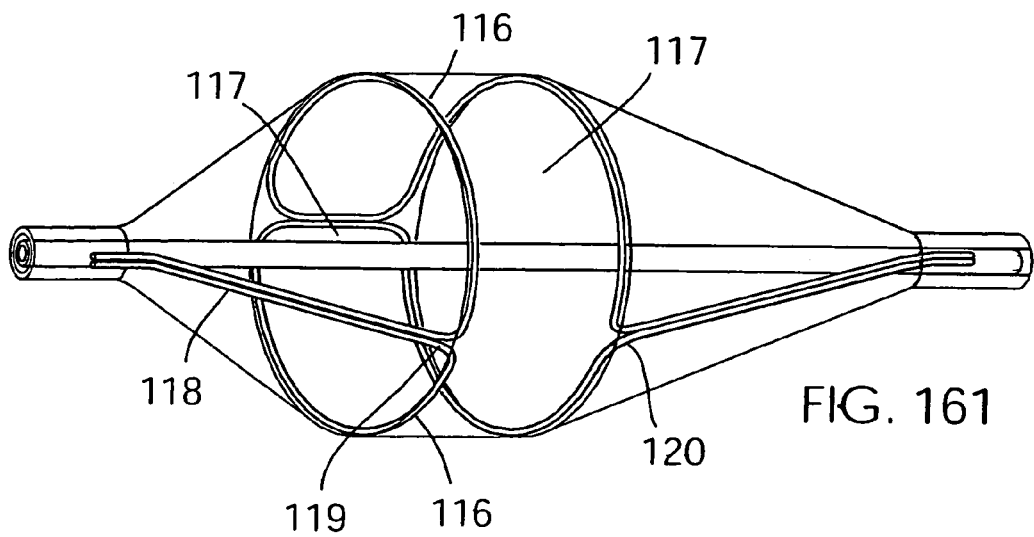
Figure 162:
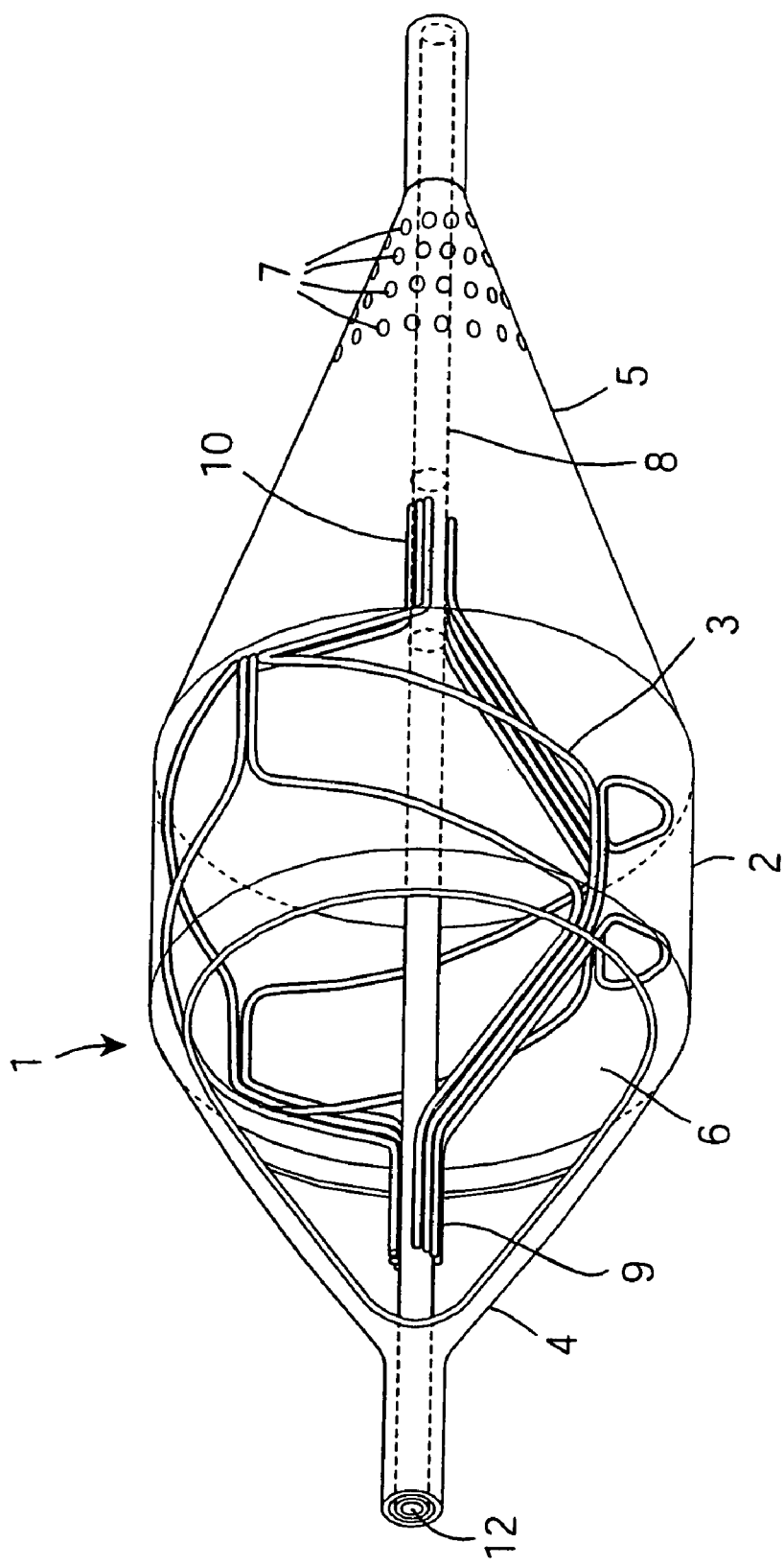
FIG. 162 is a perspective view of an embolic protection device according to the invention.
Figure 163:
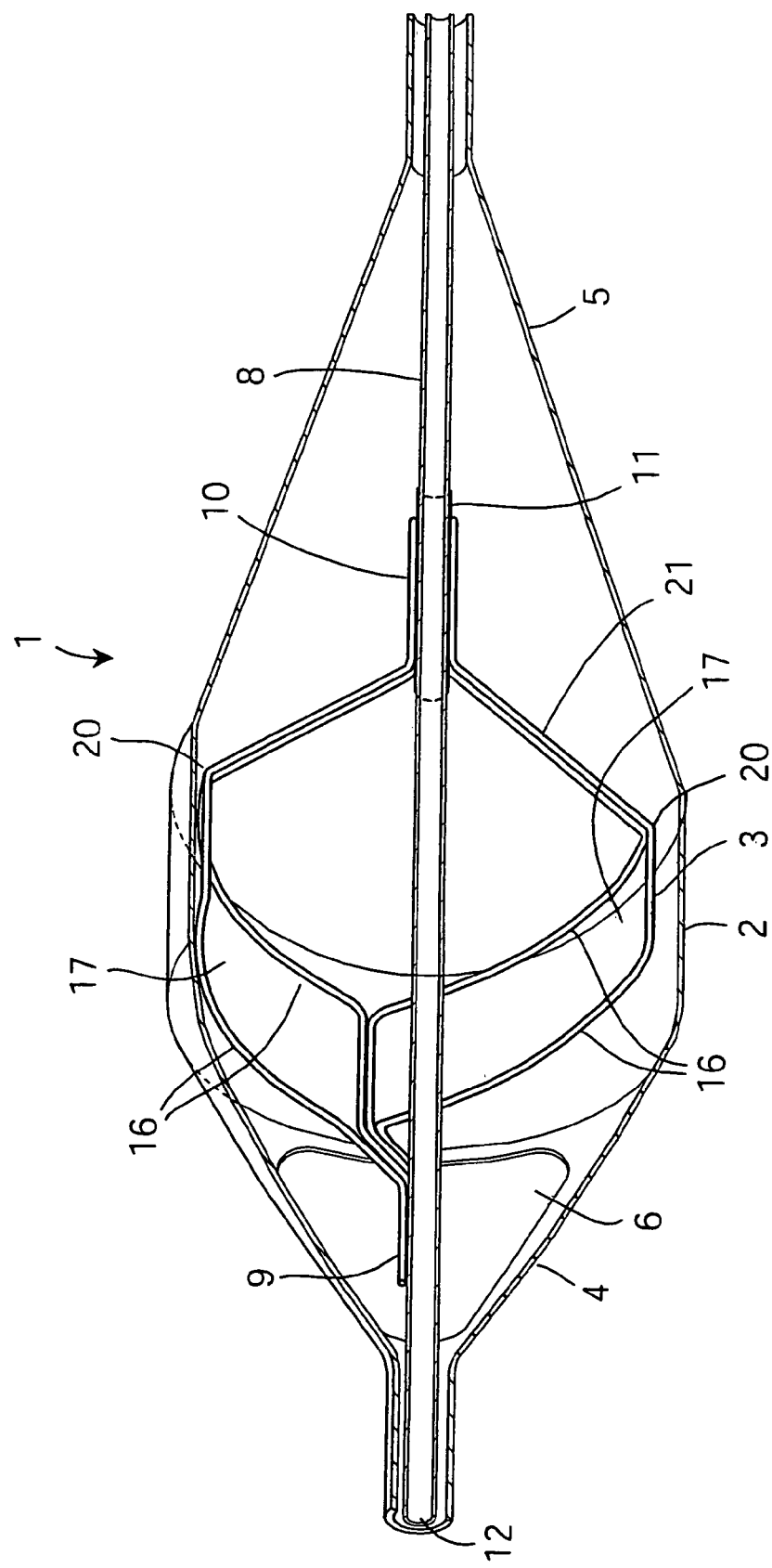
FIG. 163 is a cut-away, perspective view of the embolic protection device of FIG. 162.

Referring to FIGS. 159 to 161, there is illustrated another filter support 990, which is similar to the filter support of FIGS. 154 and 155, and similar elements are assigned the same reference numerals. In this case, the filter support 990 comprises only two round wires 116. The wires 116 extend together axially and radially outwardly in a single leg 118 from the proximal end 109 to the proximal termination point 119. The wires 116 then separate and extend circumferentially around the support frame 115 to define the first cell 117. The wires 116 extend axially, and then circumferentially around the support frame 115 to define the second cell 117. At the distal termination point 120, the wires 116 regroup into a single leg 121.

As illustrated in FIG. 161, the proximal termination point 119 is circumferentially aligned with the distal termination point 120.

Referring to the drawings, and initially to FIGS. 162 to 169 thereof, there is illustrated an embolic protection device according to the invention. The embolic protection device comprises a collapsible filter element 1 for delivery through a vascular system of a patient.

The filter element 1 comprises a collapsible filter body 2 and a filter support 3 for the filter body 2, and an inner tube 8, around which the filter support 3 is mounted.

The filter body 2 has an inlet end 4 and an outlet end 5. The inlet end 4 has one or more, and in this case two, large inlet openings 6 which are sized to allow blood and embolic material enter the filter body 2. The outlet end 5 has a plurality of small outlet openings 7 which are sized to allow through passage of blood but to retain undesired embolic material within the filter body 2. In this way, the filter element 1 captures and safely retains any undesired embolic material in the blood stream within the filter body 2 while facilitating continued flow of blood through the vascular system. Emboli are thus prevented from flowing further downstream through the vascular system, which could otherwise have potentially catastrophic results.

The filter body 2 may be of an oriented polymeric material, as described in our WO 01/97714A and US 2002/0042627A, the relevant contents of which are incorporated herein by reference.

Figure 169A:
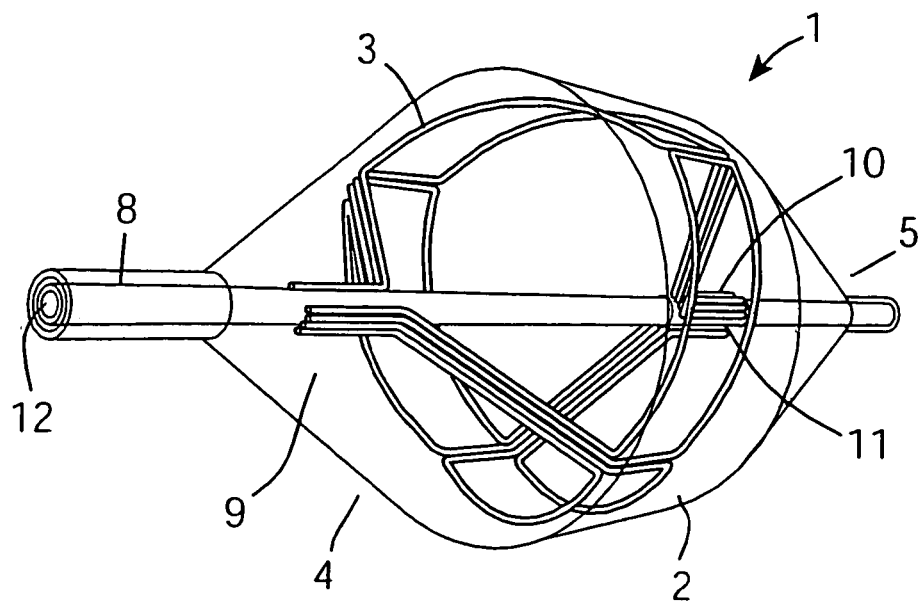
FIGS. 169(a) to 169(c) are perspective views illustrating collapse of the embolic protection device of FIG. 162.
Figure 169B:
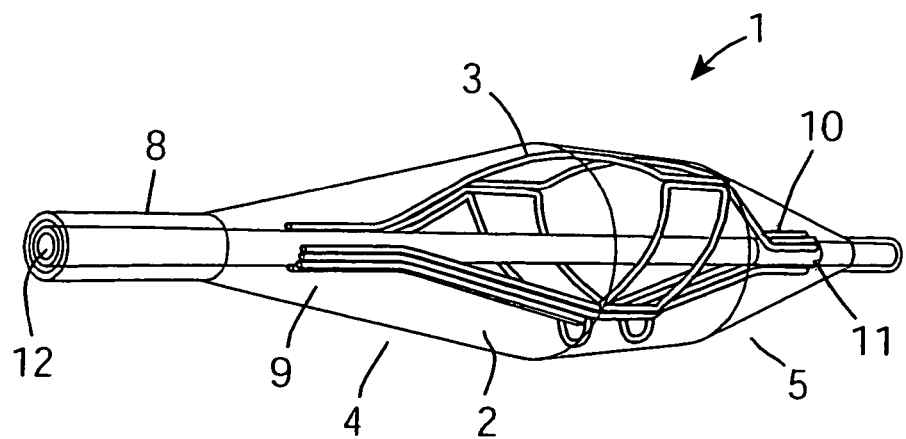
Figure 169C:
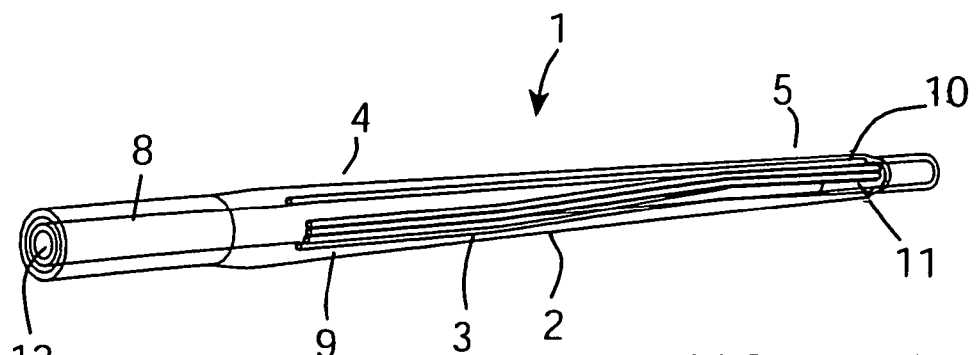

The filter support 3 is movable between a low profile, collapsed position (FIG. 169(*c*)) for movement through the vascular system, and an extended outwardly projecting position (FIG. 169(*a*)). As particularly illustrated in FIG. 2, in this outwardly projecting position, the filer body 2 is supported in an expanded position by the filter support 3 so as to maximise the internal volume of the filter body 2 to capture and safely retain as much embolic material as possible.

The inner tube 8 has a guidewire lumen 12 therethrough, through which a guidewire may pass for exchange of the filter element 1 over the guidewire.

Figure 164:
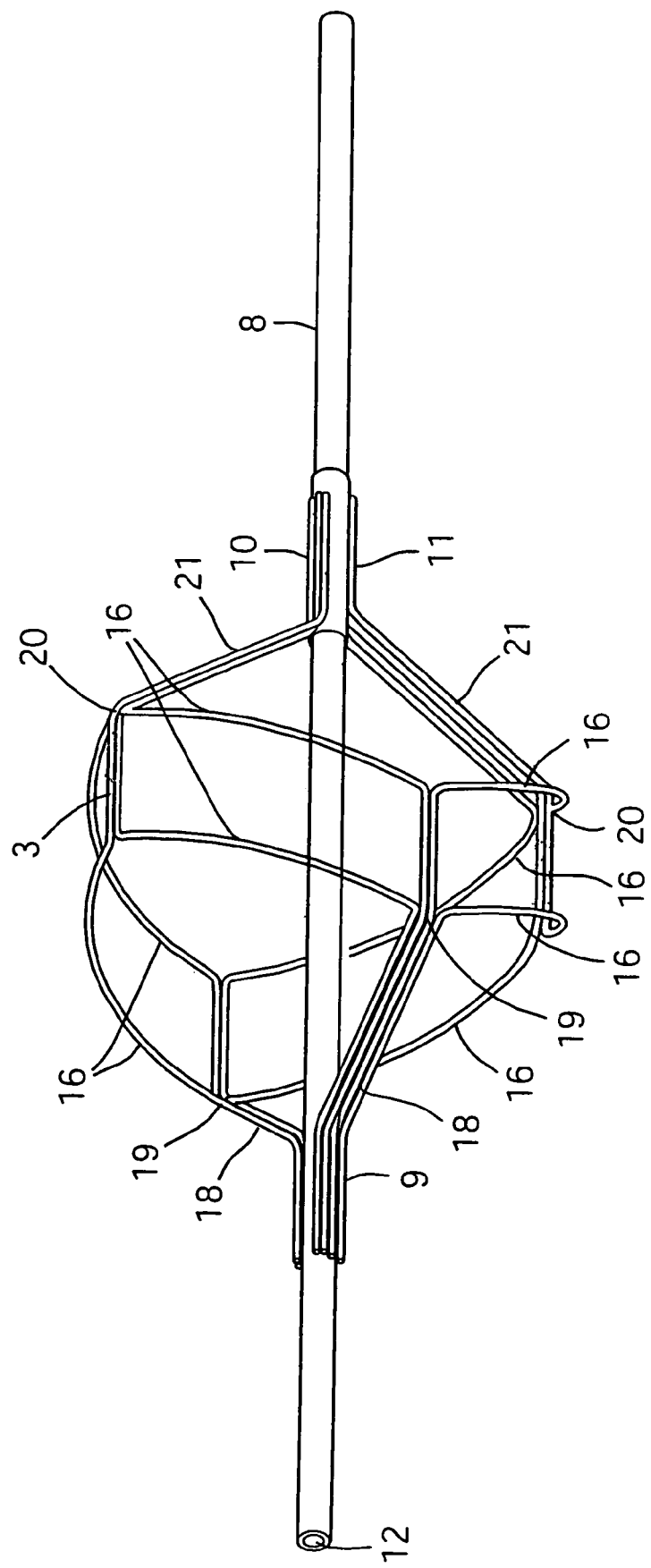
FIG. 164 is a perspective view from a side of a filter support and an inner tube of the embolic protection device of FIG. 162.
Figure 167:
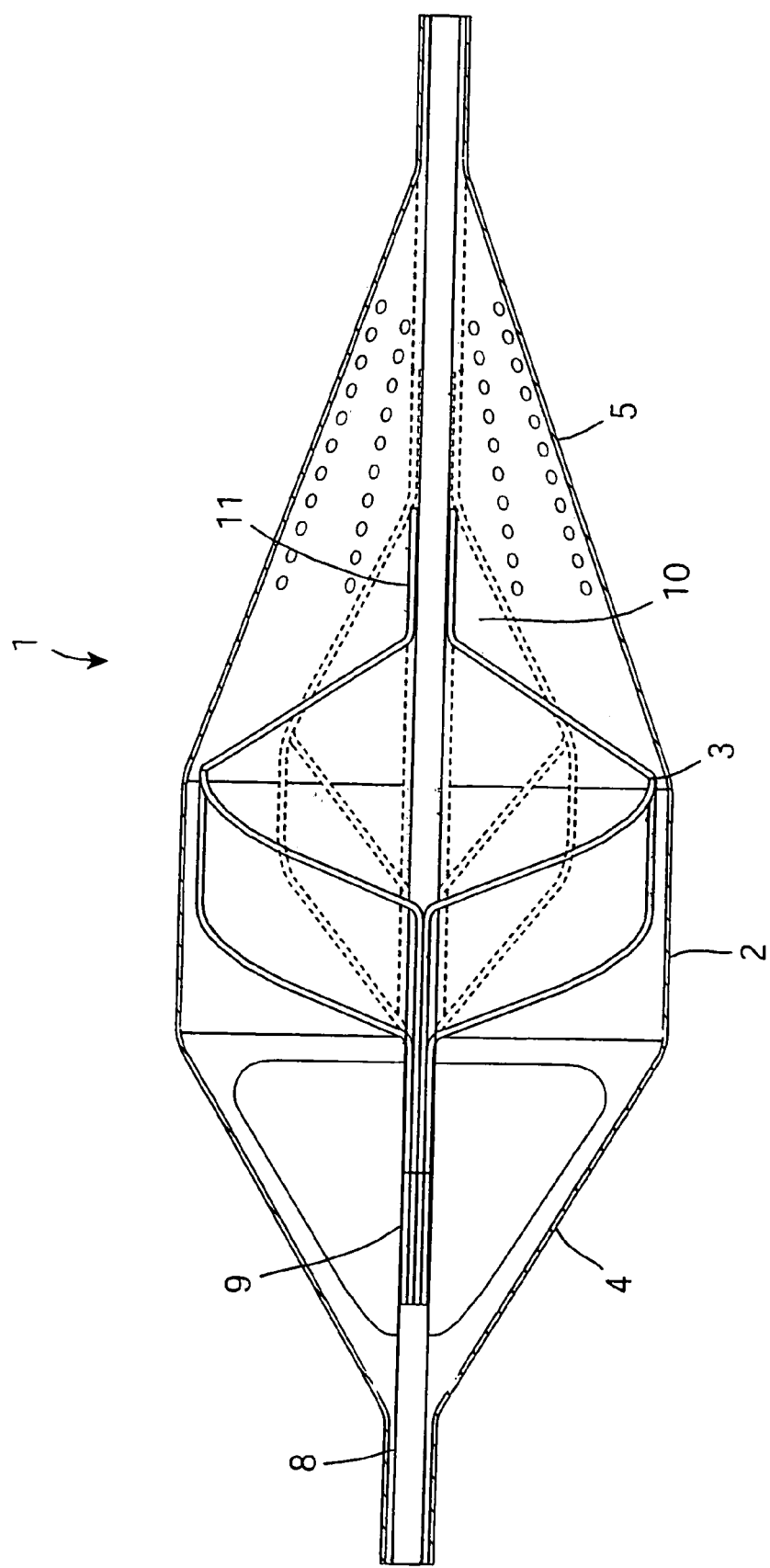
FIG. 167 is a schematic side view illustrating collapse of the embolic protection device of FIG. 162.
Figure 168:
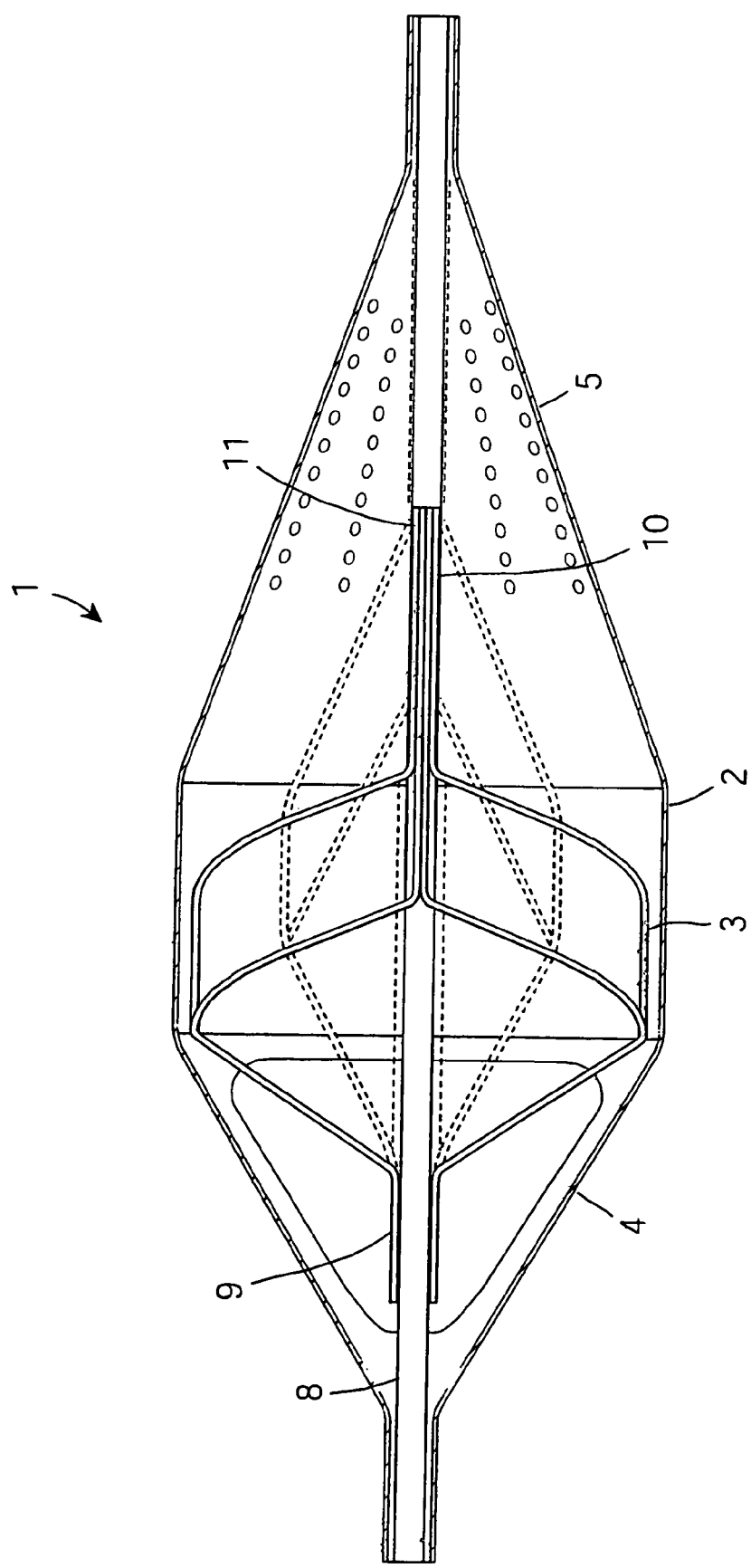
FIG. 168 is a schematic plan view illustrating collapse of the embolic protection device of FIG. 162.

The proximal end 9 of the filter support 3 is fixed to the inner tube 8, and the distal end 10 of the filter support 3 is fixed to a sleeve 11 which is slidable over the inner tube 8, as illustrated in FIG. 164. As illustrated in FIGS. 167 to 169(*c*), upon collapse of the filter element 1, the proximal end 9 of the filter support 3 remains fixed relative to the inner tube 8, and the distal sleeve 11 slides over the tube 8 (FIG. 169(*b*)), until the filter support 3 is fully collapsed against the inner tube 8 (FIG. 169(*c*)). The partially and fully collapsed positions of the filter support 3 are illustrated by dashed lines in FIGS. 167 and 168. In the fully collapsed position of (FIG. 169(*c*)), the filter support 3 is axially elongated relative to the expanded position.

Figure 165:
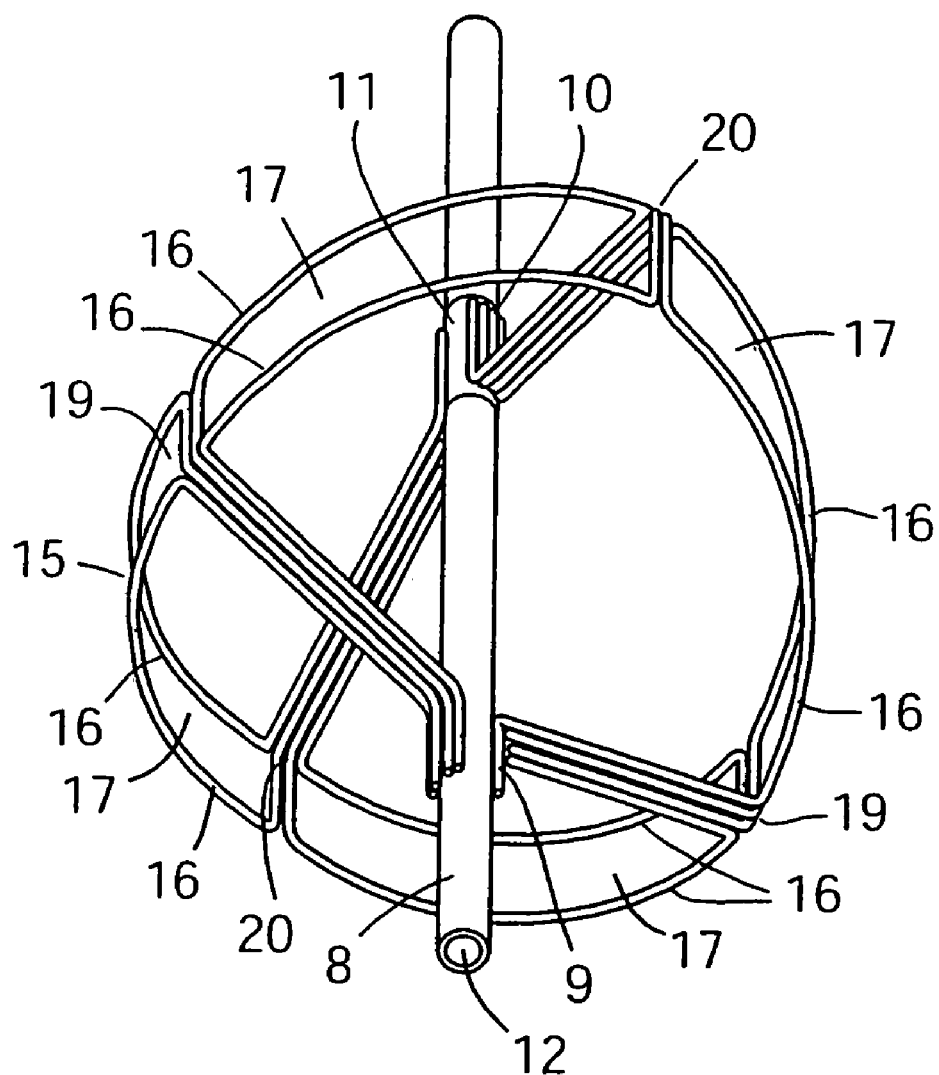
FIG. 165 is a perspective view from an end of the filter support and the inner tube of FIG. 164.
Figure 166:
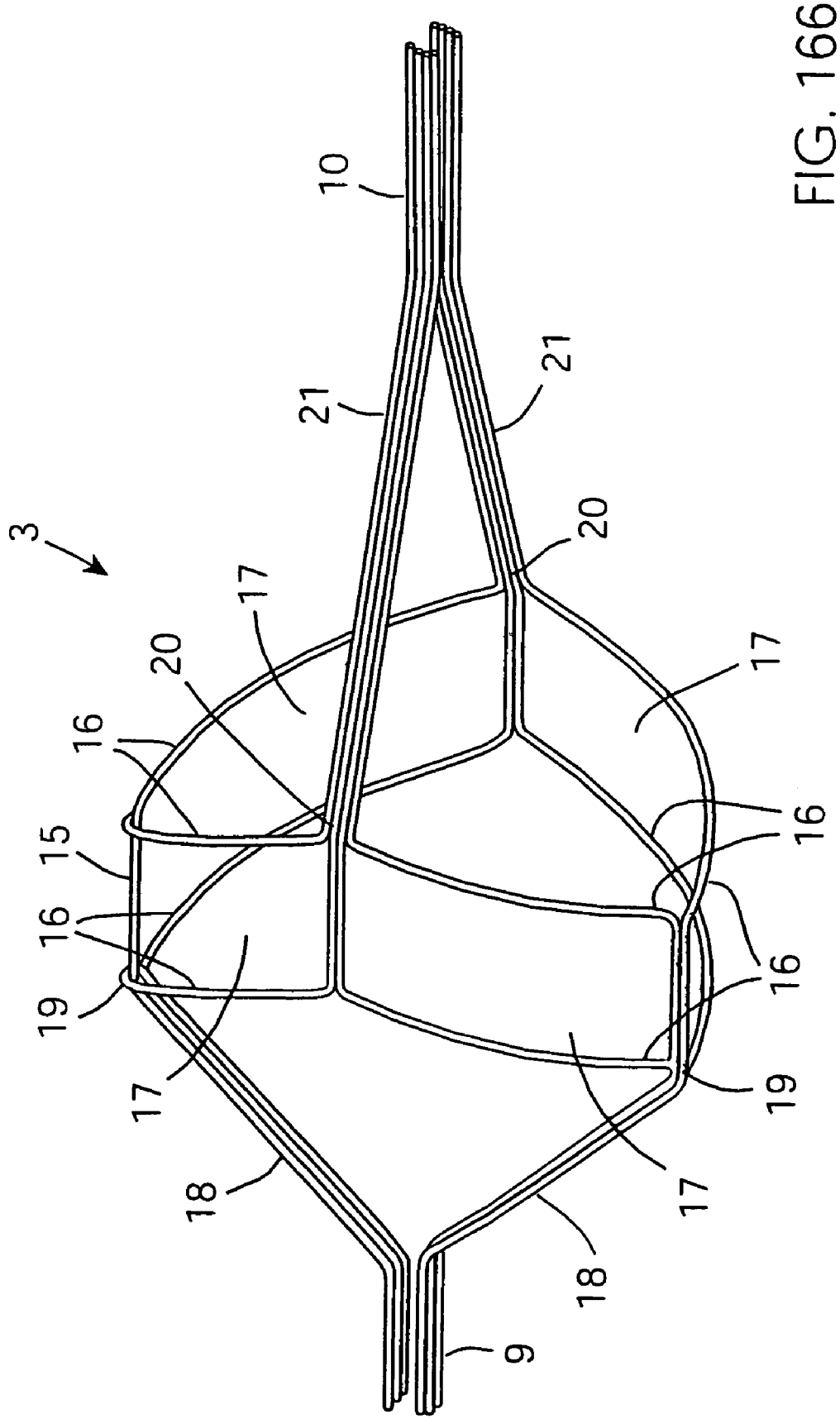
FIG. 166 is a perspective view of the filter support of FIG. 164.

The filter support 3 is illustrated in detail in FIGS. 164 to 166. The filter support 3 comprises eight round wires 16 which extend from the proximal end 9 to the distal end 10. The wires 16 extend axially and radially outwardly in two legs 18 from the proximal end 9, where the wires 16 are fixed to the inner tube 8, to a central tubular support frame portion 15. The junction points of the legs 18 with the tubular frame 15 are referred to in this specification as the proximal termination points 19.

At each proximal termination point 19, the wires 16 separate, and then extend axially along and circumferentially around the tubular frame 15 until symmetrical distal termination points 20 are reached. At these distal termination points 20, the wires 16 regroup into two legs 21 which extend axially and radially inwardly to the sleeve 11, to which the wires 16 are fixed. In this way, the wires 16 define the central tubular frame portion 15.

The path of the wires 16 around and along the tubular frame portion 15 defines four cells 17, with each cell 17 forming a segment of the tubular frame 15 (FIG. 166). Together the four cells 17 extend circumferentially around the tubular frame 15 in a complete loop.

This arrangement of the tubular frame 15 ensures that in the expanded position, the filter body 2 will be supported by the tubular frame 15 in tubular apposition with the interior wall of the vasculature. The tubular apposition further minimises the possibility of any flow path for blood occurring between the filter body 2 and the vasculature wall to bypass the filter element 1.

Each cell 17 is defined by two of the wires 16 which are arranged, in the expanded position, in a generally parallelogram, "hysteresis loop" shape. The length of each wire 16 around the cell 17 is equal. At the proximal and distal termination points 19, 20, adjacent wires 16 are fixed to each other, and extend generally axially and parallel in a bi-filar arrangement. Adjacent cells 17 within the tubular frame 15 are also connected together by fixing a wire 16 in one cell 17 to a wire 16 in an adjacent cell 17.

As the filter support 3 collapses down against the inner tube 8, the wires 16 around each cell 17 become torqued. This torqueing action is similar to the process of elongation of a coiled spring.

Because the tubular support frame 15 is defined by round wires 16, the torque developed in each wire 16 will be evenly distributed along the length of each wire 16. In addition, the bi-filar connection of the wires 16 to each other at the termination points 19, 20 further assists in torque distribution along the wires 16.

Thus, collapse of the filter support 3 does not induce high, localised stresses in the filter support 3. In this way, the filter support 3 may be constructed of wires 16 of a small cross-sectional area which will collapse down to a very low-profile. Furthermore the collapsed filter element 1 with small wires 16 has greater flexibility for ease of advancement of the filter element 1 through the vascular system.

As illustrated in FIGS. 165 and 166, the proximal termination points 19 are circumferentially offset by 90° from the distal termination points 20.

In use, the filter element 1 is collapsed down and loaded into a delivery catheter with an associated torqueing of the wires 16 around the cells 17. The filter element 1 is then delivered through a vasculature fixed to or over a guidewire using the delivery catheter until the filter element 1 is located at a desired site in the vasculature.

By moving the delivery catheter proximally relative to the filter element 1, the filter element 1 is deployed out of the delivery catheter at the desired site in the vasculature. The filter support 3 expands radially outwardly to support the filter body 2 in tubular apposition with the interior wall of the vasculature. In the fully expanded position, the wires 16 of the tubular support frame 15 are substantially free of torque.

The site of deployment of the filter element 1 in the vasculature is typically downstream of a treatment site, such as a region of stenosis in the vasculature. During the performance of a treatment procedure, the filter element 1 captures and safely retains any embolic material in the blood stream within the filter body 2.

After completion of the treatment procedure, the filter element 1 is collapsed down and retrieved into a retrieval catheter with any retained embolic material within the filter body 2. The wires 16 around the tubular wire support frame 15 are again torqued during collapse.

The retrieval catheter is then withdrawn from the vasculature with the filter element 1 within the retrieval catheter.

The delivery, deployment and retrieval of the embolic protection device of the invention, as described above, is similar to that described in our WO 99/23976A; WO 01/80776A (US 2002-0052676A) and WO 01/80773A (US 2002-0049467A), the relevant contents of which are incorporated herein by reference. The filter element 1 may be slidably exchanged over the guidewire without any attachment means between the filter element 1 and the guidewire. A distal stop on the guidewire assists in retrieval of the filter element 1. The guidewire may remain in the vasculature after retrieval of the filter element 1.

Figure 170:
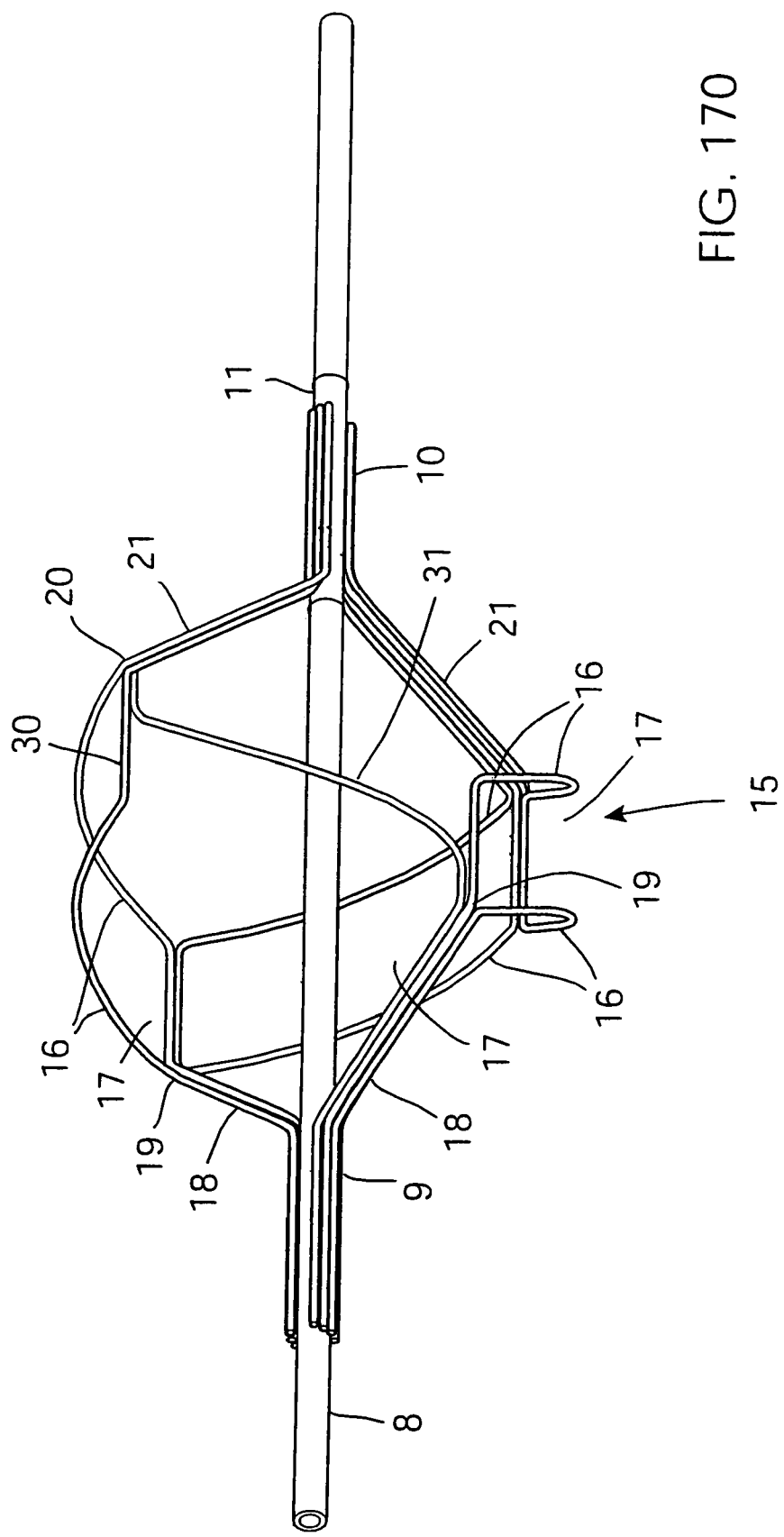
FIG. 170 is a perspective view of another filter support and the inner tube of FIG. 164.

FIG. 170 illustrates another filter support 30, which is similar to the filter support 3 of FIGS. 162 to 168, and similar elements in FIG. 170 are assigned the same reference numerals.

In this case, the filter support 30 comprises only six wires 16, which define only three tubular segment cells 17 as the wires 16 extend axially along and circumferentially around the tubular frame 15. The three cells 17 do not form a complete 360° loop around the tubular frame 15. An extension wire 31 is provided, in this case, to provide support to the filter body 2 between the two circumferentially spaced-apart cells 17. The linkage element 31 may provide a diameter adjusting feature.

Figure 171:
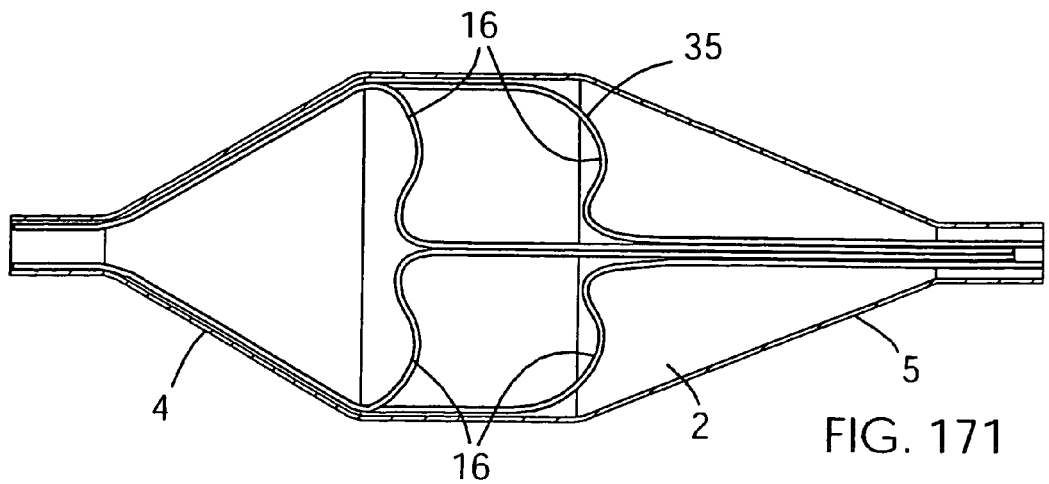
FIGS. 171 to 173 are plan, side and perspective views respectively of a further filter support.
Figure 172:
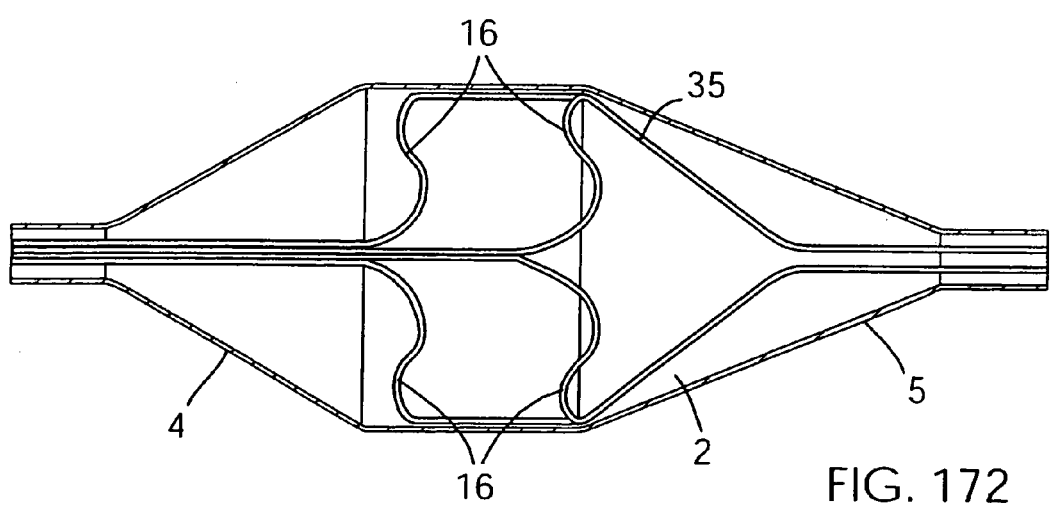
Figure 173:
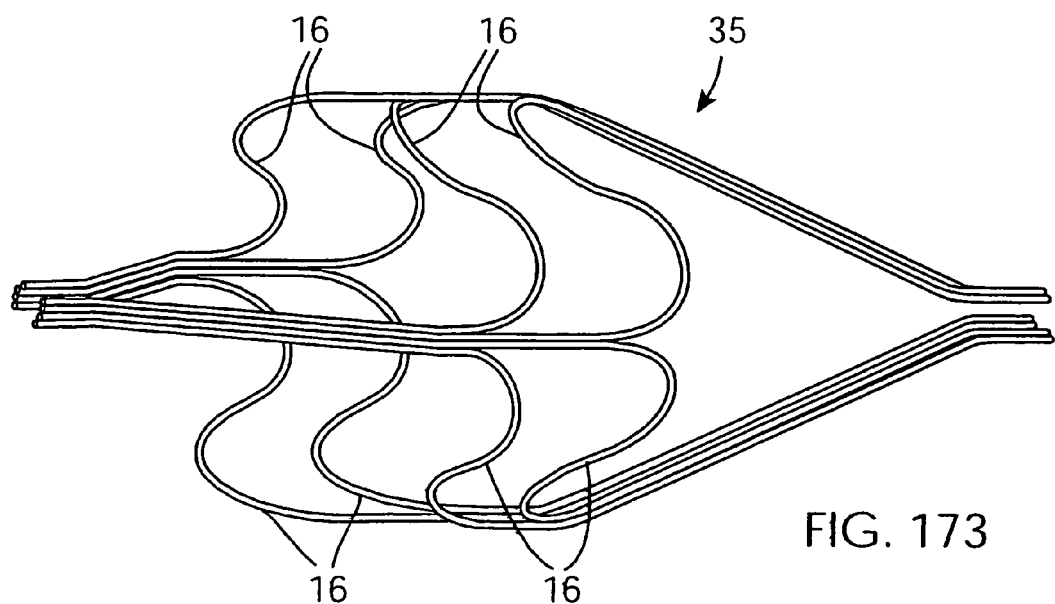

Referring to FIGS. 171 to 173, there is illustrated another filter support 35, which is similar to the filter support 3 of FIGS. 162 to 169, and similar elements in FIGS. 171 to 173 are assigned the same reference numerals.

The wires 16 extend, in this case, circumferentially around the tubular frame 15 in an "S-shape". The S-shape increases the contact area between the wires 16 and the filter body 2, and in this way, the supporting force exerted by the wires 16 on the filter body 2 is more evenly distributed. This arrangement minimises any trauma experienced by the vasculature due to the apposition of the filter element 1 with the vasculature.

Figure 174:
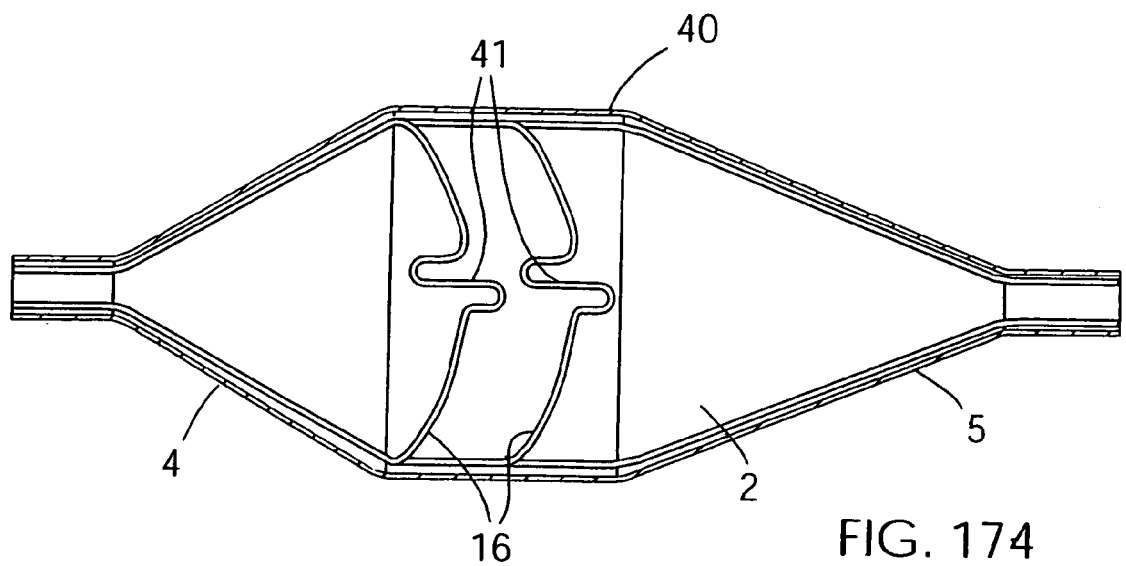
FIGS. 174 and 175 are side and perspective views respectively of another filter support.
Figure 175:
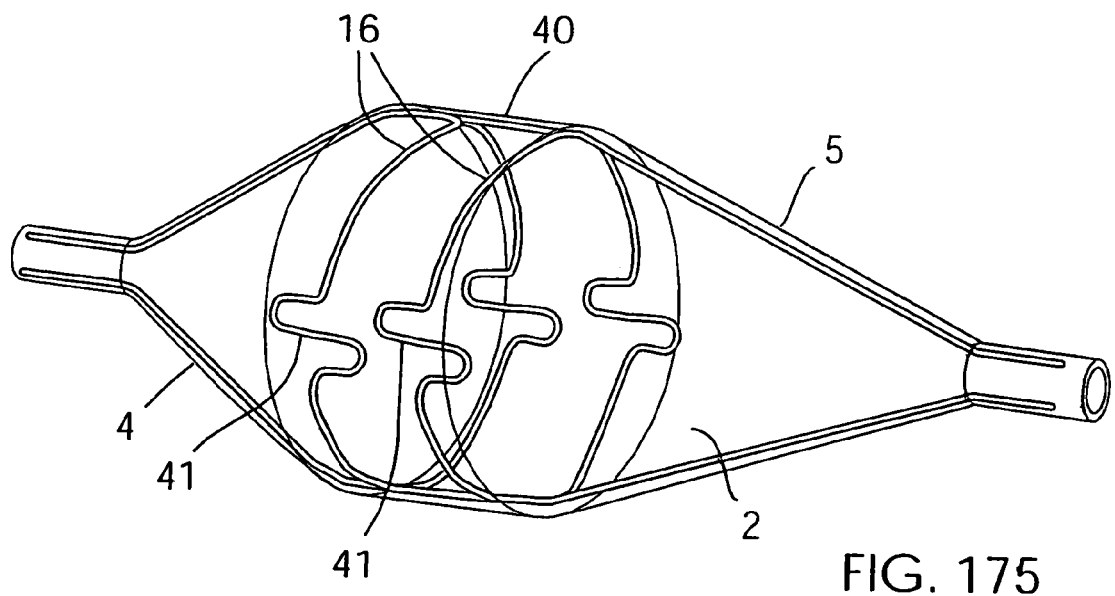

An alternative filter support 40 having wires 16 with a more exaggerated S-shaped portion 41 is illustrated in FIGS. 174 and 175.

It will be appreciated that the shape of one wire 16 of a cell 17 does not have to be symmetrical or similar to the shape of the other wire 16 of the cell 17, provided that the length of each wire 16 is equal.

Figure 176:
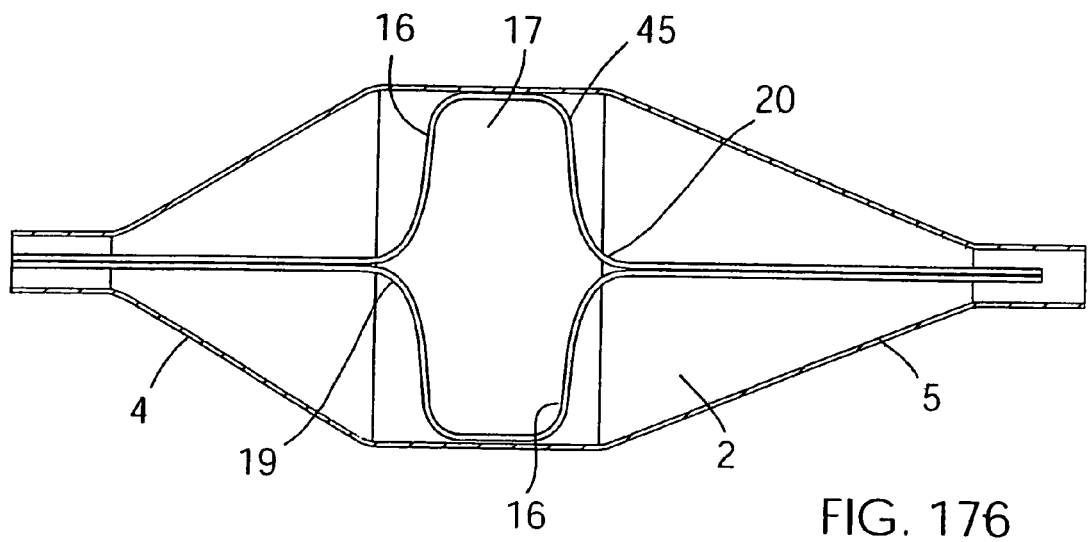
FIGS. 176 to 178 are plan, side and perspective views of a further filter support.
Figure 177:
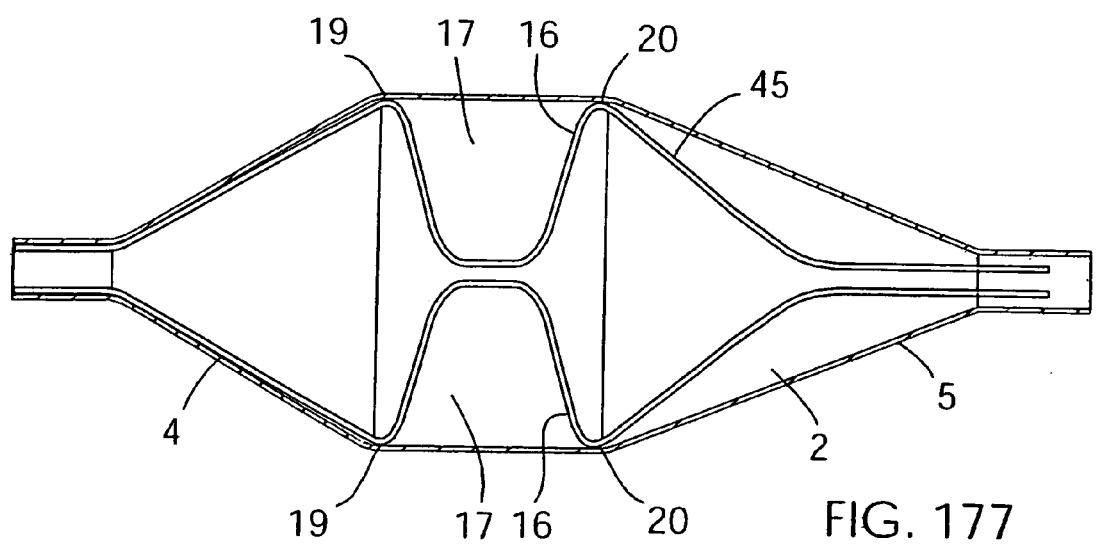
Figure 178:
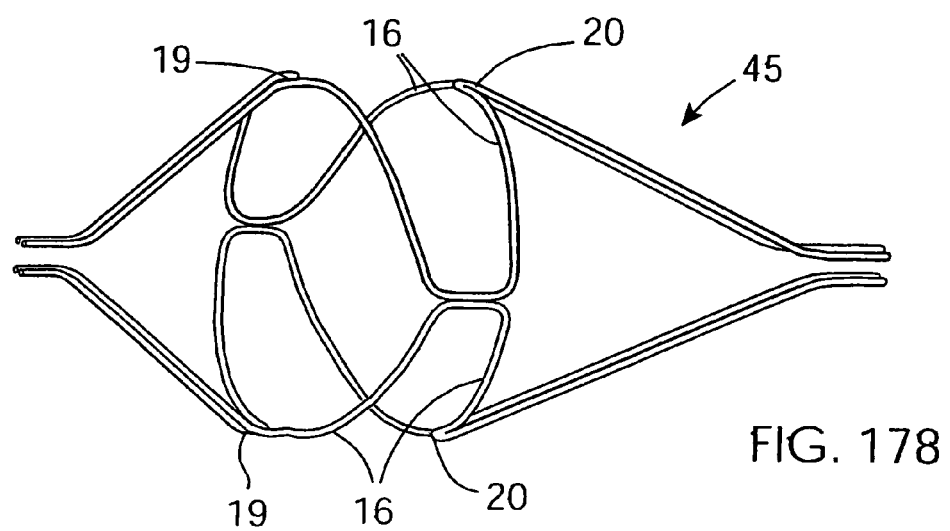

Referring to FIGS. 176 to 178, there is illustrated another filter support 45, which is similar to the filter support 3 of FIGS. 162 to 169, and similar elements in FIGS. 176 to 178 are assigned the same reference numerals.

In this case, the filter support 45 comprises only four wires 16, which extend circumferentially around and axially along the tubular support frame 15 to define two cells. The two cells have a hexagonal, hysteresis loop shape, and together the two cells 17 extend circumferentially around the tubular frame 15 in a complete loop.

The proximal termination points 19 are circumferentially aligned with the distal termination points 20.

Figure 179:
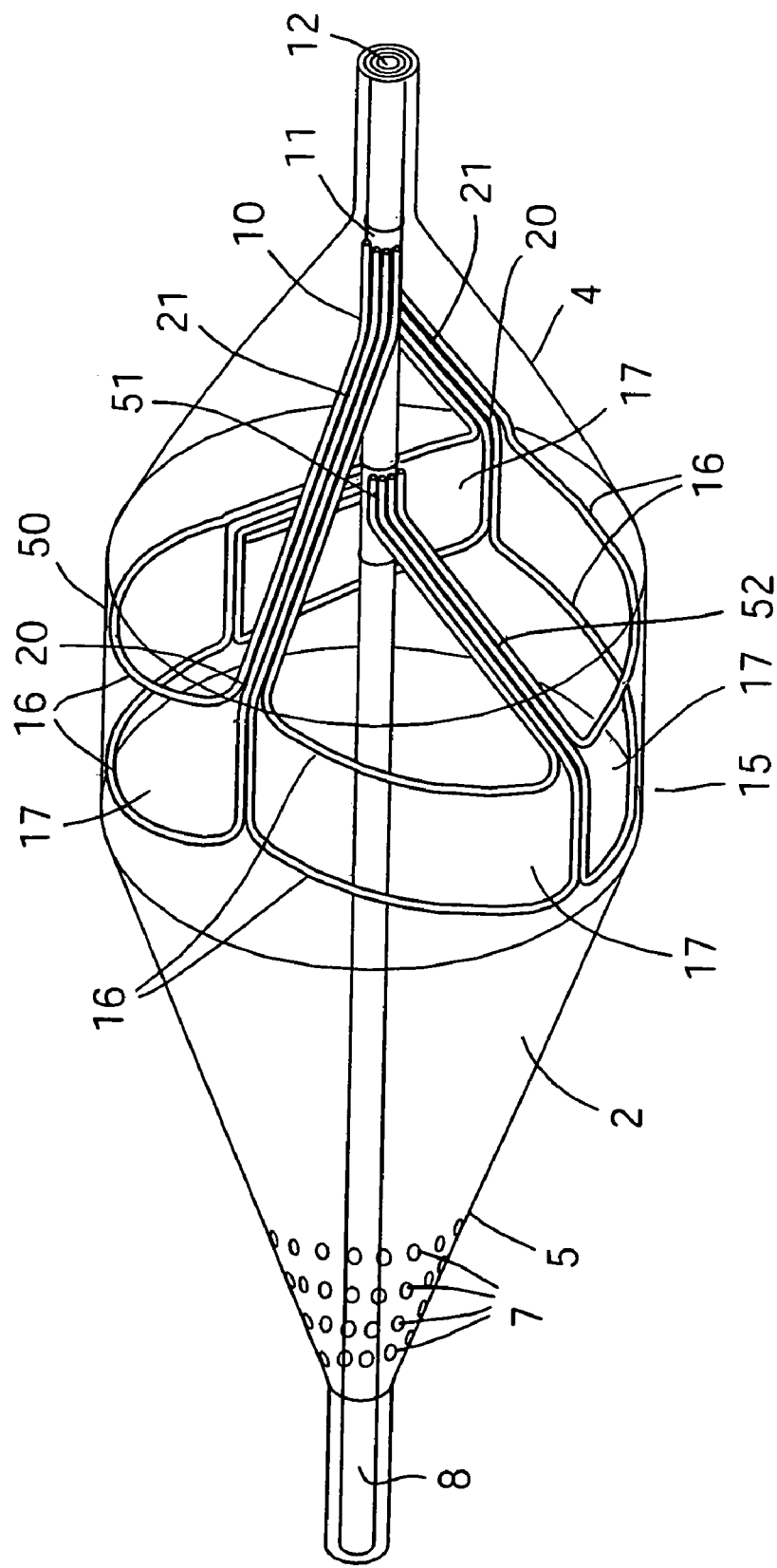
FIG. 179 is a perspective view of another embolic protection device according to the invention.
Figure 180:
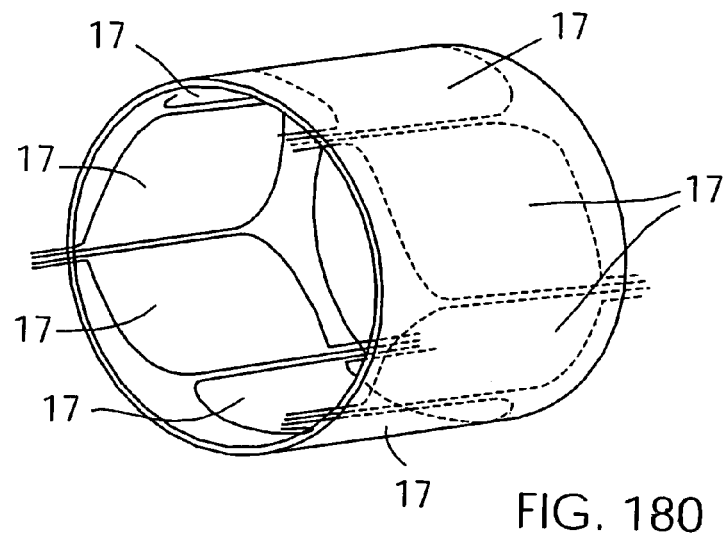
FIG. 180 is a schematic view of another filter support.

Another support frame 50, illustrated in FIG. 179, is similar to the support frame 3 of FIGS. 161 to 169, and similar elements if FIG. 179 are assigned the same reference numerals.

In this case, the wires 16 are fixed to inner tube 8 at a point 51 distally of the tubular support frame portion 15. The wires 16 extend from the fixation point 51 axially proximally and radially outwardly in a single leg 52 to the tubular support frame portion 15.

By providing a single proximal support leg 52, and by locating this leg 52 distally of the inlet end 4 of the filter body 2, this arrangement minimises the possibility of embolic material becoming caught or hung-up on the leg 18 at the inlet openings 6. In this manner, substantially all of the embolic material is retained safely within the filter body 2 for subsequent retrieval from the vascular system.

The wires 16 are preferably of a self-expanding material, such as Nitinol, and the inner tube 8 is preferably of gold. This arrangement provides for radiopacity.

Figure 18:
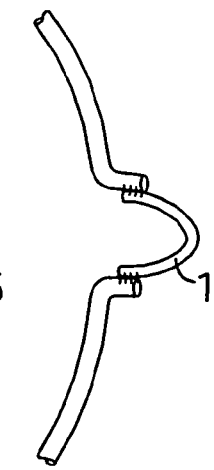
Figure 19:
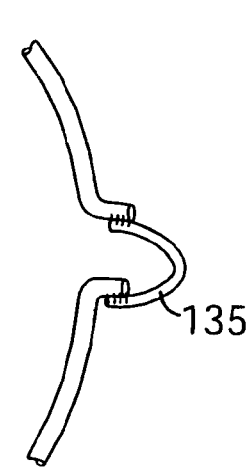
Figure 181:
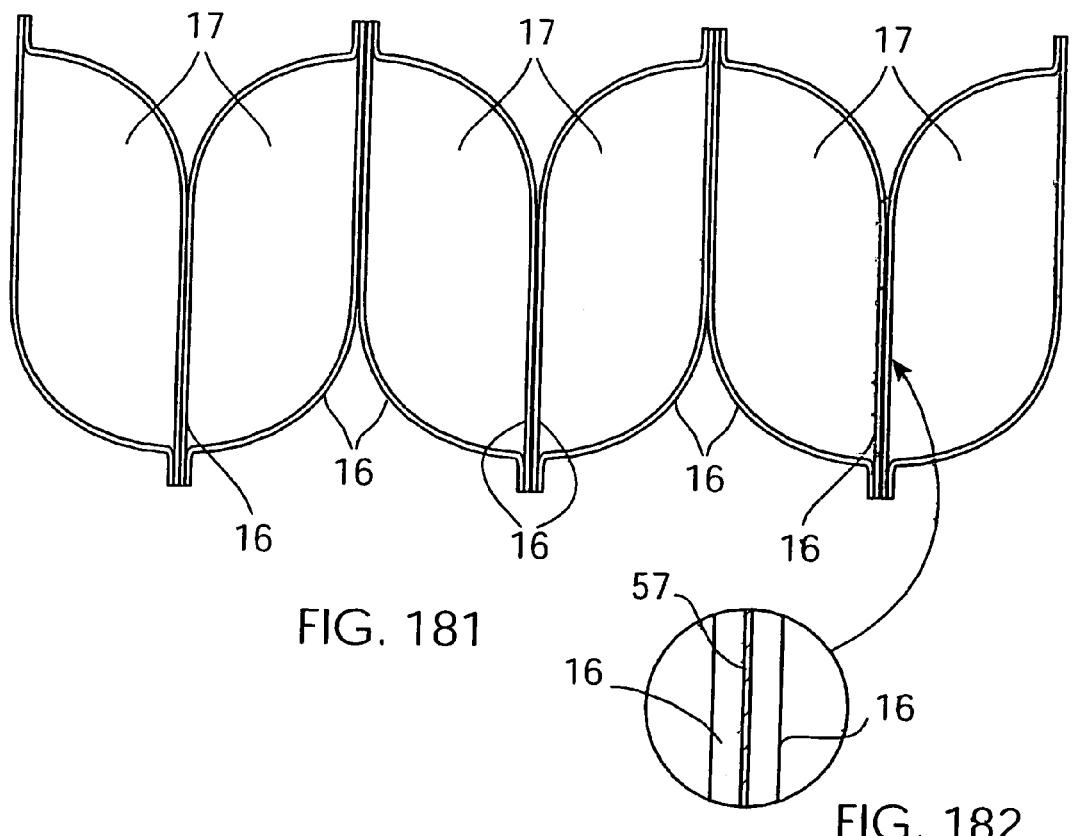
FIG. 181 is a development view of the filter support of FIG. 180.
Figure 182:
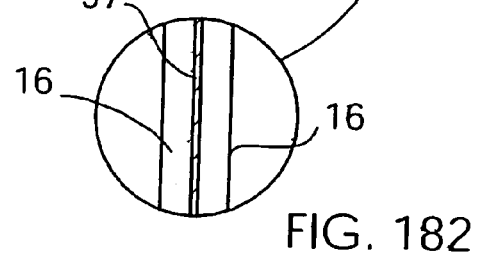
FIG. 182 is an enlarged view of part of the filter support of FIG. 181.

It will be appreciated that a plurality of cells 17 may be defined by the wires 16 around the tubular support frame 15, as illustrated in FIG. 18. Each wire 16 may be fixed to a wire 16 in an adjacent cell 17 (FIG. 181) by welding, or by adhesive means 57 (FIG. 182), or by any other suitable means.

The wires 16 may be slidably mounted to the inner tube 8 at both the proximal support leg 18 and the distal support leg 21.

By increasing the number of wires 16 which define the cells 17 of the tubular support frame 15, the elongation of the overall filter support, when collapsed down, is reduced. In this way, the space required in a vasculature to deploy and retrieve the embolic protection device is also reduced.

Depending on the configuration of the filter element, the inner tube may not be present. In this case the filter support will be mounted directly onto the guidewire for exchange of the filter element over the guidewire.

Figure 183:
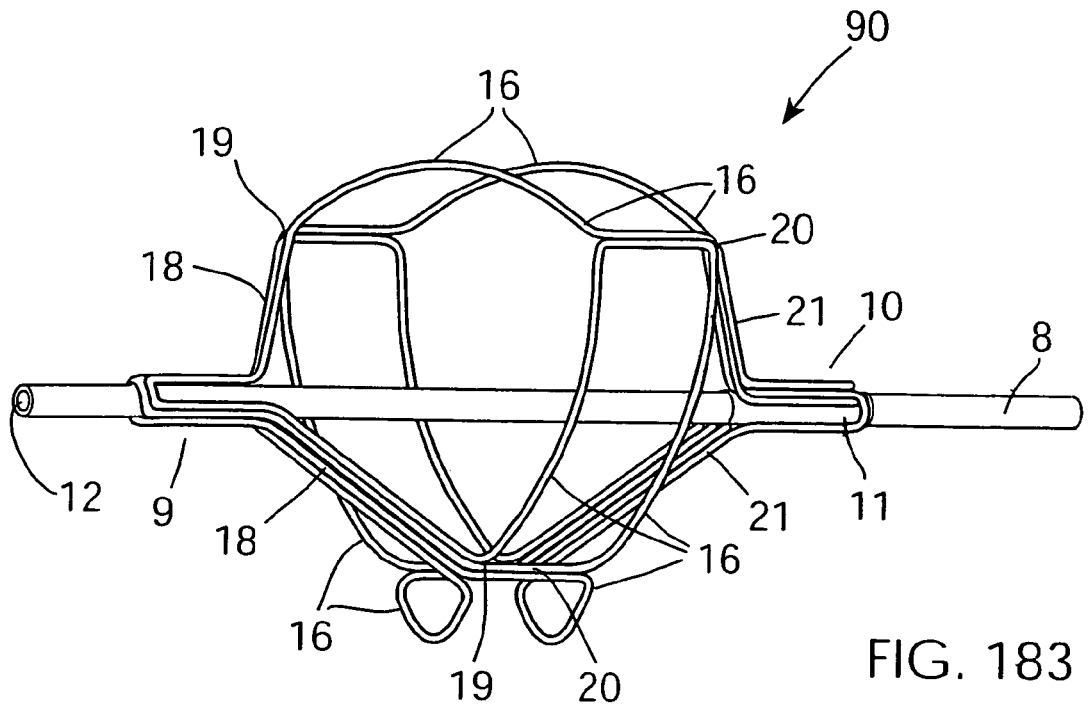
FIG. 183 is a perspective view of another filter support and inner tube.
Figure 184:
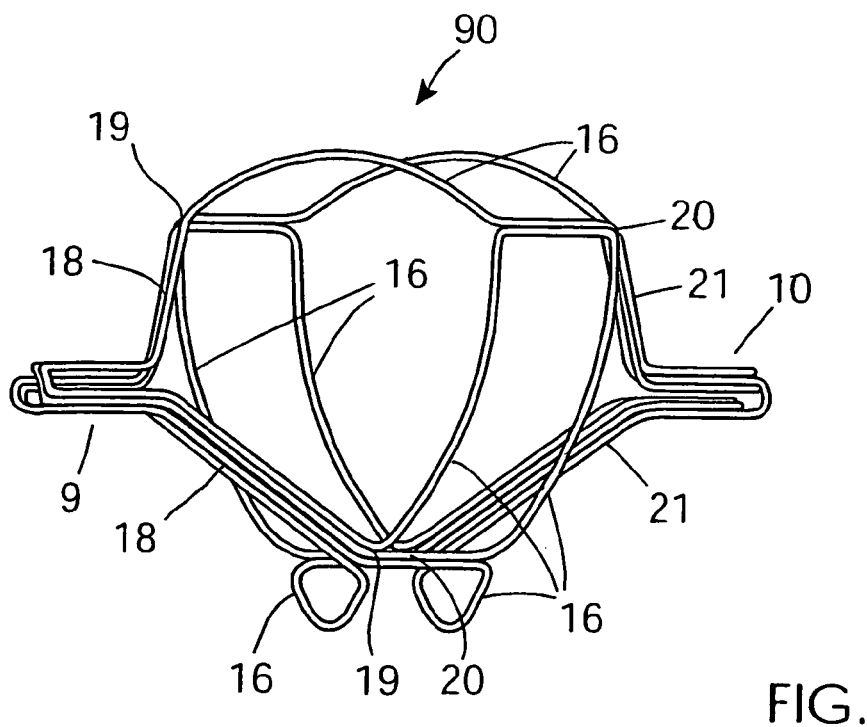
FIG. 184 is a perspective view of the filter support of FIG. 183.

It will be appreciated that a single wire 16, bent back on itself, may be used to define the tubular support frame 15, in which case the cells 17 of the tubular support frame 15 are defined by elements of the single wire 16, as illustrated in FIGS. 21 and 22. The support frame 90 of FIGS. 183 and 184 is similar to the support frame 3 above, with the exception that the support frame is defined by a single wire 16 bent back on itself.

A proximal neck of the filter body may be inverted to extend distally rather than proximally. This arrangement reduces the overall longitudinal length of the embolic protection device, and thus the embolic protection device may be deployed and retrieved with a shorter "parking space" in the vasculature. To invert the proximal neck, the neck may be split along each side, and then the pushed distally into the interior of the filter body.

In addition, the longitudinal length of the embolic protection device may be further shortened by providing a hemi-spherically shaped proximal nose instead of a conical nose. Furthermore, the overall crossing profile of the embolic protection device may be reduced by means of the hemispherical nose.

The invention incorporates circumferential wire angulation into support structure design to give maximum circumferential support to the filter membrane.

The angulated hysteresis structure/cell configurations of the invention are particularly suitable as support structures because the strain energy is distributed over long lengths of the wire structure. The wrapping/loading mechanisms of these hysteresis structures are both a bending/straightening of the constituent wires as well as a twisting/torsion of the wires. The energy applied/introduced during the loading process is both bending and torsional strain energy. These energies due to their nature and the method by which the support structure folds/loads are distributed over long lengths of the wire as opposed to concentrated focal points so that the level of energy within the wire at any point does not exceed the elastic strain energy limits. Hysteresis designs optimise the strain distribution along the wire lengths. With these designs there is distributed bending and torsional strain along the wires. The component of radial force is converted to torque strain energy. The corollary of this principle, that the torsional strain energy provides radial stiffness, also applies.

Angulated hysteresis structures also enable large radial forces to be achieved from structures with small wire diameters. The reason for this is that these designs use a greater proportion of the wires' torsional strain resistance. The wires offer far greater resistance to torsional strain than to bending strain and therefore these designs optimise this feature. The angulated hysteresis structure design arranges the wires so that the load induces torsional strain and therefore delivers far higher performance with small wire diameters than those designs that rely on the bending strain/resistance.

The hysteresis support structure of the invention has section/s of wire curvature that can be defined in 3D planes. These sections of wire have geometrical properties such as a radius of curvature and a centre of radius of curvature. As the hysteresis structure designs are loaded and deployed, the geometrical properties of these sections change—that is the radius of curvature changes and the centre for the radius of curvature moves in a path that can only be defined within a 3D plane.

Even relatively simple hysteresis designs are made up of numerous sections of curvature with their corresponding radius of curvature joined end to end to form a complete hysteresis loop. These sections of curvature depending on the complexity of the design may be combinations of concave and convex elements/segments. The hysteresis loops themselves can be various shapes and there are multitudes of hysteresis loop/cell geometries.

A wire or laser cut support structure design based on a hysteresis cell type design typically may have four arms acting to provide uniform radial force to give good vessel apposition. In attempting to provide support over the complete body length structure designs tend to have multiple arms/cells providing the support. The problems with many of these designs is the excessive elongation associated with them during loading. The advantage with the invention in suit is that it only extends the same length whether one/two or multiple arms are used. The invention also lends itself to low wrapping profiles, because during loading it contracts both radially and circumferentially leaving parallel straight wires which often prove to be the easiest for loading.

Further advantages of the round wire arrangements include:

Using a round wire allows for substantially more of the strain energy induced during loading/wrapping down into a low profile to be stored as torque along the wire lengths. This means that the strain energy is more evenly distributed within the wires than with conventional section designs, in which the strain energy generally becomes concentrated around the bend points which can cause problems such as exceeding the elastic strain energy limit at these locations.

The invention also has the advantage of being more trackable and flexible. This design achieves this by allowing the structure to hinge at points. Planes through these points demonstrate that bending at these hinge points is very easy.

Furthermore, the radial force may be altered by:
a) changing the wire diameter;
b) changing the proximal and distal cone angles.

Points of stress concentration can become strained plastically and result in poor support structure performance.

Conventional approaches to dealing with these issues involve designing in strain distributing geometric features to spread these strains over a greater area of the structure. Another approach involves the use of thinning out sections in the area of high strain. At a given radius of curvature the strain in a thin section is less than that of a thick section. Thinning however compromises the overall support provided by the structure.

The filter support of the invention provides for torsional strain and thus eliminates the need to use section thinning or thickening to distribute strain.

When torque stresses are applied to members of an approximately circular cross section the resulting strain becomes distributed over the length of the section. In this situation it is not possible to generate a corresponding torque phenomenon to the cantilever bending phenomenon. The present invention provides elements which are torsionally strained in the collapsed configuration and which release these torsional strains as they expand.

When collapse strains are evenly distributed, it is possible that the overall level of strain in the system can be increased without inducing plastic deformation. This makes it possible to achieve a high level of radial support from small diameter support members.

Designs that induce torque-strain into the support structure during collapse are particularly advantageous. Bending strains tend very often to have a strong cantilever effect with the strain becoming localised at points of stress concentration.

The torque strain in the wire can be released in a variety of expansion pathways. This means that the release of the torque is not inhibited when uniaxial resistance is encountered. This feature helps the support structure deliver good apposition to eccentric vessels. This is an important aspect of the invention, especially when the filter is placed in diseased vessel segments.

The geometric configuration of the filter support aligns the wires of the cell in a substantially circumferential direction in the expanded state. This ensures that radial pressure applied by the vessel is initially transmitted as compressive hoop stress to the structure.

The compressive component of applied stress decreases as the system collapses, however the torsional resistance increases resulting in a relatively flatter loading stress curve.

It will be appreciated that the body may be attached to or independent of the support frame.

The invention is not limited to the embodiments hereinbefore described which may be varied in detail.

The invention claimed is:

1. An embolic protection device comprising:
a collapsible filter element for delivery through a vascular system of a patient;
the filter element comprising a collapsible filter body and a filter support for the filter body;
the filter body having an inlet end and an outlet end, the inlet end of the filter body having one or more inlet openings sized to allow blood and embolic material to enter the filter body, the outlet end of the filter body having a plurality of outlet openings sized to allow through passage of blood but to retain undesired embolic material within the filter body;
the filter support being movable between a collapsed position for movement through the vascular system, and a fully extended outwardly projecting position to support the filter body in an expanded position;
the filter support comprising:
a support frame,
a carrier extending longitudinally through the support frame, and
a tether extending between the carrier and the support frame, the tether being fixed adjacent a distal end of the carrier and the support frame being fixed to a proximal end of the carrier, wherein in the fully extended outwardly projecting position the tether has a taut configuration, and in the collapsed position the tether has a slack configuration.

2. A device as claimed in claim 1 wherein the carrier is a tubular member.

3. A device as claimed in claim 1 wherein the carrier is a guidewire.

4. A device as claimed in claim 1 wherein the filter support comprises a number of segments, at least some of which are interconnected by a strain distributing linking element.

5. A device as claimed in claim 4 wherein the linking element is comprised of wire.

6. A device as claimed in claim 4 wherein at least some of the segments are comprised of wire.

7. A device as claimed in claim 6 wherein the linking element is comprised of the same wire as that of the segments.

8. A device as claimed in claim 6 wherein the wire element has a round cross-section.

9. A device as claimed in claim 6 wherein the wire has an elongate cross-section with a long dimension and a short dimension.

10. A device as claimed in claim 9 wherein the short dimension of the wire cross-section is aligned substantially along the radial direction of the filter support.

11. A device as claimed in claim 4 wherein the tether is attached to the linking element.

12. A device as claimed in claim 4 wherein the linking element extends normally of adjacent segments when the filter support is in the fully extended position.

13. A device as claimed in claim 4 wherein the linking element extends longitudinally of the axis of the filter when the filter support is in the fully extended position.

14. A device as claimed in claim 4 wherein the linking element extends radially inwardly of the adjacent segments when the filter support is in the fully extended position.

15. A device as claimed in claim 4 wherein the linking element comprises a loop.

16. A device as claimed in claim 15 wherein the loop is of a generally omega shape.

17. A device as claimed in claim 4 wherein at least a portion of the linking element is radiopaque.

18. A device as claimed in claim 4 wherein at least some of the support segments are radiopaque.

19. A device as claimed in claim 4 wherein the linking element is of multifilament construction.

20. A device as claimed in claim 4 wherein at least one of the segments is of multifilament construction.

21. A device as claimed in claim 1 wherein the support frame is defined by at least two wire segments having terminations, the terminations of adjacent segments being fixed relative to one another and extending generally parallel.

22. A device as claimed in claim 1 wherein the support frame is defined by at least two wire segments terminating distally, the distal terminations of adjacent segments being fixed relative to one another and extending generally parallel.

23. A device as claimed in claim 1 wherein the support frame is defined by at least two wire segments terminating proximally, the proximal terminations of adjacent segments being fixed relative to one another and extending generally parallel.

24. A device as claimed in claim 1 wherein the support frame comprises a support hoop.

25. A device as claimed in claim 1 wherein the support frame comprises a support arm for one end of the filter body which extends towards an opposite end of the filter body in the deployed configuration.

26. A device as claimed in claim 25 wherein the support arm is a proximal support arm that extends distally in the deployed configuration.

27. A device as claimed in claim 25 wherein the support arm is connected to the carrier.

28. A device as claimed in claim 1 wherein the filter support comprises a generally tubular support frame defined by at least one wire.

29. A device as claimed in claim 1 wherein the filter support comprises a support frame having at least two longitudinally spaced-apart segments which are interconnected by at least one flexible linking element.

30. A device as claimed in claim 29 wherein the support frame segments are of wire.

31. A device as claimed in claim 1 wherein the wire is rectangular in cross-section.

32. A device as claimed in claim 1 wherein in the slack configuration, the tether is substantially folded down.

33. A device as claimed in claim 1 wherein the tether is fixedly attached to the carrier.

34. A device as claimed in claim 33 wherein the carrier defines an external surface, and the tether is fixedly attached to the external surface of the carrier.

35. A device as claimed in claim 1 wherein the tether comprises a wire.

* * * * *